US005484726A

United States Patent [19]
Basset et al.

[11] Patent Number: 5,484,726
[45] Date of Patent: Jan. 16, 1996

[54] ANTIBODIES SPECIFIC FOR HUMAN STROMELYSIN-3 AND A METHOD FOR DETECTION OF STROMELYSIN-3

[75] Inventors: Paul Basset; Jean-Pierre Bellocq, both of Strasbourg; Pierre Chambon, Bleasheim, all of France

[73] Assignees: Bristol-Myers Squibb Company, Princeton, N.J.; Institute National de la Sante et de la Recherche Medicale; Centre National de la Recherche Scientifique, both of Paris Cedex, France; Université Louis Pasteur, Strasbourg Cedex, France

[21] Appl. No.: 1,711

[22] Filed: Jan. 7, 1993

Related U.S. Application Data

[63] Continuation-in-part of Ser. No. 794,393, Nov. 21, 1991, Pat. No. 5,236,844.

[30] Foreign Application Priority Data

Nov. 21, 1990 [GB] United Kingdom .................. 9025326

[51] Int. Cl.$^6$ ............................ C12Q 1/25; C07K 16/40; C07K 16/30
[52] U.S. Cl. .................... 435/7.4; 530/387.1; 530/388.1; 530/387.7; 530/388.26; 530/388.8
[58] Field of Search ................................ 435/7.23, 7.1, 435/7.4; 530/387.1, 388.1, 387.7, 388.26, 388.8

[56] References Cited

PUBLICATIONS

Poupon, M. F. et al. (1991) Bulletin Du Cancer 78: 767–768.
Majmudar et al. (1992) Journal of Investigative Dermatology 98: 572, Abstract 121.
Hahnel et al. (1993) Journal of Cancer 55: 771–774.
Urbanski et al. (1992) British J. Cancer 66: 1188–1194.
Ahmed, Ali, "The Myofibroblast in Breast Disease", *Pathol. Annu.* 25(Pt 2): 237–286 (1990).
Basset, Paul et al., "Expression of the Stromelysin–3 Gene in Fibroblastic Cells of Invasive Carcinomas of the Breast and Other Human Tissues: A Review", *Breast Cancer Research and Treatment* 24:185–193 (1993).
Basset, Paul et al., "A Novel Metalloproteinase Gene Specifically Expressed in Stromal Cells of Breast Carcinomas", *Nature* 348:699–704 (Dec. 20, 1990).
Blood, Christine H. et al., "Tumor Interactions with the Vasculature: Angiogenesis and Tumor Metastasis", *Biochim. et Biophys. Acta* 1032:89–118 (1990).
Chiquet–Ehrismann, Ruth et al., "Tenascin: an Extracellular Matrix Protein Involved in Tissue Interactions during Fetal Development and Oncogenesis", *Cell* 47:131–139 (Oct. 10, 1986).
DeOme, K. B. et al., "Detection of Inapparent Nodule–transformed Cells in the Mammary Gland Tissues of Virgin Female BALB/cfC3H Mice", *Cancer Research* 38:2103–2111 (Jul. 1978).
Fidler, Isaiah J., "Origin and Biology of Cancer Metastasis", *Cytometry* 10:673–680 (1989).
Fidler, Isaiah J., "Rationale and Methods for the Use of Nude Mice to Study the Biology and Therapy of Human Cancer Metastasis", *Cancer and Metastasis Reviews* 5:29–49 (1986).
Garcia, M. et al., "Immunohistochemical Distribution of the 52–kDa Protein in Mammary Tumors: A Marker Associated with Cell Proliferation Rather Than With Hormone Responsiveness", *J. Steroid Biochem.* 27(1–3):439–445.
Goldberg, Gregory I. et al., "Human Fibroblast Collagenase–Complete Primary Structure and Homology to an Oncogene Transformation–Induced Rat Protein", *J. Biol. Chem.* 261(14):6600–6605 (May 15, 1986).
Grey, Anne–Marie et al., "Purification of the Migration Stimulating Factor Produced by Fetal and Breast Cancer Patient Fibroblasts", *PNAS USA* 86:2438–2442 (Apr. 1989).
Gullick, W. J., "Growth Factors and Oncogenes in Breast Cancer", *Progress in Growth Factor Research* 2:1–13 (1990).
Hart, Ian R. et al., "Molecular Aspects of the Metastatic Cascade", *Biochim. et Biophys. Acta* 989:65–84 (1989).
Kerr, Lawrence D. et al., "Growth Factors Regulate Transin Gene Expression By c–fos–Dependent and c–fos–Independent Pathways", *Science* 242:1424–1427 (Dec. 9, 1988).
Lefebvre, Olivier et al., "The Breast Cancer–Associated Stromelysin–3 Gene is Expressed During Mouse Mammary Gland Apoptosis", *J. Cell Biology* 119(4):997–1002 (Nov. 1992).
Levy, Annie et al., "Assignment of the Human Stromelysin 3 (STMY3) Gene to the q11.2 Region of Chromosome 22", *Genomics* 13:881–883 (1992).
Liotta, Lance A., "Tumor Invasion and Metastases–Role of the Extracellular Matrix: Rhoads Memorial Award Lecture", *Cancer Research* 46:1–7 (Jan. 1986).
Lippman, Marc E. et al., "Mechanisms of Growth Control in Normal and Malignant Breast Epithelium", *Recent Progress in Hormone Research* 45:383–440 (1989).
Matrisian, Lynn M., "Metalloproteinases and Their Inhibitors in Matrix Remodeling", *Trends in Genetics* 6(4):121–125 (Apr. 1990).
Milaire, J., "Aspects of Limb Morphogenesis", in *Organogenesis (R. L. De Haan and H. Ursprung, eds.)*, Holt, Rinehart and Winston, New York, pp. 283–300 (1965).
Monteagudo, Carlos et al., "Immunohistochemical Distribution of Type IV Collagenase in Normal, Benign, and Malignant Breast Tissue", *Am. J. Path.* 136(3):585–592 (Mar. 1990).

(List continued on next page.)

*Primary Examiner*—Margaret Parr
*Assistant Examiner*—Lisa Arthur
*Attorney, Agent, or Firm*—Sterne, Kessler, Goldstein & Fox

[57] ABSTRACT

The present invention relates to a gene encoding stromylsin-3, which is a new member of the metalloproteinase family. Expression of the stromelysin-3 gene has been found to be specifically associated with invasive breast, head, neck and skin cancer. The invention also relates to antibodies which specifically bind to human stromylsin-3 and the use of these stromelysin-3 antibodies for detection of the stromylsin-3 protein in a sample.

6 Claims, 29 Drawing Sheets

OTHER PUBLICATIONS

Muller, Danièle et al., "The Collagenase Gene Family in Humans Consists of at Least Four Members", *Biochem. J.* 253:187–192 (1988).

Muller, Danièle et al., "Expression of Collagenase–Related Metalloproteinase Genes in Human Lung or Head and Neck Tumours", *Int. J. Cancer* 48:550–556 (1991).

Muller, Danièle et al., "Increased Stromelysin 3 Gene Expression Is Associated with Increased Local Invasiveness in Head and Neck Squamous Cell Carcinomas", *Cancer Research* 53:165–169 (Jan. 1, 1993).

Murphy, George J. P. et al., "The Origin of Matrix Metalloproteinases and Their Familial Relationships", *FEBS* 289(1):4–7 (Sep. 1991).

Nowell, Peter C., "Mechanisms of Tumor Progression", *Cancer Research* 46:2203–2207 (May 1986).

Polette, Myriam et al., "Detection of mRNAs Encoding Collagenase I and Stromelysin 2 in Carcinomas of the Head and Neck by in situ Hybridization", *Invasion Metastasis* 11:76–83 (1991).

Salomon, David S. et al., "Tumor–Associated Growth Factors in Malignant Rodent and Human Mammary Epithelial Cells", in *Breast Cancer: Cellular and Molecular Biology* (M. E. Lippman and R. B. Dickson, eds.), Kluwer Academic Publishers, Boston, pp. 363–389 (1988).

Tremblay, Gilles, "Stromal Aspects of Breast Carcinoma", *Experimental and Molecular Pathology* 31:248–260 (1979).

Weinberg, Robert A., "Oncogenes, Antioncogenes, and the Molecular Bases of Multistep Carcinogenesis", *Cancer Research* 49:3713–3721 (Jul. 15, 1989).

Whitham, Sarah E. et al., "Comparison of Human Stromelysin and Collagenase by Cloning and Sequence Analysis", *Biochem. J.* 240:913–916 (1986).

Willett, Walter, "The Search for the Causes of Breast and Colon Cancer", *Nature* 338:389–394 (Mar. 30, 1989).

Wolf, Catherine et al., "Breast–Cancer–Associated Stromelysin–3 Gene Is Expressed in Basal Cell Carcinoma and During Cutaneous Wound Healing", *J. Invest. Dermatol.* 99:870–872 (Dec. 1992).

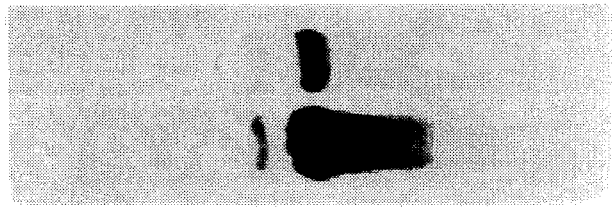 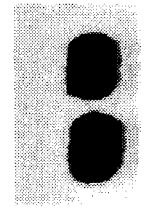
FIG. 1D
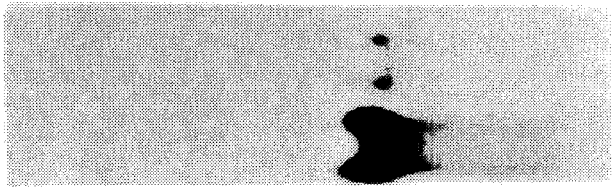 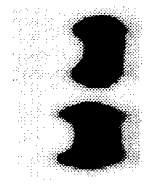
FIG. 1C
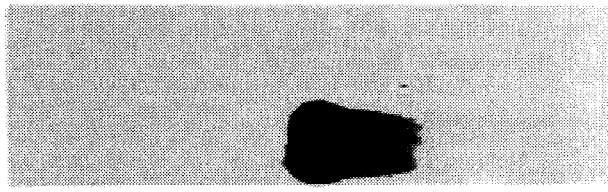 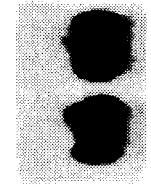
FIG. 1B
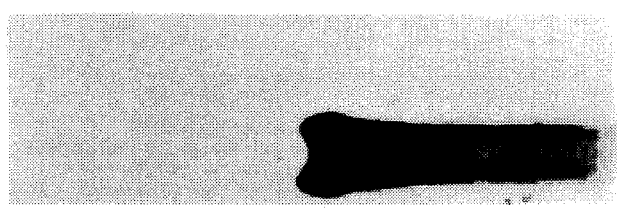 
FIG. 1A

```
CCGGGGCCGGATGGCTCCGGCCGCCTGGCTCCGCAGCGCGGCCGCGCGCGCCCTCCTGCCC    60
            M  A  P  A  A  W  L  R  S  A  A  A  R  A  L  L  P    17

CCGATGCTGCTGCTGCTGCTCCAGCCGCCGCCGCTGCTGGCCCGGGCTCTGCCGCCGGAC   120
 P  M  L  L  L  L  Q  P  P  P  L  L  A  R  A  L  P  P  D       37

GTCCACCACCTCCATGCCGAGAGGAGGGGGCCACAGCCCTGGCATGCAGCCCTGCCCAGT   180
 V  H  H  L  H  A  E  R  R  G  P  Q  P  W  H  A  A  L  P  S    57

AGCCCGGCACCTGCCCCTGCCACGCAGGAAGCCCCCCGGCCTGCCAGCAGCCTCAGGCCT   240
 S  P  A  P  A  P  A  T  Q  E  A  P  R  P  A  S  S  L  R  P    77

CCCCGCTGTGGCGTGCCCGACCCATCTGATGGGCTGAGTGCCCGCAACCGACAGAAGAGG   300
 P  R  C  G  V  P  D  P  S  D  G  L  S  A  R  N  R  Q  K  R    97

TTCGTGCTTTCTGGCGGGCGCTGGGAGAAGACGGACCTCACCTACAGGATCCTTCGGTTC   360
 F  V  L  S  G  G  R  W  E  K  T  D  L  T  Y  R  I  L  R  F   117

CCATGGCAGTTGGTGCAGGAGCAGGTGCGGCAGACGATGGCAGAGGCCCTAAAGGTATGG   420
 P  W  Q  L  V  Q  E  Q  V  R  Q  T  M  A  E  A  L  K  V  W   137

AGCGATGTGACGCCACTCACCTTTACTGAGGTGCACGAGGGCCGTGCTGACATCATGATC   480
 S  D  V  T  P  L  T  F  T  E  V  H  E  G  R  A  D  I  M  I   157

GACTTCGCCAGGTACTGGCATGGGACGACCTGCCGTTTGATGGGCCTGGGGGCATCCTG   540
 D  F  A  R  Y  W  H  G  D  D  L  P  F  D  G  P  G  G  I  L   177

GCCCATGCCTTCTTCCCCAAGACTCACCGAGAAGGGGATGTCCACTTCGACTATGATGAG   600
 A  H  A  F  F  P  K  T  H  R  E  G  D  V  H  F  D  Y  D  E   197

ACCTGGACTATCGGGGATGACCAGGGCACAGACCTGCTGCAGGTGGCAGCCCATGAATTT   660
 T  W  T  I  G  D  D  Q  G  T  D  L  L  Q  V  A  A  H  E  F   217

GGCCACGTGCTGGGGCTGCAGCACACAACAGCAGCCAAGGCCCTGATGTCCGCCTTCTAC   720
 G  H  V  L  G  L  Q  H  T  T  A  A  K  A  L  M  S  A  F  Y   237

ACCTTTCGCTACCCACTGAGTCTCAGCCCAGATGACTGCAGGGGCGTTCAACACCTATAT   780
 T  F  R  Y  P  L  S  L  S  P  D  D  C  R  G  V  Q  H  L  Y   257

GGCCAGCCCTGGCCCACTGTCACCTCCAGGACCCCAGCCCTGGGCCCCCAGGCTGGGATA   840
 G  Q  P  W  P  T  V  T  S  R  T  P  A  L  G  P  Q  A  G  I   277

GACACCAATGAGATTGCACCGCTGGAGCCAGACGCCCCGCCAGATGCCTGTGAGGCCTCC   900
 D  T  N  E  I  A  P  L  E  P  D  A  P  P  D  A  C  E  A  S   297
```

FIG.2A

```
TTTGACGCGGTCTCCACCATCCGAGGCGAGCTCTTTTTCTTCAAAGCGGGCTTTGTGTGG  960
 F   D   A   V   S   T   I   R   G   E   L   F   F   F   K   A   G   F   V   W   317

CGCCTCCGTGGGGGCCAGCTGCAGCCCGGCTACCCAGCATTGGCCTCTCGCCACTGGCAG 1020
 R   L   R   G   G   Q   L   Q   P   G   Y   P   A   L   A   S   R   H   W   Q   337

GGACTGCCCAGCCCTGTGGACGCTGCCTTCGAGGATGCCCAGGGCCACATTTGGTTCTTC 1080
 G   L   P   S   P   V   D   A   A   F   E   D   A   Q   G   H   I   W   F   F   357

CAAGGTGCTCAGTACTGGGTGTACGACGGTGAAAAGCCAGTCCTGGGCCCCGCACCCCTC 1140
 Q   G   A   Q   Y   W   V   Y   D   G   E   K   P   V   L   G   P   A   P   L   377

ACCGAGCTGGGCCTGGTGAGGTTCCCGGTCCATGCTGCCTTGGTCTGGGGTCCCGAGAAG 1200
 T   E   L   G   L   V   R   F   P   V   H   A   A   L   V   W   G   P   E   K   397

AACAAGATCTACTTCTTCCGAGGCAGGGACTACTGGCGTTTCCACCCCAGCACCCGGCGT 1260
 N   K   I   Y   F   F   R   G   R   D   Y   W   R   F   H   P   S   T   R   R   417

GTAGACAGTCCCGTGCCCCGCAGGGCCACTGACTGGAGAGGGGTGCCCTCTGAGATCGAC 1320
 V   D   S   P   V   P   R   R   A   T   D   W   R   G   V   P   S   E   I   D   437

GCTGCCTTCCAGGATGCTGATGGCTATGCCTACTTCCTGCGCGGCCGCCTCTACTGGAAG 1380
 A   A   F   Q   D   A   D   G   Y   A   Y   F   L   R   G   R   L   Y   W   K   457

TTTGACCCTGTGAAGGTGAAGGCTCTGGAAGGCTTCCCCCGTCTCGTGGGTCCTGACTTC 1440
 F   D   P   V   K   V   K   A   L   E   G   F   P   R   L   V   G   P   D   F   477

TTTGGCTGTGCCGAGCCTGCCAACACTTTCCTCTGACCATGGCTTGGATGCCCTCAGGGG 1500
 F   G   C   A   E   P   A   N   T   F   L   -                                    488

TGCTGACCCCTGCCAGGCCACGAATATCAGGCTAGAGACCCATGGCCATCTTTGTGGCTG 1560
TGGGCACCAGGCATGGGACTGAGCCCATGTCTCCTGCAGGGGGATGGGGTGGGGTACAAC 1620
CACCATGACAACTGCCGGGAGGGCCACGCAGGTCGTGGTCACCTGCCAGCGACTGTCTCA 1680
GACTGGGCAGGGAGGCTTTGGCATGACTTAAGAGGAAGGGCAGTCTTGGGACCCGCTATG 1740
CAGGTCCTGGCAAACCTGGCTGCCCTGTCTCATCCCTGTCCCTCAGGGTAGCACCATGGC 1800
AGGACTGGGGAACTGGAGTGTCCTTGCTGTATCCCTGTTGTGAGGTTCCTTCCAGGGGC 1860
TGGCACTGAAGCAAGGGTGCTGGGGCCCCATGGCCTTCAGCCCTGGCTGAGCAACTGGGC 1920
TGTAGGGCAGGGCCACTTCCTGAGGTCAGGTCTTGGTAGGTGCCTGCATCTGTCTGCCTT 1980
CTGGCTGACAATCCTGGAAATCTGTTCTCCAGAATCCAGGCCAAAAAGTTCACAGTCAAA 2040
TGGGGAGGGGTATTCTTCATGCAGGAGACCCCAGGCCCTGGAGGCTGCAACATACCTCAA 2100
TCCTGTCCCAGGCCGGATCCTCCTGAAGCCCTTTTCGCAGCACTGCTATCCTCCAAAGCC 2160
ATTGTAAATGTGTGTACAGTGTGTATAAACCTTCTTCTTCTTTTTTTTTTTTAAACTGAG 2220
GATTGTCATTAAACACAGTTGTTTTCTAAAAAAAA
```

FIG.2B

```
STROMELYSIN3   MAPAAWLR----SAAARALLPPMLLLLLQPPPLLAR------ALPPDVHHLHAERRGPQP    50
STROMELYSIN1   MKSLPILLLLCVAVCSAYPLDGAARGEDTSMNLVQKYLENYDLEKDVKQFV-RRKDSGP    59
STROMELYSIN2   MMHLAFLVLLCLPVCSAYPLSGAAKEEDSNKDLAQQYLEKYYNLEKDVKQF--RRKDSNL   58
COLLAGENASE1   MHSFPPLLLLLFWGVVSHSFPATLETQEQDVDLVQKYLEKYYNLKNDGRQVE-KRRNSGP    59
                  *                                 *        **    *    **

STROMELYSIN3   WHAALPSSP---APAPATQEAPRPASSLRPPRCGVPDPSDGLSARNRQKRFVLSGG--RW  105
STROMELYSIN1   VVKKIREMQKFLGLEVTGKLDSDTLEVMRKPRCGVPDVGH-----------FRTFPGIPKW  109
STROMELYSIN2   IVKKIQGMQKFLGLEVTGKLDTDTILEVMRKPRCGVPDVGH-----------FSSFPGMPKW  108
COLLAGENASE1   VVEKLKQMQEFFGLKVTGKPDAETLKVMKQPRCGVPDVAQ-----------FVLTEGNPRW  109
                                          *  ******                       *

STROMELYSIN3   EKTDLTYRILRFPWQLVQEQVRQTMAEALKVWSDVTPLTFTEVHEGRADIMIDFARYWHG  165
STROMELYSIN1   RKTHLTYRIVNYTPDLPKDAVDSAVEKALKVWEEVTPLTFSRLYEGEADIMISFAVREHG  169
STROMELYSIN2   RKTHLTYRIVNYTPDLPRDAVDSAIEKALKVWEEVTPLTFSRLYEGEADIMISFAVKEHG  168
COLLAGENASE1   EQTHLTYRIENYTPDLPRADVDHAIEKAFQLWSNVTPLTFTKVSEGQADIMISFVRGDHR  169
                 ***  *****  *****    *   **  * * ****** **  * *****     *
```

FIG.3A

```
STROMELYSIN3   DDLPFDGPGGILAHAFFPKTHREGDVHFDYDETWTIGDDQGTDLLQVAAHEFGHVLGLQH      225
STROMELYSIN1   DFYPFDGPGNVLAHAYAPGPGINGDAHFDDDEQWT-KDTTGTNLFLVAAHEIGHSLGLFH      228
STROMELYSIN2   DFYSFDGPGHSLAHAYPPGPGLYGDIHFDDDEKWT-EDASGTNLFLVAAHELGHSLGLFH      227
COLLAGENASE1   DNSPFDGPGGNLAHAFQPGPGIGGDAHFDEHERWT-NNFTEYNLHRVAAHELGHSLGLSH      228
               *   ***** ****      *    ** ***  *  **    *   ***** ** *** *

STROMELYSIN3   TTAAKALMSAFYTFRYPLS---LSPDDCRGVQHLYGQPWPTVTSRTPALGPQAGIDTNEI     282
STROMELYSIN1   SANTEALMYPLYHSLTDLTRFRLSQDDINGIQSLYGPP---PDSPETPLVPTEPV----     280
STROMELYSIN2   SANTEALMYPLYNSFTELAQFRLSQDDVNGIQSLYGPP---PASTEEPLVPTKSV----     279
COLLAGENASE1   STDIGALMYPSYTFSGDV---QLAQDDIDGIQAIYGRS---QNPVQ-------------     268
                 *   **       *       *  *   **  **         *  *   *

STROMELYSIN3   APLEPDAPPDACEA--SFDAVSTIRGELFFFKAGFVWRLRGGQLQPGYPALASRHWQGLP     340
STROMELYSIN1   -PPEPGTPAN-CDPALSFDAVSTLRGEILIFKDRHFWRKSLRKLEPELH-LISSFWPSLP     337
STROMELYSIN2   -PSGSEMPAK-CDPALSFDAISTLRGEYLFFKDRYFWRRSHWNPEPEFH-LISAFWPSLP     336
COLLAGENASE1   -PIGPQTPKA-CDSKLTFDAITTIRGEVMFFKDRFYMRTNPFYPEVELN-FISVFWPQLP     325
                  *           * ***   *** * * *   *          *     * * **
```

FIG.3B

```
STROMELYSIN3   SPVDAAFE-DAQGHIWFFQGAQYWVYDGEKPVLG--PAPLTELGLVRFPVH-AALVWGPE   396
STROMELYSIN1   SGVDAAYEVTSKDLVFIFKGNQFWAIRGNEVRAGYPRGIHT-LGFPPTVRKIDAAISDKE   396
STROMELYSIN2   SYLDAAYEVNSRDTVFIFKGNEFWAIRGNEVQAGYPRGIHT-LGFPPTIRKIDAAVSDKE   395
COLLAGENASE1   NGLEAAYEFADRDEVRFFKGNKYWAVQGQNVLHGYPKDIYSSFGFPRTVKHIDAALSEEN   385
                 **          **                **           *     *

STROMELYSIN3   KNKIYFFRGRDYWRFHPSTRRVDSPVPRR-ATDWRGVPSEIDAAFQDADGYAYFLRGRLY   455
STROMELYSIN1   KNKTYFFVEDKYWRFDEKRNSMEPGFPKQIAEDFPGIDSKIDAVFEEF-GFFYFFTGSSQ   455
STROMELYSIN2   KKKTYFFAADKYWRFDENSQSMEQGFPRLIADDFPGVEPKVDAVLQAF-GFFYFFSGSSQ   454
COLLAGENASE1   TGKTYFFVANKYWRYDEYKRSMDPGYPKMIAHDFPGIGHKVDAVFMKD-GFFYFFHGTRQ   444
                 * ***      ***                      **      **   ** **  *

STROMELYSIN3   WKFDPVKVKALEGFPRLVGPDFFGCAEPANTFL   488
STROMELYSIN1   LEFDPNAKKVTHT---LKSNSWLNC--------   477
STROMELYSIN2   FEFDPNARMVTHI---LKSNSWLHC--------   476
COLLAGENASE1   YKFDPKTKRILTL---QKANSWFNCRKN-----   461
                ***
```

FIG. 3C

SIMILARITY WITH ST3

ST3: P (97) | ENZ (488)
ST1: P 16% (99) | 40% (477)
ST2: 16% (98) | 38% (476)
CO1: 17% (99) | 36% (461)

SIMILARITY WITH ST1

ST1: P (99) | ENZ (477)
ST2: 75% (98) | 79% (476)
CO1: 48% (99) | 53% (461)

F I G. 3D

```
CCCGGGGCGGATGGCACGGGCCGCCTGTCTCCTCCGCGCGATTTCGGGGTGCCTCCTGCT   60
             M  A  R  A  A  C  L  L  R  A  I  S  G  C  L  L  L   17
CCCGCTGCCTCTGCTGCTCCTGTTGCTGCTGCTCCTGCCGTCGCCGCTGATGGCCCGGGC  120
 P  L  P  L  L  L  L  L  L  L  L  P  S  P  L  M  A  R  A        37
CAGGCCACCGGAGAGTCACCGTCATCACCCTGTGAAGAAAGGGCCTCGGCTCCTGCATGC  180
  R  P  P  E  S  H  R  H  H  P  V  K  K  G  P  R  L  L  H  A   57
AGCTCTGCCTAATACCTTGACATCTGTCCCCGCGTCTCATTGGGTCCCTAGTCCTGCCGG  240
  A  L  P  N  T  L  T  S  V  P  A  S  H  W  V  P  S  P  A  G   77
TAGCTCCAGGCCTCTACGATGTGGTGTGCCCGACCTGCCTGATGTACTGAATGCCCGGAA  300
  S  S  R  P  L  R  C  G  V  P  D  L  P  D  V  L  N  A  R  N   97
CCGACAGAAGCGCTTCGTCCTGTCAGGAGGACGCTGGGAGAAGACAGACCTCACCTATAG  360
  R  Q  K  R  F  V  L  S  G  G  R  W  E  K  T  D  L  T  Y  R  117
GATCCTCCGGTTCCCATGGCAGCTTGTAAGGGAGCAAGTCCGGCAGACAGTGGCAGAGGC  420
  I  L  R  F  P  W  Q  L  V  R  E  Q  V  R  Q  T  V  A  E  A  139
CCTCCAGGTATGGAGTGAAGTGACCCCACTCACTTTCACTGAGGTGCACGAGGGACGCGC  480
  L  Q  V  W  S  E  V  T  P  L  T  F  T  E  V  H  E  G  R  A  157
TGACATCATGATCGACTTCGCAAGGTACTGGGATGGTGACAACTTGCCGTTTGACGGGCC  540
  D  I  M  I  D  F  A  R  Y  W  D  G  D  N  L  P  F  D  G  P  177
TGGGGGCATCCTGGCCCATGGCTTCTTCCCTAAGACCCACCGAGAAGGGGATGTCCACTT  600
  G  G  I  L  A  H  G  F  F  P  K  T  H  R  E  G  D  V  H  F  197
TGACTATGATGAAACTTGGACTATTGGGGACAACCAGGGAACTGACCTGCTGCAAGTGGC  660
  D  Y  D  E  T  W  T  I  G  D  N  Q  G  T  D  L  L  Q  V  A  217
GGCTCATGAATTTGGCCATGTTCTGGGGCTACAACACACCACAGCAGCTAAGGCCCTCAT  720
  A  H  E  F  G  H  V  L  G  L  Q  H  T  T  A  A  K  A  L  M  237
GTCCCCTTTCTACACCTTCCGCTACCCTCTGAGCCTTAGCCCAGATGACCGAAGGGGCAT  780
  S  P  F  Y  T  F  R  Y  P  L  S  L  S  P  D  D  R  R  G  I  257
CCAGCACCTCTATGGGCGGCCCCAGATGACCCCCACCTCCCCCGCCCCAACTTTGAGCTC  840
  Q  H  L  Y  G  R  P  Q  M  T  P  T  S  P  A  P  T  L  S  S  277
CCAGGCTGGGACAGATACCAATGAGATTGCACTGCTGGAGCCGGAAACCCCGCCAGATGT  900
  Q  A  G  T  D  T  N  E  I  A  L  L  E  P  E  T  P  P  D  V  297
CTGTGAGACTTCCTTCGACGCGGTTTCCACCATCCGAGGAGAGCTCTTCTTCTTCAAGGC  960
  C  E  T  S  F  D  A  V  S  T  I  R  G  E  L  F  F  F  K  A  317
AGGCTTTGTGTGGAGGCTGCGCAGTGGGCGACTGCAGCCCGGGTATCCTGCTTTGGCCTC 1020
  G  F  V  W  R  L  R  S  G  R  L  Q  P  G  Y  P  A  L  A  S  337
```

FIG. 7A

```
TCGGCACTGGCAAGGACTGCCCAGCCCTGTGGATGCAGCTTTTGAGGATGCCCAGGGCCA    1080
  R  H  W  Q  G  L  P  S  P  V  D  A  A  F  E  D  A  Q  G  Q    357
GATTTGGTTCTTCCAAGGTGCTCAGTACTGGGTATATGATGGTGAGAAGCCAGTCCTAGG    1140
  I  W  F  F  Q  G  A  Q  Y  W  V  Y  D  G  E  K  P  V  L  G    377
CCCTGCACCACTCTCCAAGCTGGGCCTGCAAGGGTCCCCAGTTCATGCCGCCTTGGTCTG    1200
  P  A  P  L  S  K  L  G  L  Q  G  S  P  V  H  A  A  L  V  W    397
GGGTCCTGAGAAGAACAAGATCTACTTCTTCCGAGGTGGAGACTATTGGCGTTTCCACCC    1260
  G  P  E  K  N  K  I  Y  F  F  R  G  G  D  Y  W  R  F  H  P    417
CAGAACCCAGCGAGTGGACAATCCCGTGCCCCGGCGCTCCACTGACTGGCGAGGGGTACC    1320
  R  T  Q  R  V  D  N  P  V  P  R  R  S  T  D  W  R  G  V  P    437
TTCTGAGATTGATGCTGCCTTCCAGGATGCTGAGGGCTATGCCTACTTCCTTCGTGGCCA    1380
  S  E  I  D  A  A  F  Q  D  A  E  G  Y  A  Y  F  L  R  G  H    457
TCTCTACTGGAAGTTTGATCCCGTGAAGGTGAAGGTCCTAGAAGGCTTTCCTCGCCCCGT    1440
  L  Y  W  K  F  D  P  V  K  V  K  V  L  E  G  F  P  R  P  V    477
AGGTCCTGACTTCTTTGACTGTGCTGAGCCTGCCAATACTTTCCGCTGACAACACTTTGG    1500
  G  P  D  F  F  D  C  A  E  P  A  N  T  F  R  -                492
ATGCATTCAGGGGTACTGACTCCTGCCAGGGCACTTAGATCATGTAAGAGACCCACAGCC    1560
ATATCTGTGGCTCTGGCTTCAGGCATGGGACAGACAGGGCCTATGTCTCCTCAGGGGAGT    1620
GGGTTGGGGTGCAGCCACTGTTTGTAGGAACGACCATGCTGTCATGTCACCTGCCAACAA    1680
TTGTCTCAGACTAGGCAAAGGCTTTGGTGTTACTTAAAAATAAGGGAGGTTTTGGGCTGG    1740
CAATATTTCAGCTACCAATAATCCACAGTCAGCCTGGTTGCCCAAGGTCTCCTATCTCTG    1800
TCCCTCAATGTAGAACCCCCACACAAACTCAGGAATCACCTGCAATGAGGTTCCTGTTGG    1860
GAGTGGTGTTGGTAATGAGATGCCCAGGGTACCATGCTGCCCCTGCTAAGCAACTGGACC    1920
AGTATCTTTCCTGGTAAGTCAGCTCTGGAGAGATAGTGAACTGATCATATTCTGGCAGGT    1980
GATTCAGACAAGTGCTTCCTGGAACTCAGGCCCCAAGGTACACAGCCAGCCAAGGAGGCA    2040
GCTGCTTCCTCCCAGAGACACGGAACCTCAAAGGCCCCACATACCTCACAGCCTTGCCCC    2100
AGGCCATTTCTTTCTGGGGCCCTCTTCCTAGCACAGGTACCCTCTAAGCCATGTACATGT    2160
GTATACAGTGTATAAAGACTTTTTTAAAAAAACAAAAAACCAAACCCCAAAAAAGCCAAG    2220
ACTGTCATTAAACATGAGTGTTTTCTAAAAAAAAAAAAAAA                       2260
```

FIG. 7B

BREAST CARCINOMAS

DUCTAL | LOBULAR | NORMAL BREAST

Kb     PRIMARY TUMORS 2.4 →                                ST3
1.5 →                                36B4

NODE METASTASES 2.4 →                                ST3
1.5 →                                36B4

FIG. 14B

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2256 base pairs
        ( B ) TYPE: nucleic acid
        ( C ) STRANDEDNESS: both
        ( D ) TOPOLOGY: linear ( i i ) MOLECULE TYPE: DNA (genomic)

( i x ) FEATURE:
        ( A ) NAME/KEY: CDS
        ( B ) LOCATION: 10..1473

( x i ) SEQUENCE DESCRIPTION: SEQ ID NO:1:

```
CCGGGGCGG ATG GCT CCG GCC GCC TGG CTC CGC AGC GCG GCC GCG CGC        48
          Met Ala Pro Ala Ala Trp Leu Arg Ser Ala Ala Ala Arg
           1               5                  10

GCC CTC CTG CCC CCG ATG CTG CTG CTG CTG CTC CAG CCG CCG CCG CTG      96
Ala Leu Leu Pro Pro Met Leu Leu Leu Leu Leu Gln Pro Pro Pro Leu
     15              20                  25

CTG GCC CGG GCT CTG CCG CCG GAC GTC CAC CAC CTC CAT GCC GAG AGG     144
Leu Ala Arg Ala Leu Pro Pro Asp Val His His Leu His Ala Glu Arg
 30              35                  40                      45

AGG GGG CCA CAG CCC TGG CAT GCA GCC CTG CCC AGT AGC CCG GCA CCT     192
Arg Gly Pro Gln Pro Trp His Ala Ala Leu Pro Ser Ser Pro Ala Pro
             50                  55                  60

GCC CCT GCC ACG CAG GAA GCC CCC CGG CCT GCC AGC AGC CTC AGG CCT     240
Ala Pro Ala Thr Gln Glu Ala Pro Arg Pro Ala Ser Ser Leu Arg Pro
         65                  70                  75

CCC CGC TGT GGC GTG CCC GAC CCA TCT GAT GGG CTG AGT GCC CGC AAC     288
Pro Arg Cys Gly Val Pro Asp Pro Ser Asp Gly Leu Ser Ala Arg Asn
             80                  85                  90

CGA CAG AAG AGG TTC GTG CTT TCT GGC GGG CGC TGG GAG AAG ACG GAC     336
Arg Gln Lys Arg Phe Val Leu Ser Gly Gly Arg Trp Glu Lys Thr Asp
         95                 100                 105

CTC ACC TAC AGG ATC CTT CGG TTC CCA TGG CAG TTG GTG CAG GAG CAG     384
Leu Thr Tyr Arg Ile Leu Arg Phe Pro Trp Gln Leu Val Gln Glu Gln
110                 115                 120                 125

GTG CGG CAG ACG ATG GCA GAG GCC CTA AAG GTA TGG AGC GAT GTG ACG     432
Val Arg Gln Thr Met Ala Glu Ala Leu Lys Val Trp Ser Asp Val Thr
                130                 135                 140

CCA CTC ACC TTT ACT GAG GTG CAC GAG GGC CGT GCT GAC ATC ATG ATC     480
Pro Leu Thr Phe Thr Glu Val His Glu Gly Arg Ala Asp Ile Met Ile
             145                 150                 155

GAC TTC GCC AGG TAC TGG CAT GGG GAC GAC CTG CCG TTT GAT GGG CCT     528
Asp Phe Ala Arg Tyr Trp His Gly Asp Asp Leu Pro Phe Asp Gly Pro
         160                 165                 170

GGG GGC ATC CTG GCC CAT GCC TTC TTC CCC AAG ACT CAC CGA GAA GGG     576
Gly Gly Ile Leu Ala His Ala Phe Phe Pro Lys Thr His Arg Glu Gly
         175                 180                 185

GAT GTC CAC TTC GAC TAT GAT GAG ACC TGG ACT ATC GGG GAT GAC CAG     624
Asp Val His Phe Asp Tyr Asp Glu Thr Trp Thr Ile Gly Asp Asp Gln
190                 195                 200                 205

GGC ACA GAC CTG CTG CAG GTG GCA GCC CAT GAA TTT GGC CAC GTG CTG     672
Gly Thr Asp Leu Leu Gln Val Ala Ala His Glu Phe Gly His Val Leu
                210                 215                 220
```

| | | | | | | | | | | | | | | | | |
|---|---|---|---|---|---|---|---|---|---|---|---|---|---|---|---|---|
| GGG | CTG | CAG | CAC | ACA | ACA | GCA | GCC | AAG | GCC | CTG | ATG | TCC | GCC | TTC | TAC | 720 |
| Gly | Leu | Gln | His | Thr | Thr | Ala | Ala | Lys | Ala | Leu | Met | Ser | Ala | Phe | Tyr | |
| | | | 225 | | | | | 230 | | | | | 235 | | | |
| ACC | TTT | CGC | TAC | CCA | CTG | AGT | CTC | AGC | CCA | GAT | GAC | TGC | AGG | GGC | GTT | 768 |
| Thr | Phe | Arg | Tyr | Pro | Leu | Ser | Leu | Ser | Pro | Asp | Asp | Cys | Arg | Gly | Val | |
| | | | 240 | | | | | 245 | | | | | 250 | | | |
| CAA | CAC | CTA | TAT | GGC | CAG | CCC | TGG | CCC | ACT | GTC | ACC | TCC | AGG | ACC | CCA | 816 |
| Gln | His | Leu | Tyr | Gly | Gln | Pro | Trp | Pro | Thr | Val | Thr | Ser | Arg | Thr | Pro | |
| | 255 | | | | 260 | | | | | 265 | | | | | | |
| GCC | CTG | GGC | CCC | CAG | GCT | GGG | ATA | GAC | ACC | AAT | GAG | ATT | GCA | CCG | CTG | 864 |
| Ala | Leu | Gly | Pro | Gln | Ala | Gly | Ile | Asp | Thr | Asn | Glu | Ile | Ala | Pro | Leu | |
| 270 | | | | | 275 | | | | | 280 | | | | | 285 | |
| GAG | CCA | GAC | GCC | CCG | CCA | GAT | GCC | TGT | GAG | GCC | TCC | TTT | GAC | GCG | GTC | 912 |
| Glu | Pro | Asp | Ala | Pro | Pro | Asp | Ala | Cys | Glu | Ala | Ser | Phe | Asp | Ala | Val | |
| | | | | 290 | | | | | 295 | | | | | 300 | | |
| TCC | ACC | ATC | CGA | GGC | GAG | CTC | TTT | TTC | TTC | AAA | GCG | GGC | TTT | GTG | TGG | 960 |
| Ser | Thr | Ile | Arg | Gly | Glu | Leu | Phe | Phe | Phe | Lys | Ala | Gly | Phe | Val | Trp | |
| | | | 305 | | | | | 310 | | | | | 315 | | | |
| CGC | CTC | CGT | GGG | GGC | CAG | CTG | CAG | CCC | GGC | TAC | CCA | GCA | TTG | GCC | TCT | 1008 |
| Arg | Leu | Arg | Gly | Gly | Gln | Leu | Gln | Pro | Gly | Tyr | Pro | Ala | Leu | Ala | Ser | |
| | | 320 | | | | | 325 | | | | | 330 | | | | |
| CGC | CAC | TGG | CAG | GGA | CTG | CCC | AGC | CCT | GTG | GAC | GCT | GCC | TTC | GAG | GAT | 1056 |
| Arg | His | Trp | Gln | Gly | Leu | Pro | Ser | Pro | Val | Asp | Ala | Ala | Phe | Glu | Asp | |
| | 335 | | | | | 340 | | | | | 345 | | | | | |
| GCC | CAG | GGC | CAC | ATT | TGG | TTC | TTC | CAA | GGT | GCT | CAG | TAC | TGG | GTG | TAC | 1104 |
| Ala | Gln | Gly | His | Ile | Trp | Phe | Phe | Gln | Gly | Ala | Gln | Tyr | Trp | Val | Tyr | |
| 350 | | | | | 355 | | | | | 360 | | | | | 365 | |
| GAC | GGT | GAA | AAG | CCA | GTC | CTG | GGC | CCC | GCA | CCC | CTC | ACC | GAG | CTG | GGC | 1152 |
| Asp | Gly | Glu | Lys | Pro | Val | Leu | Gly | Pro | Ala | Pro | Leu | Thr | Glu | Leu | Gly | |
| | | | | 370 | | | | | 375 | | | | | 380 | | |
| CTG | GTG | AGG | TTC | CCG | GTC | CAT | GCT | GCC | TTG | GTC | TGG | GGT | CCC | GAG | AAG | 1200 |
| Leu | Val | Arg | Phe | Pro | Val | His | Ala | Ala | Leu | Val | Trp | Gly | Pro | Glu | Lys | |
| | | | 385 | | | | | 390 | | | | | 395 | | | |
| AAC | AAG | ATC | TAC | TTC | TTC | CGA | GGC | AGG | GAC | TAC | TGG | CGT | TTC | CAC | CCC | 1248 |
| Asn | Lys | Ile | Tyr | Phe | Phe | Arg | Gly | Arg | Asp | Tyr | Trp | Arg | Phe | His | Pro | |
| | | 400 | | | | | 405 | | | | | 410 | | | | |
| AGC | ACC | CGG | CGT | GTA | GAC | AGT | CCC | GTG | CCC | CGC | AGG | GCC | ACT | GAC | TGG | 1296 |
| Ser | Thr | Arg | Arg | Val | Asp | Ser | Pro | Val | Pro | Arg | Arg | Ala | Thr | Asp | Trp | |
| | 415 | | | | | 420 | | | | | 425 | | | | | |
| AGA | GGG | GTG | CCC | TCT | GAG | ATC | GAC | GCT | GCC | TTC | CAG | GAT | GCT | GAT | GGC | 1344 |
| Arg | Gly | Val | Pro | Ser | Glu | Ile | Asp | Ala | Ala | Phe | Gln | Asp | Ala | Asp | Gly | |
| 430 | | | | | 435 | | | | | 440 | | | | | 445 | |
| TAT | GCC | TAC | TTC | CTG | CGC | GGC | CGC | CTC | TAC | TGG | AAG | TTT | GAC | CCT | GTG | 1392 |
| Tyr | Ala | Tyr | Phe | Leu | Arg | Gly | Arg | Leu | Tyr | Trp | Lys | Phe | Asp | Pro | Val | |
| | | | | 450 | | | | | 455 | | | | | 460 | | |
| AAG | GTG | AAG | GCT | CTG | GAA | GGC | TTC | CCC | CGT | CTC | GTG | GGT | CCT | GAC | TTC | 1440 |
| Lys | Val | Lys | Ala | Leu | Glu | Gly | Phe | Pro | Arg | Leu | Val | Gly | Pro | Asp | Phe | |
| | | | 465 | | | | | 470 | | | | | 475 | | | |
| TTT | GGC | TGT | GCC | GAG | CCT | GCC | AAC | ACT | TTC | CTC | TGACCATGGC | TTGGATGCCC | | | | 1493 |
| Phe | Gly | Cys | Ala | Glu | Pro | Ala | Asn | Thr | Phe | Leu | | | | | | |
| | | 480 | | | | | 485 | | | | | | | | | |

| | | | | |
|---|---|---|---|---|
| TCAGGGGTGC | TGACCCCTGC | CAGGCCACGA | ATATCAGGCT | AGAGACCCAT GGCCATCTTT | 1553 |
| GTGGCTGTGG | GCACCAGGCA | TGGGACTGAG | CCCATGTCTC | CTGCAGGGGG ATGGGGTGGG | 1613 |
| GTACAACCAC | CATGACAACT | GCCGGGAGGG | CCACGCAGGT | CGTGGTCACC TGCCAGCGAC | 1673 |
| TGTCTCAGAC | TGGGCAGGGA | GGCTTTGGCA | TGACTTAAGA | GGAAGGGCAG TCTTGGGACC | 1733 |
| CGCTATGCAG | GTCCTGGCAA | ACCTGGCTGC | CCTGTCTCAT | CCCTGTCCCT CAGGGTAGCA | 1793 |
| CCATGGCAGG | ACTGGGGGAA | CTGGAGTGTC | CTTGCTGTAT | CCCTGTTGTG AGGTTCCTTC | 1853 |

-continued

| | | | | | |
|---|---|---|---|---|---|
| CAGGGGCTGG | CACTGAAGCA | AGGGTGCTGG | GGCCCCATGG | CCTTCAGCCC | TGGCTGAGCA | 1913
| ACTGGGCTGT | AGGGCAGGGC | CACTTCCTGA | GGTCAGGTCT | TGGTAGGTGC | CTGCATCTGT | 1973
| CTGCCTTCTG | GCTGACAATC | CTGGAAATCT | GTTCTCCAGA | ATCCAGGCCA | AAAAGTTCAC | 2033
| AGTCAAATGG | GGAGGGGTAT | TCTTCATGCA | GGAGACCCCA | GGCCCTGGAG | GCTGCAACAT | 2093
| ACCTCAATCC | TGTCCCAGGC | CGGATCCTCC | TGAAGCCCTT | TTCGCAGCAC | TGCTATCCTC | 2153
| CAAAGCCATT | GTAAATGTGT | GTACAGTGTG | TATAAACCTT | CTTCTTCTTT | TTTTTTTTTA | 2213
| AACTGAGGAT | TGTCATTAAA | CACAGTTGTT | TTCTAAAAAA | AAA | | 2256

( 2 ) INFORMATION FOR SEQ ID NO:2:

( i ) SEQUENCE CHARACTERISTICS:
        ( A ) LENGTH: 488 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Pro Ala Ala Trp Leu Arg Ser Ala Ala Arg Ala Leu Leu
 1               5                  10                  15

Pro Pro Met Leu Leu Leu Leu Leu Gln Pro Pro Pro Leu Leu Ala Arg
            20                  25                  30

Ala Leu Pro Pro Asp Val His His Leu His Ala Glu Arg Arg Gly Pro
            35                  40                  45

Gln Pro Trp His Ala Ala Leu Pro Ser Ser Pro Ala Pro Ala Pro Ala
    50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg Phe Val Leu Ser Gly Gly Arg Trp Glu Lys Thr Asp Leu Thr Tyr
                100                 105                 110

Arg Ile Leu Arg Phe Pro Trp Gln Leu Val Gln Glu Gln Val Arg Gln
            115                 120                 125

Thr Met Ala Glu Ala Leu Lys Val Trp Ser Asp Val Thr Pro Leu Thr
130                 135                 140

Phe Thr Glu Val His Glu Gly Arg Ala Asp Ile Met Ile Asp Phe Ala
145                 150                     155                 160

Arg Tyr Trp His Gly Asp Asp Leu Pro Phe Asp Gly Pro Gly Gly Ile
                165                 170                 175

Leu Ala His Ala Phe Phe Pro Lys Thr His Arg Glu Gly Asp Val His
            180                 185                 190

Phe Asp Tyr Asp Glu Thr Trp Thr Ile Gly Asp Asp Gln Gly Thr Asp
        195                 200                 205

Leu Leu Gln Val Ala Ala His Glu Phe Gly His Val Leu Gly Leu Gln
210                 215                 220

His Thr Thr Ala Ala Lys Ala Leu Met Ser Ala Phe Tyr Thr Phe Arg
225                 230                 235                 240

Tyr Pro Leu Ser Leu Ser Pro Asp Asp Cys Arg Gly Val Gln His Leu
                245                 250                 255

Tyr Gly Gln Pro Trp Pro Thr Val Thr Ser Arg Thr Pro Ala Leu Gly
            260                 265                 270

Pro Gln Ala Gly Ile Asp Thr Asn Glu Ile Ala Pro Leu Glu Pro Asp
        275                 280                 285
```

| | | | | | | | | | | | | | | |
|---|---|---|---|---|---|---|---|---|---|---|---|---|---|---|
| Ala | Pro | Pro | Asp | Ala | Cys | Glu | Ala | Ser | Phe | Asp | Ala | Val | Ser | Thr | Ile |
| | 290 | | | | 295 | | | | | 300 | | | | | |
| Arg | Gly | Glu | Leu | Phe | Phe | Phe | Lys | Ala | Gly | Phe | Val | Trp | Arg | Leu | Arg |
| 305 | | | | | 310 | | | | | 315 | | | | | 320 |
| Gly | Gly | Gln | Leu | Gln | Pro | Gly | Tyr | Pro | Ala | Leu | Ala | Ser | Arg | His | Trp |
| | | | | 325 | | | | | 330 | | | | | 335 | |
| Gln | Gly | Leu | Pro | Ser | Pro | Val | Asp | Ala | Ala | Phe | Glu | Asp | Ala | Gln | Gly |
| | | | 340 | | | | | 345 | | | | | 350 | | |
| His | Ile | Trp | Phe | Phe | Gln | Gly | Ala | Gln | Tyr | Trp | Val | Tyr | Asp | Gly | Glu |
| | | 355 | | | | | 360 | | | | | 365 | | | |
| Lys | Pro | Val | Leu | Gly | Pro | Ala | Pro | Leu | Thr | Glu | Leu | Gly | Leu | Val | Arg |
| | 370 | | | | | 375 | | | | | 380 | | | | |
| Phe | Pro | Val | His | Ala | Ala | Leu | Val | Trp | Gly | Pro | Glu | Lys | Asn | Lys | Ile |
| 385 | | | | | 390 | | | | | 395 | | | | | 400 |
| Tyr | Phe | Phe | Arg | Gly | Arg | Asp | Tyr | Trp | Arg | Phe | His | Pro | Ser | Thr | Arg |
| | | | | 405 | | | | | 410 | | | | | 415 | |
| Arg | Val | Asp | Ser | Pro | Val | Pro | Arg | Arg | Ala | Thr | Asp | Trp | Arg | Gly | Val |
| | | | 420 | | | | | 425 | | | | | 430 | | |
| Pro | Ser | Glu | Ile | Asp | Ala | Ala | Phe | Gln | Asp | Ala | Asp | Gly | Tyr | Ala | Tyr |
| | | 435 | | | | | 440 | | | | | 445 | | | |
| Phe | Leu | Arg | Gly | Arg | Leu | Tyr | Trp | Lys | Phe | Asp | Pro | Val | Lys | Val | Lys |
| | 450 | | | | | 455 | | | | | 460 | | | | |
| Ala | Leu | Glu | Gly | Phe | Pro | Arg | Leu | Val | Gly | Pro | Asp | Phe | Phe | Gly | Cys |
| 465 | | | | | 470 | | | | | 475 | | | | | 480 |
| Ala | Glu | Pro | Ala | Asn | Thr | Phe | Leu | | | | | | | | |
| | | | | 485 | | | | | | | | | | | |

( 2 ) INFORMATION FOR SEQ ID NO:3:

( i ) SEQUENCE CHARACTERISTICS:
  ( A ) LENGTH: 2260 base pairs
  ( B ) TYPE: nucleic acid
  ( C ) STRANDEDNESS: both
  ( D ) TOPOLOGY: linear ( i i ) MOLECULE TYPE: DNA (genomic)

( i x ) FEATURE:
  ( A ) NAME/KEY: CDS
  ( B ) LOCATION: 11..1486

( x i ) SEQUENCE DESCRIPTION: SEQ ID NO:3:

| | | | | | | | | | | | | | | |
|---|---|---|---|---|---|---|---|---|---|---|---|---|---|---|
| CCCGGGGCGG | ATG | GCA | CGG | GCC | GCC | TGT | CTC | CTC | CGC | GCG | ATT | TCG | GGG | 49 |
| | Met | Ala | Arg | Ala | Ala | Cys | Leu | Leu | Arg | Ala | Ile | Ser | Gly | |
| | 1 | | | | 5 | | | | | 10 | | | | |
| TGC | CTC | CTG | CTC | CCG | CTG | CCT | CTG | CTC | CTG | TTG | CTG | CTG | CTC | CTG | 97 |
| Cys | Leu | Leu | Leu | Pro | Leu | Pro | Leu | Leu | Leu | Leu | Leu | Leu | Leu | Leu | |
| | 15 | | | | 20 | | | | | 25 | | | | | |
| CCG | TCG | CCG | CTG | ATG | GCC | CGG | GCC | AGG | CCA | CCG | GAG | AGT | CAC | CGT | CAT | 145 |
| Pro | Ser | Pro | Leu | Met | Ala | Arg | Ala | Arg | Pro | Pro | Glu | Ser | His | Arg | His |
| 30 | | | | | 35 | | | | | 40 | | | | | 45 |
| CAC | CCT | GTG | AAG | AAA | GGG | CCT | CGG | CTC | CTG | CAT | GCA | GCT | CTG | CCT | AAT | 193 |
| His | Pro | Val | Lys | Lys | Gly | Pro | Arg | Leu | Leu | His | Ala | Ala | Leu | Pro | Asn |
| | | | | 50 | | | | | 55 | | | | | 60 | |
| ACC | TTG | ACA | TCT | GTC | CCC | GCG | TCT | CAT | TGG | GTC | CCT | AGT | CCT | GCC | GGT | 241 |
| Thr | Leu | Thr | Ser | Val | Pro | Ala | Ser | His | Trp | Val | Pro | Ser | Pro | Ala | Gly |
| | | | 65 | | | | | 70 | | | | | 75 | | |
| AGC | TCC | AGG | CCT | CTA | CGA | TGT | GGT | GTG | CCC | GAC | CTG | CCT | GAT | GTA | CTG | 289 |
| Ser | Ser | Arg | Pro | Leu | Arg | Cys | Gly | Val | Pro | Asp | Leu | Pro | Asp | Val | Leu |
| | | 80 | | | | | 85 | | | | | 90 | | | |

| | | | | | | | | | | | | | | | | |
|---|---|---|---|---|---|---|---|---|---|---|---|---|---|---|---|---|
| AAT | GCC | CGG | AAC | CGA | CAG | AAG | CGC | TTC | GTC | CTG | TCA | GGA | GGA | CGC | TGG | 337 |
| Asn | Ala | Arg | Asn | Arg | Gln | Lys | Arg | Phe | Val | Leu | Ser | Gly | Gly | Arg | Trp | |
| | 95 | | | | 100 | | | | | 105 | | | | | | |
| GAG | AAG | ACA | GAC | CTC | ACC | TAT | AGG | ATC | CTC | CGG | TTC | CCA | TGG | CAG | CTT | 385 |
| Glu | Lys | Thr | Asp | Leu | Thr | Tyr | Arg | Ile | Leu | Arg | Phe | Pro | Trp | Gln | Leu | |
| 110 | | | | | 115 | | | | | 120 | | | | | 125 | |
| GTA | AGG | GAG | CAA | GTC | CGG | CAG | ACA | GTG | GCA | GAG | GCC | CTC | CAG | GTA | TGG | 433 |
| Val | Arg | Glu | Gln | Val | Arg | Gln | Thr | Val | Ala | Glu | Ala | Leu | Gln | Val | Trp | |
| | | | | 130 | | | | | 135 | | | | | 140 | | |
| AGT | GAA | GTG | ACC | CCA | CTC | ACT | TTC | ACT | GAG | GTG | CAC | GAG | GGA | CGC | GCT | 481 |
| Ser | Glu | Val | Thr | Pro | Leu | Thr | Phe | Thr | Glu | Val | His | Glu | Gly | Arg | Ala | |
| | | | 145 | | | | | 150 | | | | | 155 | | | |
| GAC | ATC | ATG | ATC | GAC | TTC | GCA | AGG | TAC | TGG | GAT | GGT | GAC | AAC | TTG | CCG | 529 |
| Asp | Ile | Met | Ile | Asp | Phe | Ala | Arg | Tyr | Trp | Asp | Gly | Asp | Asn | Leu | Pro | |
| | | | 160 | | | | 165 | | | | | 170 | | | | |
| TTT | GAC | GGG | CCT | GGG | GGC | ATC | CTG | GCC | CAT | GGC | TTC | TTC | CCT | AAG | ACC | 577 |
| Phe | Asp | Gly | Pro | Gly | Gly | Ile | Leu | Ala | His | Gly | Phe | Phe | Pro | Lys | Thr | |
| | 175 | | | | | 180 | | | | | 185 | | | | | |
| CAC | CGA | GAA | GGG | GAT | GTC | CAC | TTT | GAC | TAT | GAT | GAA | ACT | TGG | ACT | ATT | 625 |
| His | Arg | Glu | Gly | Asp | Val | His | Phe | Asp | Tyr | Asp | Glu | Thr | Trp | Thr | Ile | |
| 190 | | | | | 195 | | | | | 200 | | | | | 205 | |
| GGG | GAC | AAC | CAG | GGA | ACT | GAC | CTG | CTG | CAA | GTG | GCG | GCT | CAT | GAA | TTT | 673 |
| Gly | Asp | Asn | Gln | Gly | Thr | Asp | Leu | Leu | Gln | Val | Ala | Ala | His | Glu | Phe | |
| | | | | 210 | | | | | 215 | | | | | 220 | | |
| GGC | CAT | GTT | CTG | GGG | CTA | CAA | CAC | ACC | ACA | GCA | GCT | AAG | GCC | CTC | ATG | 721 |
| Gly | His | Val | Leu | Gly | Leu | Gln | His | Thr | Thr | Ala | Ala | Lys | Ala | Leu | Met | |
| | | | 225 | | | | | 230 | | | | | 235 | | | |
| TCC | CCT | TTC | TAC | ACC | TTC | CGC | TAC | CCT | CTG | AGC | CTT | AGC | CCA | GAT | GAC | 769 |
| Ser | Pro | Phe | Tyr | Thr | Phe | Arg | Tyr | Pro | Leu | Ser | Leu | Ser | Pro | Asp | Asp | |
| | | 240 | | | | | 245 | | | | | 250 | | | | |
| CGA | AGG | GGC | ATC | CAG | CAC | CTC | TAT | GGG | CGG | CCC | CAG | ATG | ACC | CCC | ACC | 817 |
| Arg | Arg | Gly | Ile | Gln | His | Leu | Tyr | Gly | Arg | Pro | Gln | Met | Thr | Pro | Thr | |
| 255 | | | | | 260 | | | | | 265 | | | | | | |
| TCC | CCC | GCC | CCA | ACT | TTG | AGC | TCC | CAG | GCT | GGG | ACA | GAT | ACC | AAT | GAG | 865 |
| Ser | Pro | Ala | Pro | Thr | Leu | Ser | Ser | Gln | Ala | Gly | Thr | Asp | Thr | Asn | Glu | |
| 270 | | | | | 275 | | | | | 280 | | | | | 285 | |
| ATT | GCA | CTG | CTG | GAG | CCG | GAA | ACC | CCG | CCA | GAT | GTC | TGT | GAG | ACT | TCC | 913 |
| Ile | Ala | Leu | Leu | Glu | Pro | Glu | Thr | Pro | Pro | Asp | Val | Cys | Glu | Thr | Ser | |
| | | | | 290 | | | | | 295 | | | | | 300 | | |
| TTC | GAC | GCG | GTT | TCC | ACC | ATC | CGA | GGA | GAG | CTC | TTC | TTC | TTC | AAG | GCA | 961 |
| Phe | Asp | Ala | Val | Ser | Thr | Ile | Arg | Gly | Glu | Leu | Phe | Phe | Phe | Lys | Ala | |
| | | | 305 | | | | | 310 | | | | | 315 | | | |
| GGC | TTT | GTG | TGG | AGG | CTG | CGC | AGT | GGG | CGA | CTG | CAG | CCC | GGG | TAT | CCT | 1009 |
| Gly | Phe | Val | Trp | Arg | Leu | Arg | Ser | Gly | Arg | Leu | Gln | Pro | Gly | Tyr | Pro | |
| | | 320 | | | | | 325 | | | | | 330 | | | | |
| GCT | TTG | GCC | TCT | CGG | CAC | TGG | CAA | GGA | CTG | CCC | AGC | CCT | GTG | GAT | GCA | 1057 |
| Ala | Leu | Ala | Ser | Arg | His | Trp | Gln | Gly | Leu | Pro | Ser | Pro | Val | Asp | Ala | |
| 335 | | | | | 340 | | | | | 345 | | | | | | |
| GCT | TTT | GAG | GAT | GCC | CAG | GGC | CAG | ATT | TGG | TTC | TTC | CAA | GGT | GCT | CAG | 1105 |
| Ala | Phe | Glu | Asp | Ala | Gln | Gly | Gln | Ile | Trp | Phe | Phe | Gln | Gly | Ala | Gln | |
| 350 | | | | | 355 | | | | | 360 | | | | | 365 | |
| TAC | TGG | GTA | TAT | GAT | GGT | GAG | AAG | CCA | GTC | CTA | GGC | CCT | GCA | CCA | CTC | 1153 |
| Tyr | Trp | Val | Tyr | Asp | Gly | Glu | Lys | Pro | Val | Leu | Gly | Pro | Ala | Pro | Leu | |
| | | | | 370 | | | | | 375 | | | | | 380 | | |
| TCC | AAG | CTG | GGC | CTG | CAA | GGG | TCC | CCA | GTT | CAT | GCC | GCC | TTG | GTC | TGG | 1201 |
| Ser | Lys | Leu | Gly | Leu | Gln | Gly | Ser | Pro | Val | His | Ala | Ala | Leu | Val | Trp | |
| | | | | 385 | | | | | 390 | | | | | 395 | | |
| GGT | CCT | GAG | AAG | AAC | AAG | ATC | TAC | TTC | TTC | CGA | GGT | GGA | GAC | TAT | TGG | 1249 |
| Gly | Pro | Glu | Lys | Asn | Lys | Ile | Tyr | Phe | Phe | Arg | Gly | Gly | Asp | Tyr | Trp | |
| | | 400 | | | | | 405 | | | | | 410 | | | | |

| | | | | | | | | | | | | | | | | |
|---|---|---|---|---|---|---|---|---|---|---|---|---|---|---|---|---|
| CGT | TTC | CAC | CCC | AGA | ACC | CAG | CGA | GTG | GAC | AAT | CCC | GTG | CCC | CGG | CGC | 1297 |
| Arg | Phe | His | Pro | Arg | Thr | Gln | Arg | Val | Asp | Asn | Pro | Val | Pro | Arg | Arg | |
| 415 | | | | | 420 | | | | | 425 | | | | | | |

| | | | | | | | | | | | | | | | | |
|---|---|---|---|---|---|---|---|---|---|---|---|---|---|---|---|---|
| TCC | ACT | GAC | TGG | CGA | GGG | GTA | CCT | TCT | GAG | ATT | GAT | GCT | GCC | TTC | CAG | 1345 |
| Ser | Thr | Asp | Trp | Arg | Gly | Val | Pro | Ser | Glu | Ile | Asp | Ala | Ala | Phe | Gln | |
| 430 | | | | | 435 | | | | | 440 | | | | | 445 | |

| | | | | | | | | | | | | | | | | |
|---|---|---|---|---|---|---|---|---|---|---|---|---|---|---|---|---|
| GAT | GCT | GAG | GGC | TAT | GCC | TAC | TTC | CTT | CGT | GGC | CAT | CTC | TAC | TGG | AAG | 1393 |
| Asp | Ala | Glu | Gly | Tyr | Ala | Tyr | Phe | Leu | Arg | Gly | His | Leu | Tyr | Trp | Lys | |
| | | | | 450 | | | | | 455 | | | | | 460 | | |

| | | | | | | | | | | | | | | | | |
|---|---|---|---|---|---|---|---|---|---|---|---|---|---|---|---|---|
| TTT | GAT | CCC | GTG | AAG | GTG | AAG | GTC | CTA | GAA | GGC | TTT | CCT | CGC | CCC | GTA | 1441 |
| Phe | Asp | Pro | Val | Lys | Val | Lys | Val | Leu | Glu | Gly | Phe | Pro | Arg | Pro | Val | |
| | | | 465 | | | | | 470 | | | | | 475 | | | |

| | | | | | | | | | | | | | | |
|---|---|---|---|---|---|---|---|---|---|---|---|---|---|---|
| GGT | CCT | GAC | TTC | TTT | GAC | TGT | GCT | GAG | CCT | GCC | AAT | ACT | TTC | CGC | 1486 |
| Gly | Pro | Asp | Phe | Phe | Asp | Cys | Ala | Glu | Pro | Ala | Asn | Thr | Phe | Arg | |
| | | 480 | | | | | 485 | | | | | 490 | | | |

| | | | | | |
|---|---|---|---|---|---|
| TGACAACACT | TTGGATGCAT | TCAGGGGTAC | TGACTCCTGC | CAGGGCACTT | AGATCATGTA | 1546 |
| AGAGACCCAC | AGCCATATCT | GTGGCTCTGG | CTTCAGGCAT | GGGACAGACA | GGGCCTATGT | 1606 |
| CTCCTCAGGG | GAGTGGGTTG | GGGTGCAGCC | ACTGTTTGTA | GGAACGACCA | TGCTGTCATG | 1666 |
| TCACCTGCCA | ACAATTGTCT | CAGACTAGGC | AAAGGCTTTG | GTGTTACTTA | AAAATAAGGG | 1726 |
| AGGTTTTGGG | CTGGCAATAT | TTCAGCTACC | AATAATCCAC | AGTCAGCCTG | GTTGCCCAAG | 1786 |
| GTCTCCTATC | TCTGTCCCTC | AATGTAGAAC | CCCCACACAA | ACTCAGGAAT | CACCTGCAAT | 1846 |
| GAGGTTCCTG | TTGGGAGTGG | TGTTGGTAAT | GAGATGCCCA | GGGTACCATG | CTGCCCCTGC | 1906 |
| TAAGCAACTG | GACCAGTATC | TTTCCTGGTA | AGTCAGCTCT | GGAGAGATAG | TGAACTGATC | 1966 |
| ATATTCTGGC | AGGTGATTCA | GACAAGTGCT | TCCTGGAACT | CAGGCCCCAA | GGTACACAGC | 2026 |
| CAGCCAAGGA | GGCAGCTGCT | TCCTCCCAGA | GACACGGAAC | CTCAAAGGCC | CCACATACCT | 2086 |
| CACAGCCTTG | CCCCAGGCCA | TTTCTTTCTG | GGGCCCTCTT | CCTAGCACAG | GTACCCTCTA | 2146 |
| AGCCATGTAC | ATGTGTATAC | AGTGTATAAA | GACTTTTTA | AAAAAACAAA | AAACCAAACC | 2206 |
| CCAAAAAAGC | CAAGACTGTC | ATTAAACATG | AGTGTTTCT | AAAAAAAAAA | AAAA | 2260 |

( 2 ) INFORMATION FOR SEQ ID NO:4:

( i ) SEQUENCE CHARACTERISTICS:
        ( A ) LENGTH: 492 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Ala | Arg | Ala | Ala | Cys | Leu | Leu | Arg | Ala | Ile | Ser | Gly | Cys | Leu | Leu |
| 1 | | | | 5 | | | | | 10 | | | | | 15 | |

| | | | | | | | | | | | | | | |
|---|---|---|---|---|---|---|---|---|---|---|---|---|---|---|
| Leu | Pro | Leu | Pro | Leu | Leu | Leu | Leu | Leu | Leu | Leu | Leu | Pro | Ser | Pro |
| | | | 20 | | | | | 25 | | | | | 30 | |

| | | | | | | | | | | | | | | |
|---|---|---|---|---|---|---|---|---|---|---|---|---|---|---|
| Leu | Met | Ala | Arg | Ala | Arg | Pro | Pro | Glu | Ser | His | Arg | His | Pro | Val |
| | | | 35 | | | | 40 | | | | | 45 | | |

| | | | | | | | | | | | | | | |
|---|---|---|---|---|---|---|---|---|---|---|---|---|---|---|
| Lys | Lys | Gly | Pro | Arg | Leu | Leu | His | Ala | Ala | Leu | Pro | Asn | Thr | Leu | Thr |
| | 50 | | | | | 55 | | | | | 60 | | | | |

| | | | | | | | | | | | | | | |
|---|---|---|---|---|---|---|---|---|---|---|---|---|---|---|
| Ser | Val | Pro | Ala | Ser | His | Trp | Val | Pro | Ser | Pro | Ala | Gly | Ser | Ser | Arg |
| 65 | | | | | 70 | | | | | 75 | | | | | 80 |

| | | | | | | | | | | | | | | |
|---|---|---|---|---|---|---|---|---|---|---|---|---|---|---|
| Pro | Leu | Arg | Cys | Gly | Val | Pro | Asp | Leu | Pro | Asp | Val | Leu | Asn | Ala | Arg |
| | | | | 85 | | | | | 90 | | | | | 95 | |

| | | | | | | | | | | | | | | |
|---|---|---|---|---|---|---|---|---|---|---|---|---|---|---|
| Asn | Arg | Gln | Lys | Arg | Phe | Val | Leu | Ser | Gly | Gly | Arg | Trp | Glu | Lys | Thr |
| | | | 100 | | | | | 105 | | | | | 110 | | |

| | | | | | | | | | | | | | | |
|---|---|---|---|---|---|---|---|---|---|---|---|---|---|---|
| Asp | Leu | Thr | Tyr | Arg | Ile | Leu | Arg | Phe | Pro | Trp | Gln | Leu | Val | Arg | Glu |

|  |  |  |  |  | 115 |  |  |  |  | 120 |  |  |  |  | 125 |  |
|---|---|---|---|---|---|---|---|---|---|---|---|---|---|---|---|---|
| Gln | Val | Arg | Gln | Thr | Val | Ala | Glu | Ala | Leu | Gln | Val | Trp | Ser | Glu | Val |  |
|  | 130 |  |  |  | 135 |  |  |  |  | 140 |  |  |  |  |  |  |

```
                    115                         120                          125

Gln  Val  Arg  Gln  Thr  Val  Ala  Glu  Ala  Leu  Gln  Val  Trp  Ser  Glu  Val
     130                 135                      140

Thr  Pro  Leu  Thr  Phe  Thr  Glu  Val  His  Glu  Gly  Arg  Ala  Asp  Ile  Met
145                      150                      155                      160

Ile  Asp  Phe  Ala  Arg  Tyr  Trp  Asp  Gly  Asp  Asn  Leu  Pro  Phe  Asp  Gly
                    165                      170                      175

Pro  Gly  Gly  Ile  Leu  Ala  His  Gly  Phe  Phe  Pro  Lys  Thr  His  Arg  Glu
               180                 185                           190

Gly  Asp  Val  His  Phe  Asp  Tyr  Asp  Glu  Thr  Trp  Thr  Ile  Gly  Asp  Asn
          195                 200                      205

Gln  Gly  Thr  Asp  Leu  Leu  Gln  Val  Ala  Ala  His  Glu  Phe  Gly  His  Val
     210                      215                 220

Leu  Gly  Leu  Gln  His  Thr  Thr  Ala  Ala  Lys  Ala  Leu  Met  Ser  Pro  Phe
225                      230                 235                           240

Tyr  Thr  Phe  Arg  Tyr  Pro  Leu  Ser  Leu  Ser  Pro  Asp  Asp  Arg  Arg  Gly
                    245                 250                      255

Ile  Gln  His  Leu  Tyr  Gly  Arg  Pro  Gln  Met  Thr  Pro  Thr  Ser  Pro  Ala
               260                 265                      270

Pro  Thr  Leu  Ser  Ser  Gln  Ala  Gly  Thr  Asp  Thr  Asn  Glu  Ile  Ala  Leu
          275                 280                      285

Leu  Glu  Pro  Glu  Thr  Pro  Pro  Asp  Val  Cys  Glu  Thr  Ser  Phe  Asp  Ala
     290                 295                      300

Val  Ser  Thr  Ile  Arg  Gly  Glu  Leu  Phe  Phe  Phe  Lys  Ala  Gly  Phe  Val
305                      310                 315                           320

Trp  Arg  Leu  Arg  Ser  Gly  Arg  Leu  Gln  Pro  Gly  Tyr  Pro  Ala  Leu  Ala
                    325                 330                      335

Ser  Arg  His  Trp  Gln  Gly  Leu  Pro  Ser  Pro  Val  Asp  Ala  Ala  Phe  Glu
               340                 345                      350

Asp  Ala  Gln  Gly  Gln  Ile  Trp  Phe  Phe  Gln  Gly  Ala  Gln  Tyr  Trp  Val
          355                 360                 365

Tyr  Asp  Gly  Glu  Lys  Pro  Val  Leu  Gly  Pro  Ala  Pro  Leu  Ser  Lys  Leu
     370                 375                      380

Gly  Leu  Gln  Gly  Ser  Pro  Val  His  Ala  Ala  Leu  Val  Trp  Gly  Pro  Glu
385                      390                 395                           400

Lys  Asn  Lys  Ile  Tyr  Phe  Phe  Arg  Gly  Gly  Asp  Tyr  Trp  Arg  Phe  His
                    405                      410                      415

Pro  Arg  Thr  Gln  Arg  Val  Asp  Asn  Pro  Val  Pro  Arg  Arg  Ser  Thr  Asp
               420                      425                 430

Trp  Arg  Gly  Val  Pro  Ser  Glu  Ile  Asp  Ala  Ala  Phe  Gln  Asp  Ala  Glu
          435                      440                 445

Gly  Tyr  Ala  Tyr  Phe  Leu  Arg  Gly  His  Leu  Tyr  Trp  Lys  Phe  Asp  Pro
     450                      455                 460

Val  Lys  Val  Lys  Val  Leu  Glu  Gly  Phe  Pro  Arg  Pro  Val  Gly  Pro  Asp
465                      470                 475                           480

Phe  Phe  Asp  Cys  Ala  Glu  Pro  Ala  Asn  Thr  Phe  Arg
               485                      490
```

ANTIBODIES SPECIFIC FOR HUMAN STROMELYSIN-3 AND A METHOD FOR DETECTION OF STROMELYSIN-3

This application is a continuation-in-part of U.S. Ser. No. 07/794,393, filed Nov. 21, 1991, issued as U.S. Pat. No. 5,236,844.

FIELD OF THE INVENTION

The present invention relates to tumor-associated enzyme markers.

Utilizing DNA sequences encoding stromelysin-3, and antibodies capable of binding to stromelysin-3, the present invention provides methods for diagnosing cancer, specifically malignant breast cancer.

BACKGROUND OF THE INVENTION

The number of deaths around the world from cancer each year continues to be of major concern, with only a few treatments being available for specific types of cancer, and these having no absolute guarantee of success. Most treatments rely on a general "shotgun" approach, killing off rapidly growing cells in the hope that rapidly growing cancerous cells will succumb, either to the treatment, or at least be reduced in numbers to allow the body's system to eliminate the remainder.

The search for cures has been hampered by the discovery that different forms of cancer require different treatments. Given that virtually any part of the body can be affected by cancer, the task becomes enormous.

Nevertheless, despite their differences, cancers also share a number of similarities. Prime amongst these is the growth of undifferentiated tissue. However, even this is not 100% accurate, in that certain cancerous cells do exhibit a degree of differentiation, and this is shown in the sex cancers, such as those of breast and testicle, where tumors may be positive or negative for hormone receptors. Treatment of these tumors depends on the hormone state, and may be as simple as administration of the relevant hormone antagonist, such as tamoxifen.

Another factor which most cancers share is that, in order to be fatal, they must metastasize. Until such time as metastasis occurs, a tumor, although it may be malignant, is confined to one area of the body. This may cause discomfort and/or pain, or even lead to more serious symptoms, but if it can be located, it may be surgically removed and, if done with adequate care, cause no further problems.

However, once metastasis sets in, surgical resection may remove the parent tumor, but cancerous cells have invaded the body, and only chemotherapy, or some particular form of targeting therapy, stands any chance of success.

Thus, the ability to invade locally and to metastasize in organs distant from the primary tumor (tumor progression) is the lethal event in the course of most cancers. Alteration/degradation of the extracellular matrix (ECM) surrounding the primary tumor, and modifications of the tumor cell adhesive properties, are known to be crucial for dissociation of the metastatic cells from the primary tumor cells (Liotta, *Cancer Res.* 46:1–7 (1986); Hart et al., *Biochim. Biophys. Acta* 989:65–84 (1989)).

Tumor angiogenesis is essential for both primary tumor expansion and metastatic tumor spread, and angiogenesis itself requires ECM degradation (Blood et al., *Biochim. Biophys. Acta* 1032:89–118 (1990)). Thus, malignancy is a systemic disease in which interactions between the neoplastic cells and their environment play a crucial role during evolution of the pathological process (Fidler, I. J., *Cancer Metastasis Rev.* 5:29–49 (1986)).

Identifying the alterations in gene expression which are associated with malignant tumors, including those involved in tumor progression, is clearly a prerequisite not only for a full understanding of cancer, but also to develop new rational therapies against cancer. Mutations and/or abnormal control of expression of two groups of cellular genes (the proto-oncogenes and the tumor suppressor genes) have been shown to lead in a multistep process to the loss of normal growth control and to the acquisition of the transformed cell phenotype (Weinberg, R. A., *Cancer Res.* 49:3713–3721 (1989)). However, the molecular mechanisms which lead to tumor progression are much less clear (Nowell, P. C., *Cancer Res.* 46:2203–2207 (1986); Fidler, I. J., *Cytometry* 10:673–680 (1989)).

Thus, a further problem arises, in that the genes characteristic of cancerous cells are very often host genes being abnormally expressed. It is quite often the case that a particular protein marker for a given cancer is over-expressed in that cancer, but is also expressed elsewhere throughout the body, albeit at reduced levels.

Some of the proteins associated with cancers are enzymes which break down the extracellular matrix, which is important for maintaining cells in their proper relationship to each other. One such class is the metalloproteinases (MMPs) (Matrisian, L. M., *Trends Genet.* 6:121–125 (1990)), so called because they bind zinc. However, none has been found to be diagnostic of cancer, or any particular tumors, although the presence of some may be indicative.

MMPs are involved in a number of physiological and pathological processes in which ECM remodelling and cell migration are implicated, e.g. morphogenesis and embryonic development, rheumatoid arthritis, and tumor invasion and metastasis. MMP inhibitors are known to be able to block tumor invasion and angiogenesis, which are crucial for tumor progression, in experimental models.

All members of the matrix metalloproteinase family are proteinases which degrade at least one component of ECM, are secreted in a latent form and require activation, such as proteolysis (e.g. by plasmin) to become active. Interstitial collagenases specifically attack connective tissue collagens (I to III), whereas type IV collagenases (72 kD and 92 kD) degrade collagens present in the basement membrane and fibronectin. Stromelysins (transins) -1 and -2, and also pump-1, have a much broader substrate specificity, degrading proteoglycans, laminin, fibronectin, and collagens (III to V).

In man, most of the malignant tumors are carcinomas, and among non-smokers, breast cancer is the leading cause of mortality by cancer in woman (Willett, W., *Nature* 338:389–394 (1989)). The expression of several oncogenes has been reported to be altered in malignant breast cells and tumors, but no particular pattern of oncogene/suppressor gene expression can be consistently associated with breast cancer (Gullick, W. J., *Prog. Growth Factor Res.* 2:1–13 (1990)).

However, the neoplastic cells of breast tumors are often embedded in an adipose and mesenchymal stroma, which may also be important in control of their proliferation and in their ability to metastasize. Indeed, it is known that stroma cells can modulate, both positively and negatively, the growth of normal mammary epithelium (Salomon et al., in *Breast Cancer: Cellular and Molecular Biology* (eds., Lippman, M. E. and Dickson, R. B.), pp. 363–389 (Kluwer, Boston, (1988)), and that interactions between the epithelial and stromal components can influence epithelial carcinogenesis in the mammary gland (DeOme et al., *Cancer Res.* 38:2103–2111 (1978)).

The existence of "activated" (Tremblay, *G. Exp. Mol. Pathol.* 31:248–260 (1979)) and/or abnormal (Grey et al., *Proc. Nat. Acad. Sci. USA* 86: 2438–2442 (1989)) fibroblasts in malignant breast tumors has been postulated, and it has been proposed that breast cancer could represent a partial escape from dependence on a stromal requirement or an abnormally strong response to a stromal component.

Owing to the nature of cancerous tissue, it is usually relatively easy to set up a continuous culture, or cell line, of a given cancer, a process which makes it easy to study the effects of a given treatment regimen. A significant drawback to such systems lies in their very nature—while the test treatment will establish whether it can act directly against the cells, it is by no means certain what effect the treatment will have in vivo, and biochemical analysis of such lines is inevitably in the absence of the tissue normally surrounding the tumor in vivo.

Recently, a new member of the MMP gene family, the stromelysin-3 (ST3) gene, has been identified in breast carcinoma, where it is expressed in most, if not all, invasive tumors (Basset, P., et al., *Nature (Lond.)* 348:699–704 (1990)). The new MMP was termed ST3 because it has the same general structure as the previously described stromelysins (Basset, P., et al., *Nature (Lond.)* 348:699–704 (1990); Muller, D., et al., *Biochem. J.* 253:187–192 (1988)), and because it was expressed in the stromal cells surrounding invasive neoplastic cells (Basset, P., et al., *Nature (Lond.)* 348:699–704 (1990)). However, its substrate specificity is unknown and several lines of evidence indicate that ST3 may be in fact the first member of a new MMP subgroup (Murphy and Reynolds, *FEBS Lett.* 289:4–7 (1991); Levy, A., et at., *Genomics* 13:881–883 (1992)).

It has been previously demonstrated that stromelysin-2 (ST2) and interstitial type I collagenase gene expressions were both increased in head and neck squamous cell carcinomas (Muller, D., et al., *Int. J. Cancer* 48:550–556 (1991); Polette, M., et al., *Invasion Metastasis* 11:76–83 (1991)). We have shown that 95% (106 of 111) of head and neck squamous cell carcinomas also overexpress the ST3 gene, and that ST3 RNA is, as in breast carcinoma, specifically detected in stromal cells immediately surrounding invasive cancer cells (Muller, D., et al., *Cancer Res.*, in press (1993)). Furthermore, we have observed that the tumors with high levels of ST3 RNA were more likely to exhibit high local invasiveness, suggesting that ST3 may contribute to the progression of head and neck carcinomas.

SUMMARY OF THE INVENTION

It is an object of the invention to identify genes whose expression is increased in breast carcinomas, whereby breast carcinomas are considered as malignant epithelial cells interacting with their surrounding stroma.

We have now found that a previously uncharacterized protein is diagnostic of certain invasive cancers, especially breast carcinomas, head and neck squamous cell carcinomas and skin (squamous and basal cell types) carcinomas. The protein apparently belongs to the group of metalloproteinases, and is referred to as stromelysin-3 herein.

BRIEF DESCRIPTION OF THE DRAWINGS

FIG. 1A depicts a Northern blot analysis of total RNA from C1 breast carcinoma and F1 fibroadenoma.

FIG. 1B depicts a Northern blot analysis of total RNA from C1 breast carcinoma and F1 fibroadenoma.

FIG. 1C depicts a Northern blot analysis of total RNA from C1 breast carcinoma and F1 fibroadenoma.

FIG. 1D depicts a Northern blot analysis of total RNA from C1 breast carcinoma and F1 fibroadenoma.

Figure 4A:
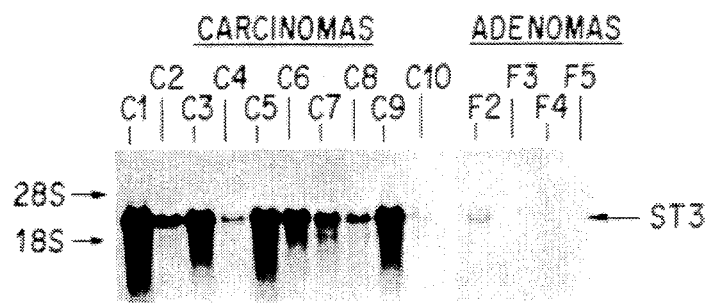

For each analysis depicted by FIG. 1A, FIG. 1B, FIG. 1C and FIG. 1D, RNA, isolated from C1 breast carcinoma and F1 Fibroadenoma cells, was probed using four independently isolated cDNA probes as described in Example 1.

FIG. 2A and FIB. 2B depict the nucleotide sequence of stromelysin-3 cDNA and the deduced amino acid sequence of stromelysin-3.

FIG. 2A depicts the first 900 bases of the cDNA starting from the 5' end and the first 297 amino acids of the protein. The underlined nucleotide sequences correspond to the putative signal peptide, the PRCGVPD sequence characteristic of prometalloproteinase and the conserved histidine residues of the zinc-binding domain, respectively.

FIG. 2B depicts base numbers 901 to 2256 of the cDNA counting from the 5' end, and amino acids 298 to 488 of the protein. The underlined nucleotide sequence corresponds to the poly($A^+$) signal sequence.

FIG. 3A, FIG. 3B and FIG. 3C depict the aligned amino acid sequences for stromelysin-3, stromelysin-2, stromelysin-1 and collagenase-1, all putative metalloproteinases, as described in Example 3.

FIG. 3A depicts up to approximately 169 amino acids of each of these proteins.

FIG. 3B continues the amino acid sequence for each protein.

FIG. 3C continues the amino acid sequence for each protein to the terminus.

FIG. 3D compares the similarity of stromelysin-1, stromelysin-2 and collagenase-1 to stromelysin-3; and compares the similarity of stromelysin-2 and collagenase-1 to the stromelysin-1.

FIG. 4A, FIG. 4B, FIG. 4C, FIG. 4D, FIG. 4E and FIG. 4F depict photographs of Northern blot analyses of human metalloproteinases. Total RNA was prepared from four oestrogen receptor negative breast carcinomas (C1, grade II; C2, C3 and C4, grade III), six oestrogen receptor positive breast carcinomas (C5, C8 and C9, grade II; C6 and C7, grade 3; C10, grade I) and four breast fibroadenomas (F2–F5). Each analysis was carried as described in Example 4.

FIG. 4A depicts the results obtained when the RNA was probed with stromelysin-3 RNA.

Figure 4B:

FIG. 4B depicts the results obtained when the RNA was probed with type I collagenase RNA (COI).

Figure 4C:
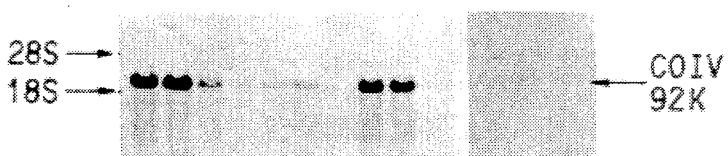

FIG. 4C depicts the results obtained when the RNA was probed with a 92 kd type IV collagenase RNA (COIV 92k).

Figure 4D:
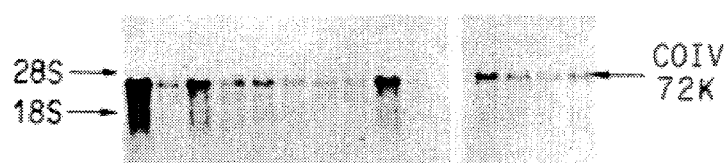

FIG. 4D depicts the results obtained when the RNA was probed with 72 kd type IV collagenase RNA (COIV 72k).

Figure 4E:
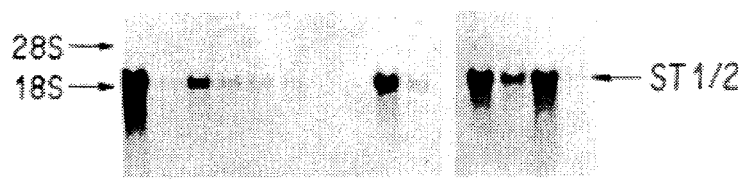

FIG. 4E depicts the results obtained when the RNA was probed with stromelysin-1 and 2 RNA (ST1/2).

Figure 4F:

FIG. 4F depicts the results obtained when the RNA was probed pump-1 RNA (PUI).

Figures 5A, 5B:
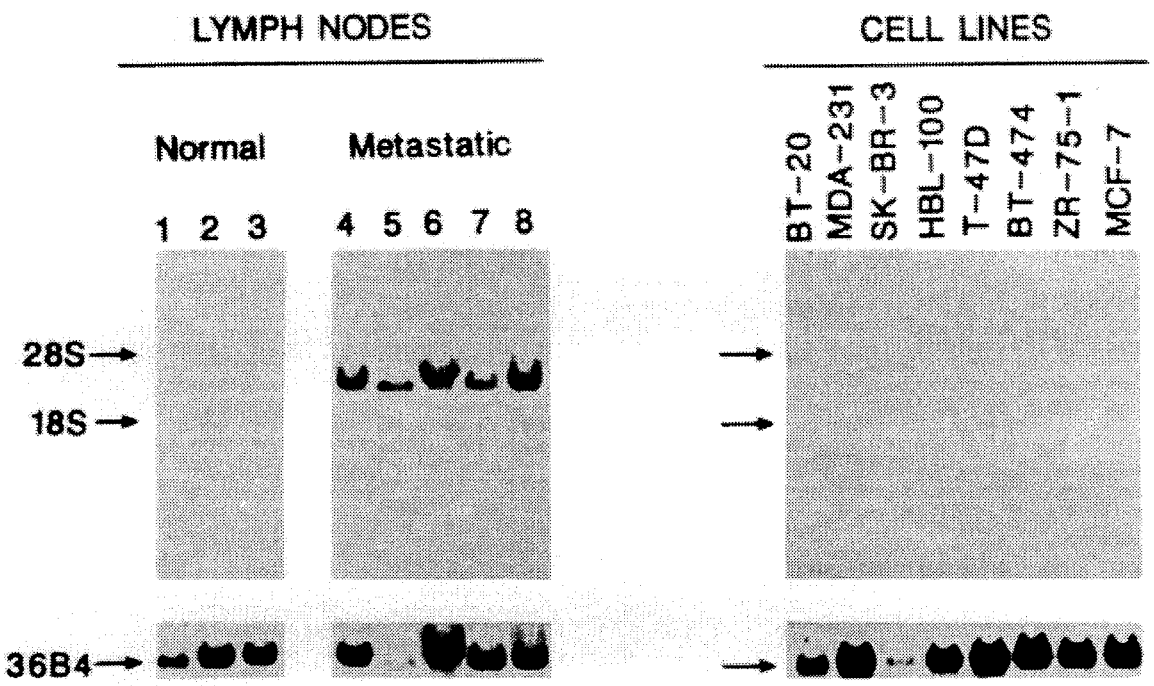

FIG. 5A depicts a photograph showing the results of a Northern blot analysis of stromelysin-3 RNA from three normal and five metastatic auxiliary lymph nodes from patients having breast cancer.

FIG. 5B is a photograph depicting the results of a Northern blot analysis of stromelysin-3 RNA from fur oestrogen receptor negative breast carcinoma cell lines (BT-20, MDA-231, SK-BR-3, HBL-100); and four oestrogen receptor positive breast carcinoma cell lines (T-47D, BT-474, ZR-75-1, MCF-7).

Figures 5C, 5D:
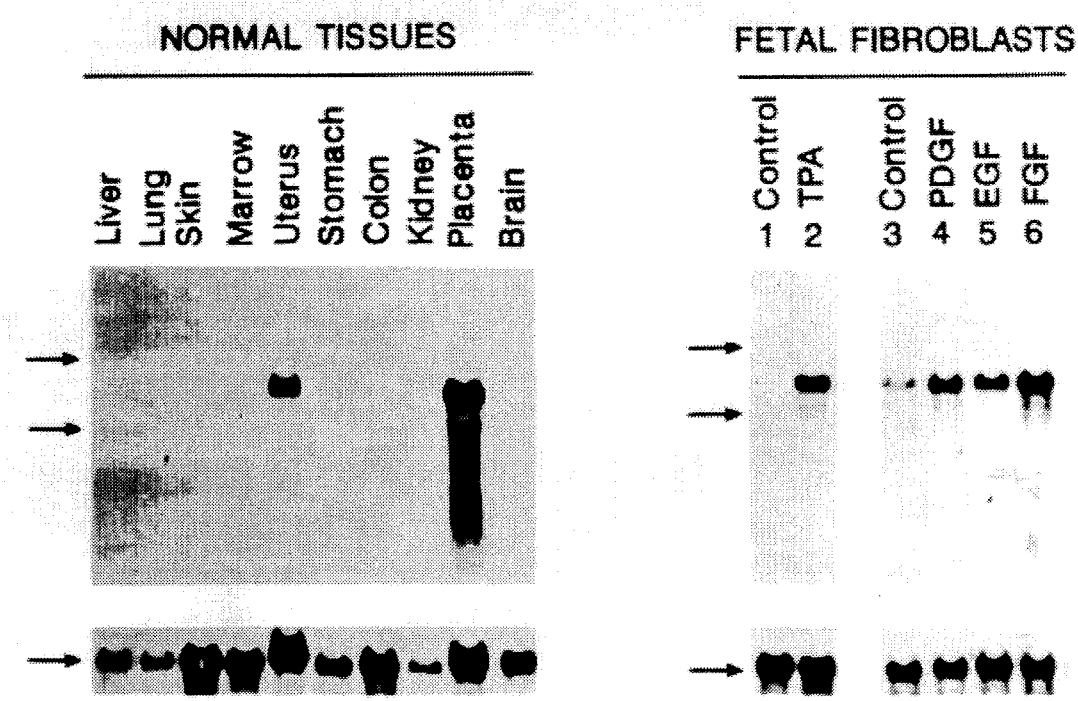

FIG. 5C is a photograph depicting the results of a Northern blot analysis of stromelysin-3 RNA from ten normal human tissues.

FIG. 5D is a photograph depicting the results of a Northern blot analysis of stromelysin-3 RNA from HFL-1 Human Fetal Deployed Fibroblasts (ATCC CCL 153) cultured in serum-free medium (1 and 2), in the absence (1) or presence (2) of TPA; cultured in serum-free media supplemented with 20 mg/ml insulin (3–6), in the absence (3) or presence (4) of TDGF, (5) of all EGF, or (6) of bFGF.

In each of FIGS. 5A–5D, the various cell lines and tissues were probed with stromelysin-3 sequences as described in Example 5.

FIG. 6A–FIG. 6L show the presence of stromelysin-3 RNA transcripts in sections of breast carcinomas and embryolimb bud. FIG. 6A, FIG. 6C, FIG. 6E, FIG. 6G, FIG. 6I and FIG. 6K each depict bright field of tissue sections (×100) stained with hematoxylin. FIG. 6B, FIG. 6D, FIG. 6F, FIG. 6H, FIG. 6J and FIG. 6L each show dark field images of the same sections (still stained with hematoxylin) after in situ hybridization with an antisense stromelysin-3 cRNA probe.

Figure 6A:
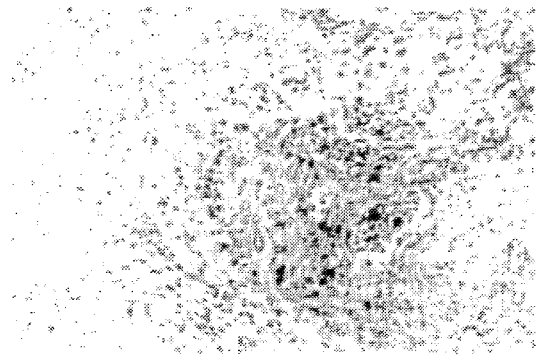

FIG. 6A depicts a grade II ductal breast carcinoma (tumor C1).

Figure 6B:
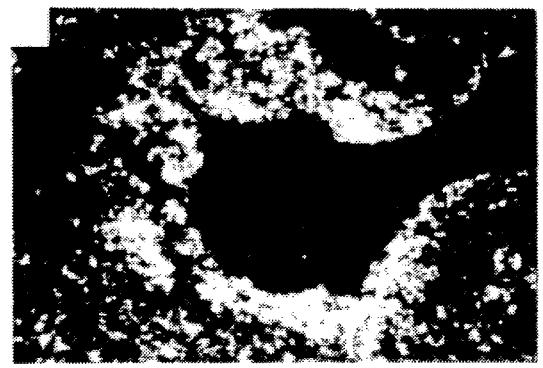

FIG. 6B depicts the same grade II ductal breast carcinoma after in situ hybridization with an antisense stromelysin-3 cRNA probe.

Figure 6C:
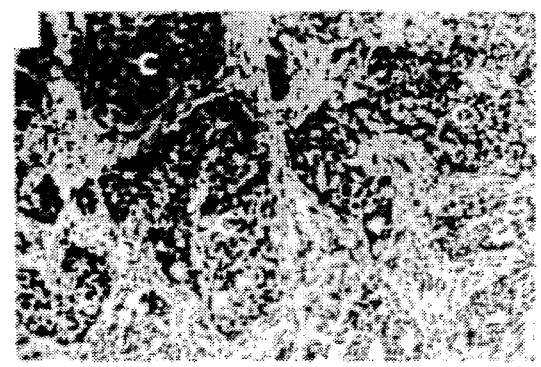

FIG. 6C depicts a grade III ductal breast carcinoma.

Figure 6D:
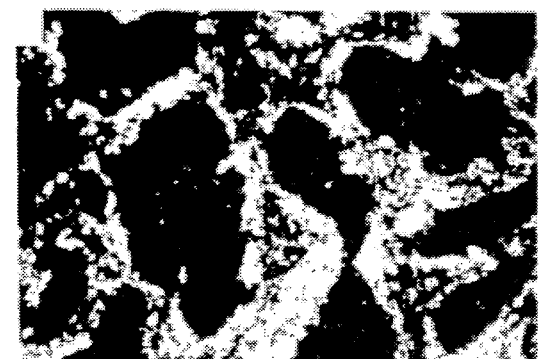

FIG. 6D depicts the same grade III ductal breast carcinoma after in situ hybridization with an antisense stromelysin-3 cRNA probe.

Figure 6E:

FIG. 6E depicts a ductal carcinoma, together with two normal lobules (N).

Figure 6F:
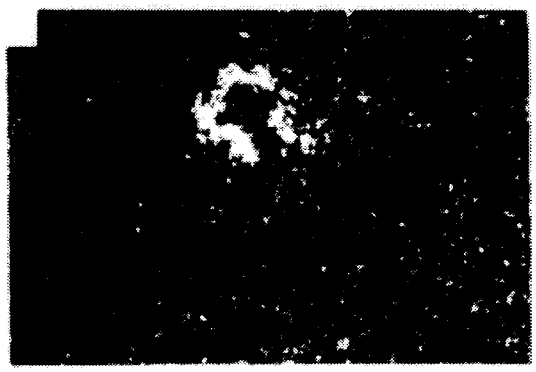

FIG. 6F depicts the same tissue section after in situ hybridization with an antisense stromelysin-3 cRNA probe.

Figure 6G:
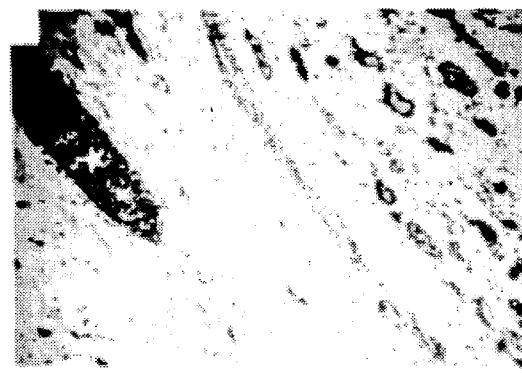

FIG. 6G depicts a ductal carcinoma.

Figure 6H:
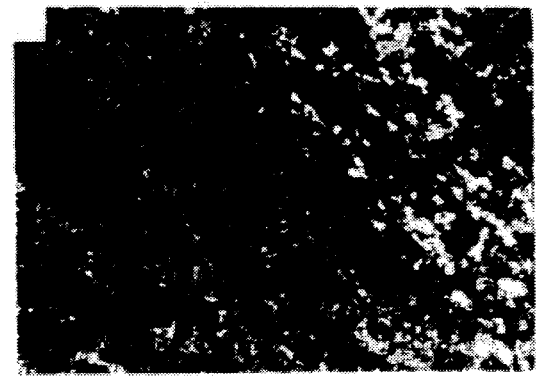

FIG. 6H depicts the same ductal carcinoma after in situ hybridization with an antisense stromelysin-3 cRNA probe.

Figure 6I:
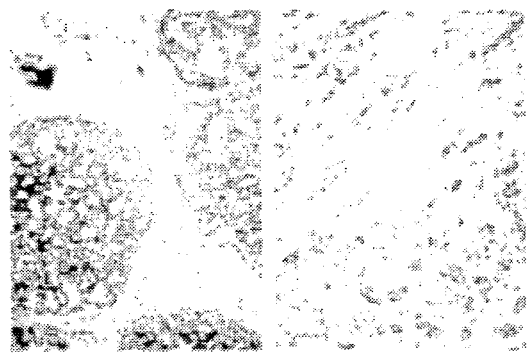

FIG. 6I depicts a ductal carcinoma.

Figure 6J:
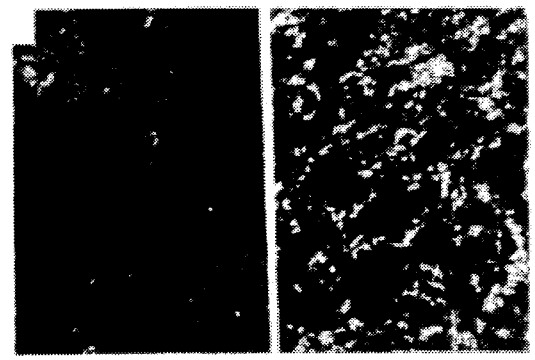

FIG. 6J depicts the same ductal carcinoma after in situ hybridization with an antisense stromelysin-3 cRNA probe.

Figure 6K:

FIG. 6K depicts an interdigital region of an 8-week-old human embryolimb bud.

Figure 6L:

FIG. 6L depicts the same tissue section after in situ hybridization with an antisense stromelysin-3 cRNA probe.

FIG. 7A depicts the first 1020 bases of the cDNA sequence of mouse ST3 gene and the first 337 bases of human ST3 cDNA sequence.

FIG. 7B continues the cDNA sequences of mouse ST3 gene and human ST3 cDNA.

Figure 8:
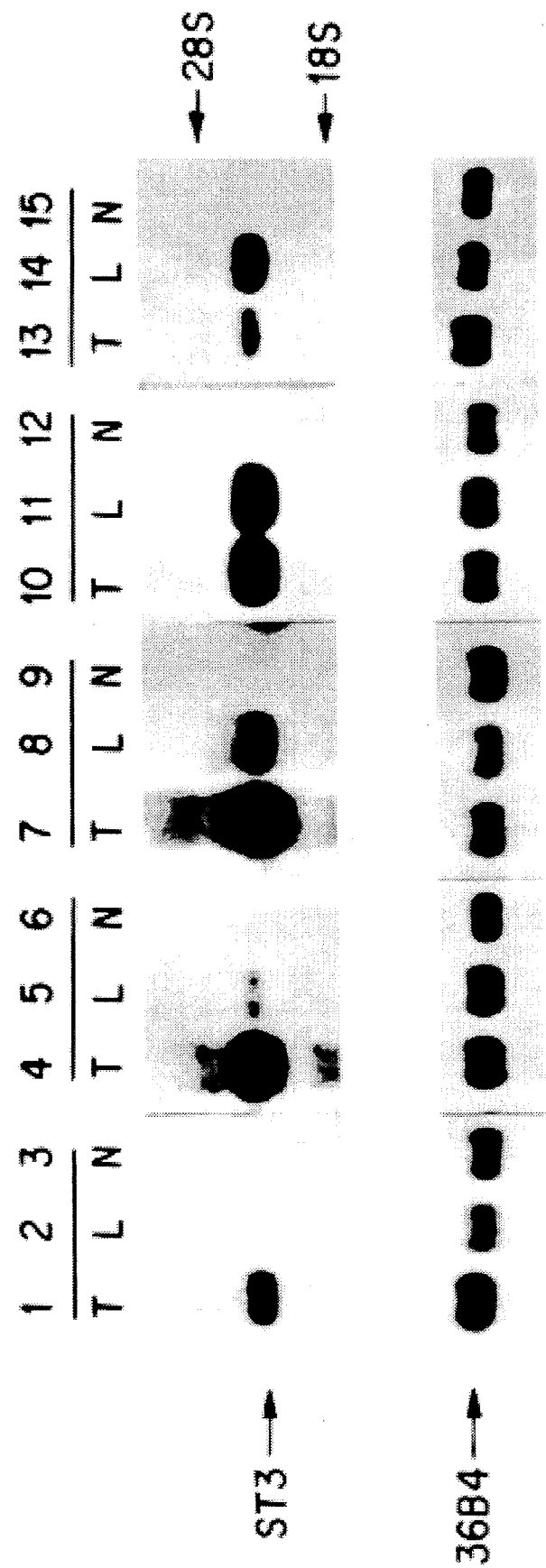

FIG. 8 depicts a Northern blot analysis of stromelysin-3 RNA in head and neck tissue. 20 μg of total RNA was loaded in each lane. Hybridization was performed with a $^{32}$P-labeled ST3 cDNA probe and each blot was rehybridized with a $^{32}$P-labeled 36B4 probe to check the amount of transferred RNA in each lane, as described in "Materials and Methods". Autoradiography was for 48 h (ST3) and 6 h (36B4). T head and neck squamous cell carcinoma, L metastatic lymph node; and N normal mucosa; each case T L N set corresponds to samples from one patient.

FIGS. 9A–9F are photographs depicting the results of in situ hybridization of stromelysin-3 RNA on head and neck tissue sections.

Figure 9A:
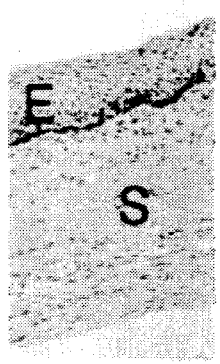

FIG. 9A is a bright-field photomicrograph of paraffin-embedded normal mucosa tissue section (×100) stained with hematoxylin-eosin.

Figure 9B:
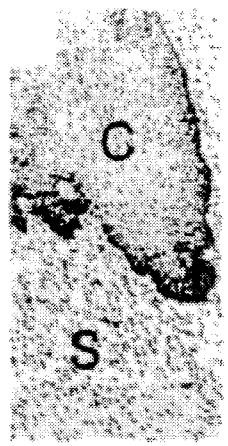

FIG. 9B is a bright-field photomicrograph of paraffin-embedded in situ carcinoma tissue section (×100) stained with hematoxylin-eosin.

Figure 9C:
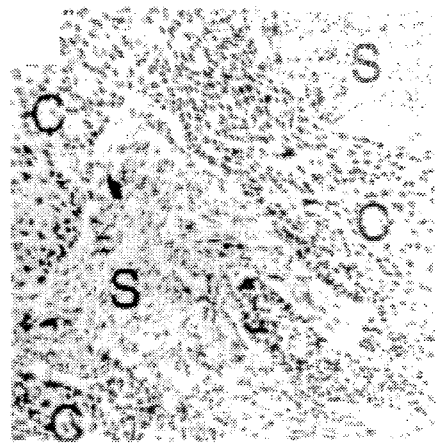

FIG. 9C is a bright-field photomicrograph of paraffin-embedded invasive squamous cell carcinoma tissue section (scored 2+ for local invasiveness), stained with hematoxylin-eosin, after in situ hybridization with $^{32}$S-labeled stromelysin-3 antisense RNA.

For each of FIG. 9A, FIG. 9B and FIG. 9C, E is normal epithelial; S is stroma and C is cancer cells.

Figure 9D:

FIG. 9D is a dark-field photomicrograph of the same tissue section employed in FIG. 9A, where stromelysin-3 transcripts appear as white silver precipitate.

Figure 9E:

FIG. 9E is a dark-field micrograph of the same tissue section employed in FIG. 9B, with stromelysin-3 transcripts appearing as white silver precipitate.

Figure 9F:
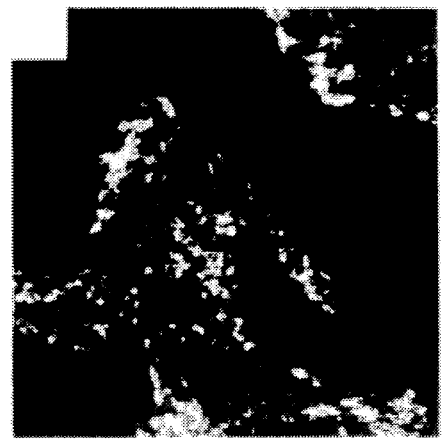

FIG. 9F is a dark-field photomicrograph of the same tissue section employed in FIG. 9C, with stromelysin-3 transcripts appearing as white silver precipitate.

Figure 10A:
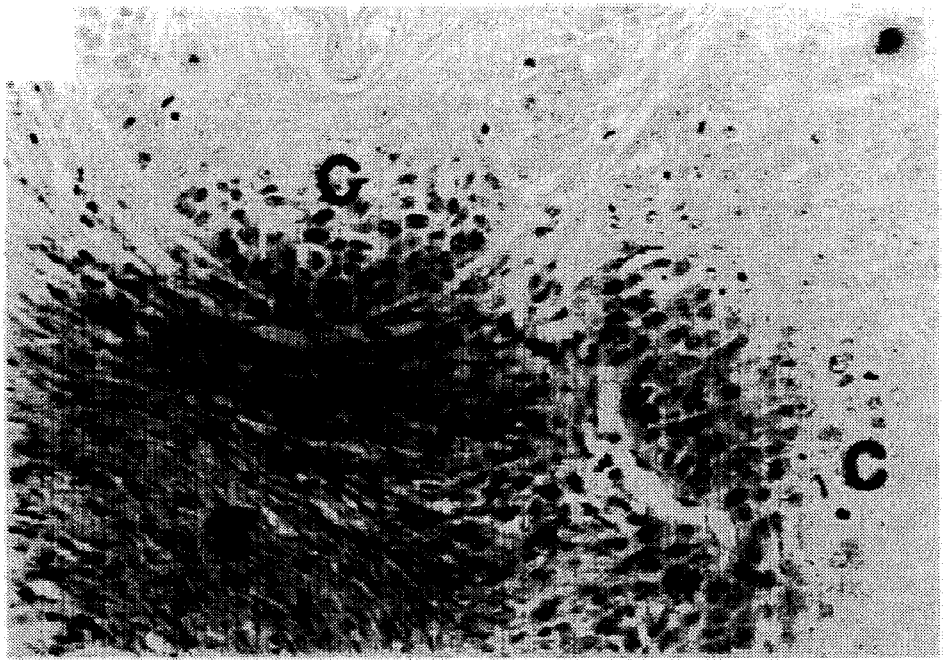

FIG. 10A is a photomicrograph of a paraffin-embedded tissue section (×200) of an invasive squamous cell carcinoma (scored 3+ for local invasiveness), after immunohistochemical analysis with a polyclonal antibody (Ab 349) to the C-terminal part of stromelysin-3; C, cancer cell; S, stroma.

Figure 10B:

FIG. 10B is a photomicrograph of the same paraffin-embedded tissue section (×500) that was employed in FIG. 10A.

For each of FIG. 10A and FIG. 10B, indirect immunoperoxidase staining of stromelysin-3 protein was employed.

FIGS. 11A–11L are photomicrographs of serial paraffin-embedded tissue sections (×100) of invasive squamous cell carcinomas, after in situ hybridization with $^{35}$S-labeled antisense RNA probes.

Figure 11C:
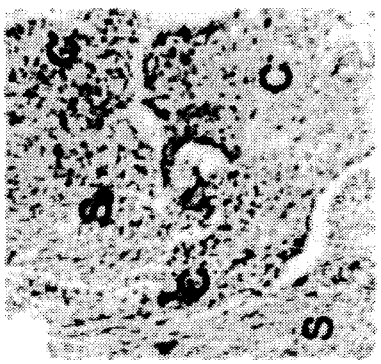
Figure 11B:
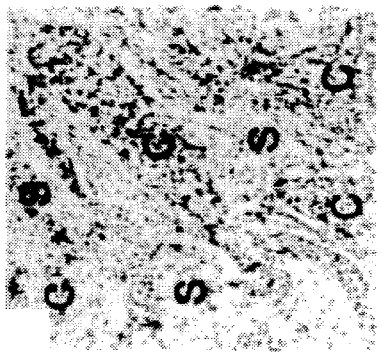
Figure 11A:

FIG. 11A is a bright-field micrograph of said tissue sections stained with hematoxylin-eosin.

FIG. 11B is another bright-field micrograph of an invasive squamous cell carcinoma tissue section stained with hematoxylin-eosin.

FIG. 11C is another bright-field micrograph of a squamous cell carcinoma tissue section stained with hematoxylin-eosin.

For each of FIG. 11A, FIG. 11B and FIG. 11C, C designates cancer cells and S designates stroma.

Figure 11F:
Figure 11E:
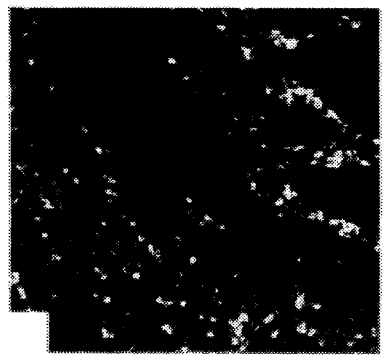
Figure 11D:
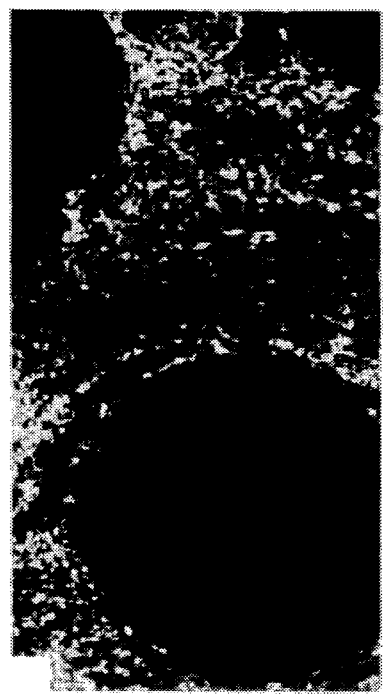

FIG. 11D is a dark-field micrograph of the tissue section shown in FIG. 11A after hybridization with stromelysin-3.

FIG. 11E is a dark-field micrograph of the tissue section shown in FIG. 11B after hybridization with stromelysin-3.

FIG. 11F is a dark-field micrograph of the tissue section shown in FIG. 11C after hybridization with stromelysin-3.

Figure 11I:
Figure 11L:
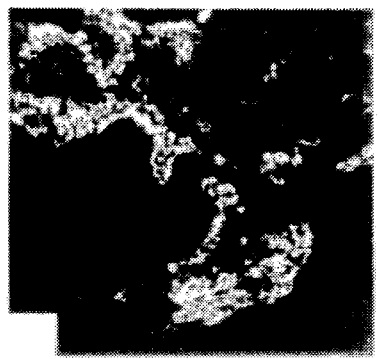
Figure 11H:
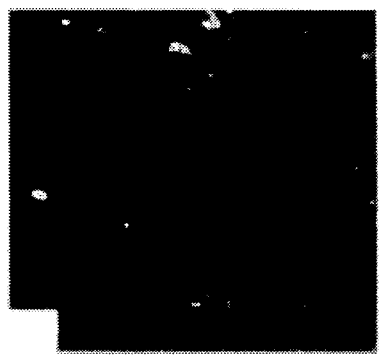
Figure 11K:
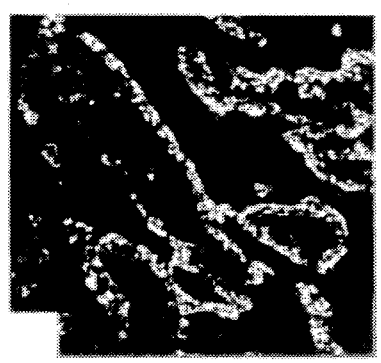
Figure 11G:

FIG. 11G is a dark-field micrograph of the tissue section shown in FIG. 11A after hybridization with interstitial type I collagenase.

FIG. 11H is a dark-field micrograph of the tissue section shown in FIG. 11B after hybridization with interstitial type I collagenase.

FIG. 11I is a dark-field micrograph of the tissue section shown in FIG. 11C after hybridization with interstitial type I collagenase.

Figure 11J:

FIG. 11J is a dark-field micrograph of the tissue section shown in FIG. 11A after hybridization with stromelysin-2 antisense RNA, where transcripts appear as white silver precipitate.

FIG. 11K is a dark-field micrograph of the tissue section shown in FIG. 11B after hybridization with stromelysin-2 antisense RNA, where transcripts appear as white silver precipitate.

FIG. 11L is a dark-field micrograph of the tissue section shown in FIG. 11C after hybridization with stromelysin-2 antisense RNA, where transcripts appear as white silver precipitate.

The invasive squamous cell carcinoma of FIG. 11A and FIG. 11J scored (3+) for local invasiveness. The invasive squamous cell carcinoma of FIG. 11B and FIG. 11K scored (3+) for local invasiveness. The invasive squamous cell carcinoma of FIG. 11C and FIG. 11L scored (2+) for local invasiveness.

Figures 12A, 12B:
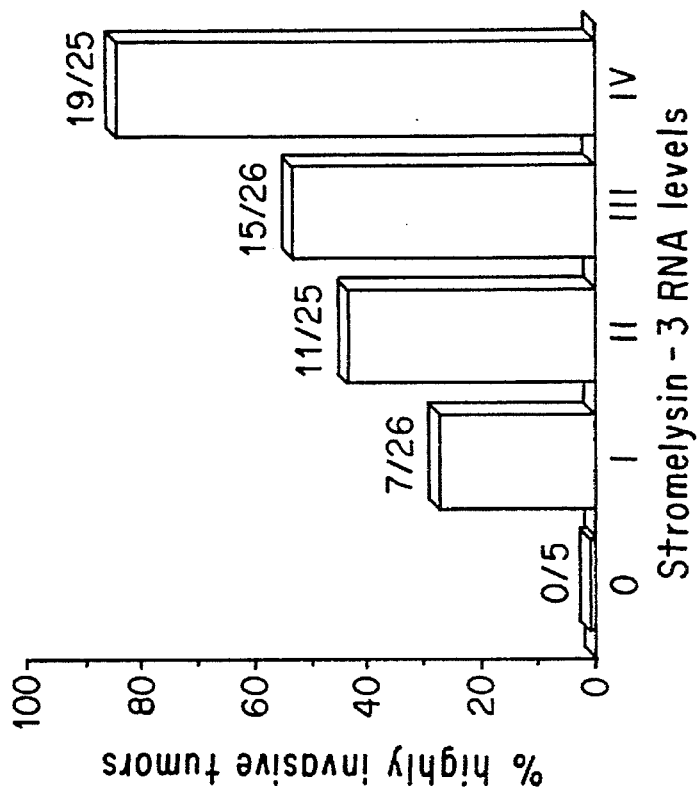

FIG. 12A is a chart that shows the distribution of stromelysin-3 RNA levels as a function of local invasiveness in head and neck carcinomas. Stromelysin-3 RNA levels were quantified by Northern blot densitometry, and separated in classes as described herein; 0, no expression; I, >0–2.5 units; II, >2.5–6 units; III, >6–15 units; IV, levels higher than 15 units. Invasiveness was scored from (1+) to (3+) as described herein.

FIG. 12B plots the percentage of highly invasive tumors, that is, the ratio of highly invasive tumors to the total number of tumors for each class of stromelysin-3 RNA level.

FIGS. 13A–13L depict bright-field and dark-field photomicrographs of paraffin-embedded tissue sections stained with hematoxylin after in situ hybridization with [$^{35}$S]-labeled stromelysin-3 (ST3) antisense RNA.

Figure 13C:
Figure 13F:
Figure 13B:
Figure 13E:
Figure 13A:
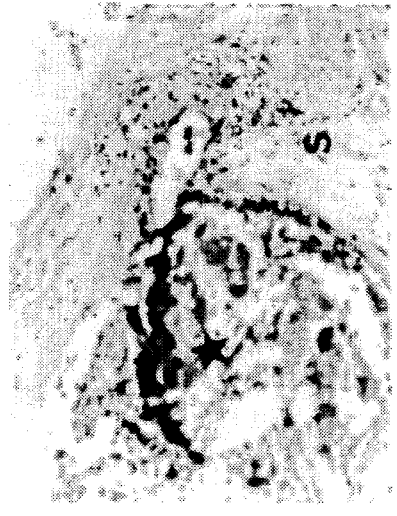

FIG. 13A is a bright-field photomicrograph where the tissue section is comedo carcinoma in situ (*, ×100) with segmental ST3 gene expression in surrounding stromal cells (S).

FIG. 13B is a dark-field photomicrograph of the comedo carcinoma in situ that is shown in FIG. 13A.

FIG. 13C is a higher-power view (×400) of the tissue section shown in FIG. 13A, where arrows indicate fibroblastic cells expressing ST3 transcripts. Note that were the basement membrane is thickened (rounded arrow), there is no ST3-expressing fibroblastic cells.

Figure 13D:
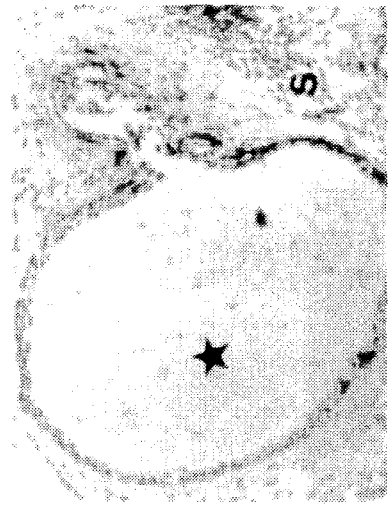

FIG. 13D is a bright-field photomicrograph of muciparous ductal carcinoma in situ (*, ×100) with segmental ST3 gene expression in surrounding stromal cells (S).

FIG. 13E is a dark-field photomicrograph of the tissue section shown in FIG. 13D.

FIG. 13F is a higher-power view (×400) of the tissue section shown in FIG. 13D, where arrows indicate fibroblastic cells expressing ST3 transcripts in a tumoral area where basement membrane integrity is questionable.

Figure 13I:
Figure 13L:
Figure 13H:
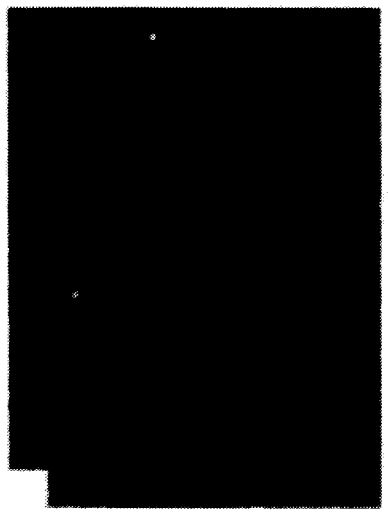
Figure 13K:
Figure 13G:
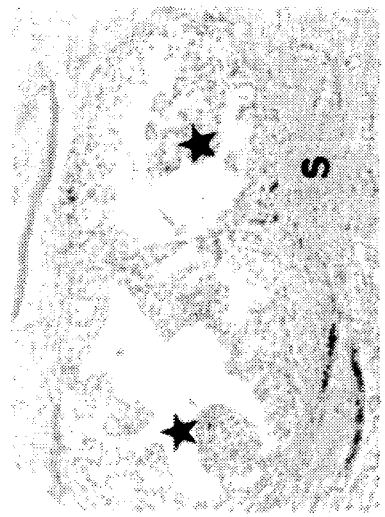

FIG. 13G is a bright-field photomicrograph of micropapillary ductal carcinoma in situ (*, ×100) with focal ST3 gene expression in surrounding stromal cells (S).

FIG. 13H is a dark-field photomicrograph of the tissue section shown in FIG. 13G.

FIG. 13I is a bright-field photomicrograph of three cribriform ductal carcinoma in situ (*, ×100), two of said carcinomas having circumferential ST3 gene expression in surrounding stromal cells (S) and one with no ST3 gene expression.

Figure 13J:

FIG. 13J is a dark-field micrograph of the tissue section shown in FIG. 13I.

FIG. 13K is a bright-field photomicrograph of two capillary ductal carcinomas in situ (*, ×100), one having ST3 gene expression in the surrounding stromal cells (S), and one having no ST3 gene expression. Note the high level of ST3 transcripts in the stromal cells adjacent to the area of invasive carcinoma (C).

FIG. 13L is a dark-field micrograph of the same tissue section shown in FIG. 13K.

Figure 13O:
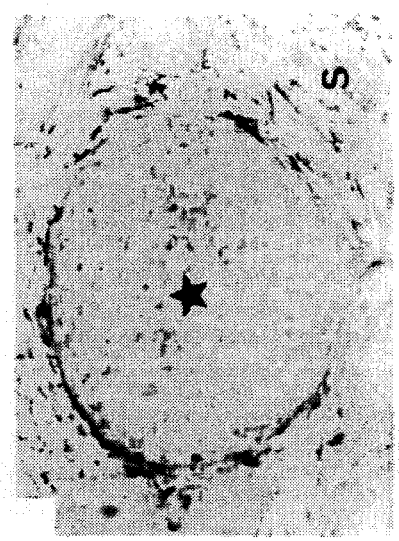
Figure 13N:
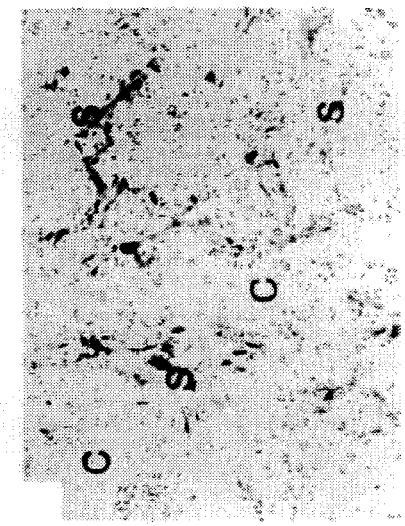
Figure 13M:
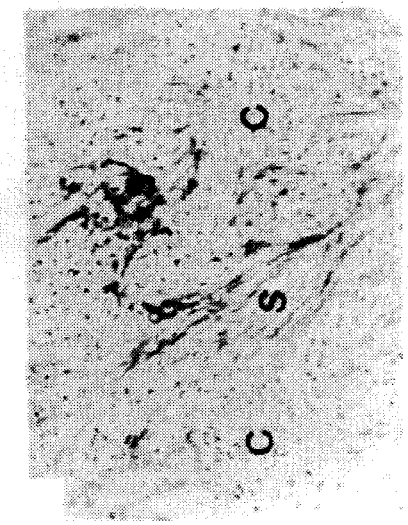

FIG. 13M–FIG. 13O are photomicrographs of frozen tissue sections (×200) that have been subject to indirect immunoperoxydase staining of stromelysin-3 (ST3) protein.

FIG. 13M is a photomicrograph of frozen invasive carcinoma (C) after immunohistochemical analysis with polyclonal antibody 349.

FIG. 13N is a photomicrograph of frozen invasive carcinoma (C) after immunohistochemical analysis with monoclonal antibody 5ST-4A9-3.

FIG. 13O is a photomicrograph of frozen in situ ductal carcinoma (*, comedo type) after immunohistochemical analysis with monoclonal antibody 5ST-4A9-3.

In each of FIGS. 13M, 13N, and 13O, ST3 is exclusively detected in elongated fibroblast-like cells tumoral stroma (S) surrounding neoplastic cells.

FIG. 14A depicts northern blot analysis of stromelysin-3 RNA in breast tissue and breast cancer of metastatic lymph nodes. ST3 RNA has been detected in all the evasive ductal and lobular breast carcinomas so far tested by northern blot analysis, but not in the normal breast samples tested in parallel.

FIG. 14B also depicts northern blot analysis of stromelysin-3 RNA in breast cancer metastatic lymph nodes. 8 μM of total RNA was loaded in each lane. Primary tumors (invasive ductal carcinomas) and metastatic lymph nodes in each vertical lane were obtained from the same patient. Hybridization was performed with [$^{32}$P]-labeled stromelysin-3 cDNA, and the blots were rehybridized with [$^{32}$P]-labeled 36B4 cDNA (Masiakowski et al., *Nucleic Acid Res.* 10:7895–7903 (1982)), to check for RNA loading and transferring each lane. Autoradiography was for two days.

FIG. 15A–FIG. 15H are photomicrographs of paraffin-embedded tissue sections (×100) stained with hematoxylin, after in situ hybridization with [$^{35}$S]-labeled stromelysin-3 antisense RNA.

Figure 15A:
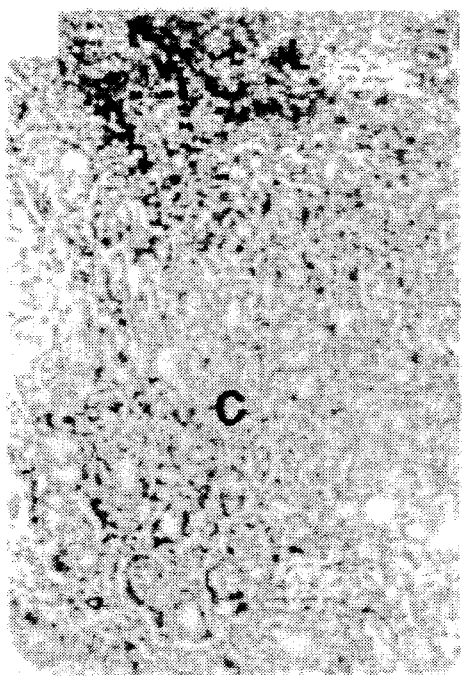

FIG. 15A is a bright-field photomicrograph of a lymph node tissue section.

Figure 15B:
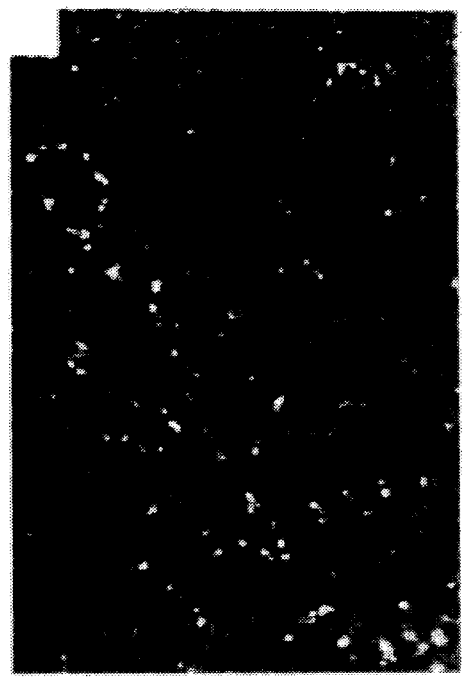

FIG. 15B is a dark-field photomicrograph of the same section shown in FIG. 15A.

Figure 15C:
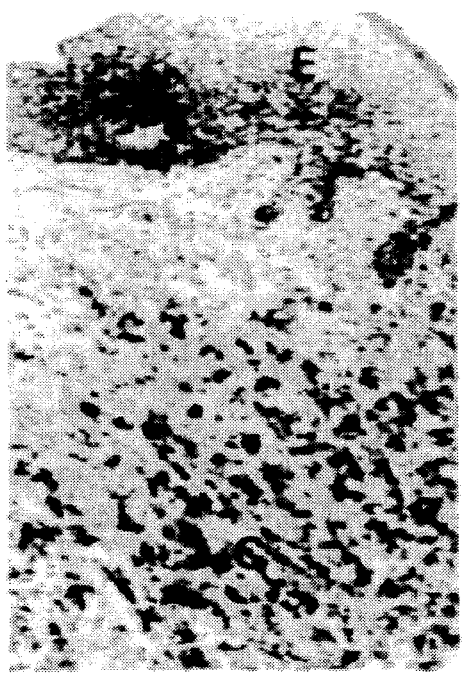

FIG. 15C is a bright-field photomicrograph of a skin tissue sample.

Figure 15D:

FIG. 15D is a dark-field photomicrograph of the same section shown in FIG. 15C.

Figure 15E:
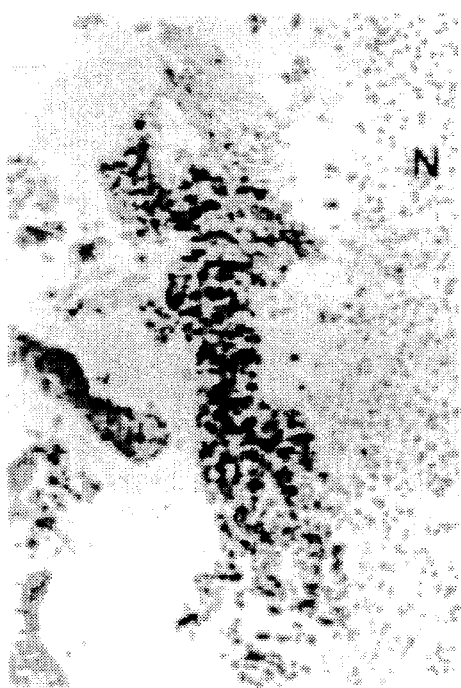

FIG. 15E is a bright-field photomicrograph of a pleura tissue section.

Figure 15F:
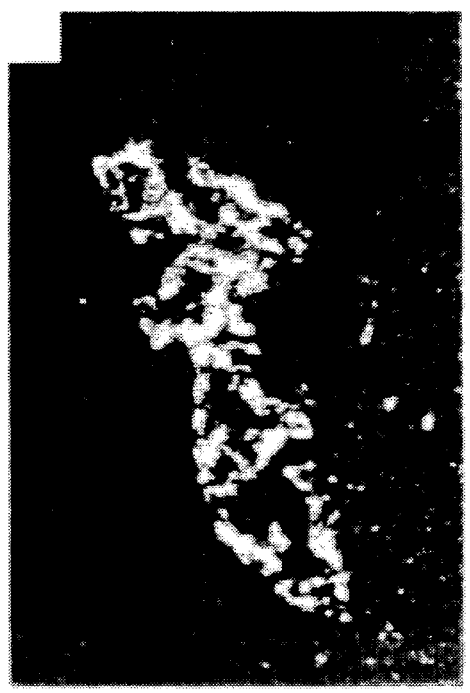

FIG. 15F is a dark-field photomicrograph of the same section shown in FIG. 15E.

Figure 15G:
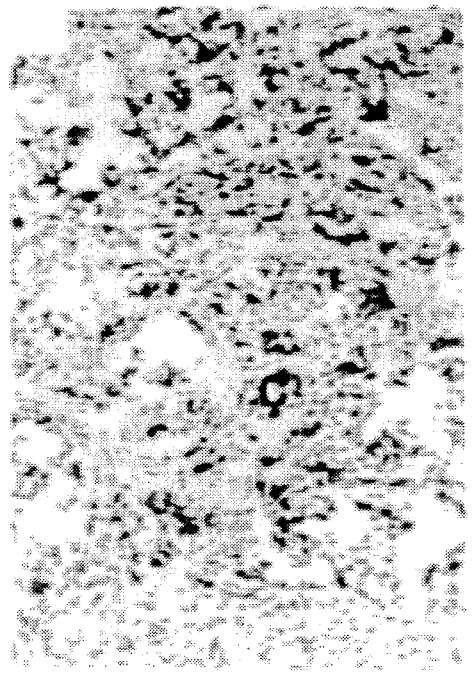

FIG. 15G is a bright-field photomicrograph of a bone metastases tissue section.

Figure 15H:
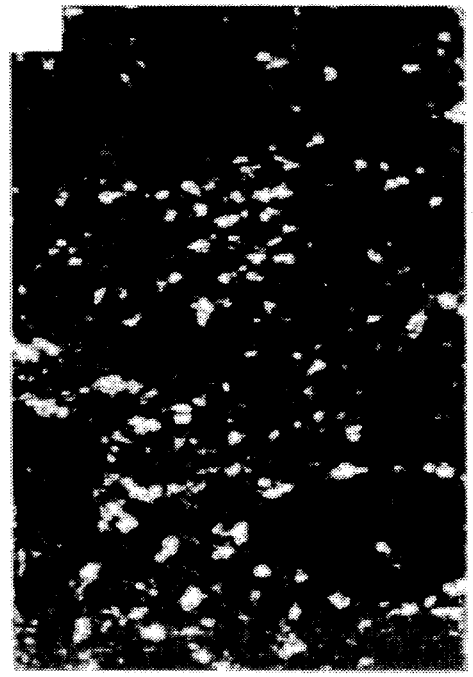

FIG. 15H is a dark-field photomicrograph of the same section shown in FIG. 15G.

For each of FIGS. 15A–15H, M refers to a metastatic tumor; L refers to lymphocytes; E refers to epiderm; N refers to normal pleura. ST3 transcripts are exclusively detected in fibroblastic cells of tumor stroma surrounding neoplastic cells. Autoradiography was for four weeks.

FIG. 16A–FIG. 16I are photomicrographs of serial paraffin-embedded tissue sections (×100) of ductal carcinomas stained with hematoxylin, after in situ hybridization with [$^{35}$S]-labeled antisense RNA probes. S, stroma; *, in situ (comedo); C, invasive carcinoma; N, subnormal breast; V, blood vessel.

Figure 16C:
Figure 16B:
Figure 16A:
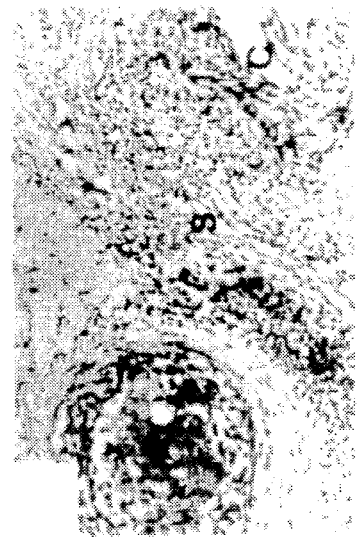

FIG. 16A is a bright-field photomicrograph of ductal carcinoma serial section.

FIG. 16B is a dark-field photomicrograph of the same section hybridized with stromelysin-3.

FIG. 16C is dark-field micrograph of the same serial section hybridized with 72-kDa type IV collagenase antisense RNAs. ST3 transcripts are detected in fibroblastic cells of tumor stroma immediately surrounding cancer cells, while type IV collagenase transcripts are observed in fibroblastic cells distributed throughout the stroma.

Figure 16F:
Figure 16E:
Figure 16D:
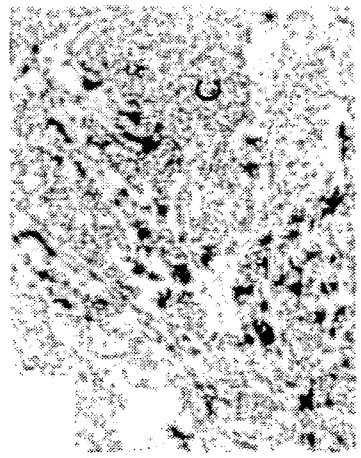

FIG. 16D is a bright-field photomicrograph of a serial tissue section of ductal carcinoma.

FIG. 16E is a dark-field photomicrograph of the same serial section as FIG. 16D after hybridization with ST3.

FIG 16F is a dark-field photomicrograph of the same serial section as shown in FIG. 16D after hybridization with urokinase antisense RNAs.

Figure 16I:
Figure 16H:
Figure 16G:
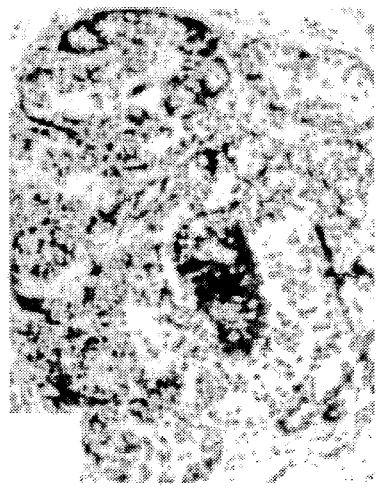

FIG. 16G is a bright-field photomicrograph of a serial ductal carcinoma tissue section.

FIG. 16H is a dark-field photomicrograph of the same serial section as shown in FIG. 16G after hybridization with ST3.

FIG. 16I is a dark-field photomicrograph of the same serial section shown in FIG. 16G after hybridization with urokinase antisense RNAs.

For FIGS. 16A–16I, ST3 and urokinase transcripts are detected in the same fibroblastic cells of tumor stroma (S) immediately surrounding invasive (C) and in situ (*) neoplastic cells. For FIG. 16C, exposure time was for two weeks. For FIG. 16B, FIG. 16E and FIG. 16F, exposure time was for four weeks. For FIG. 16H and FIG. 16I, exposure time was for six weeks.

Figure 17:
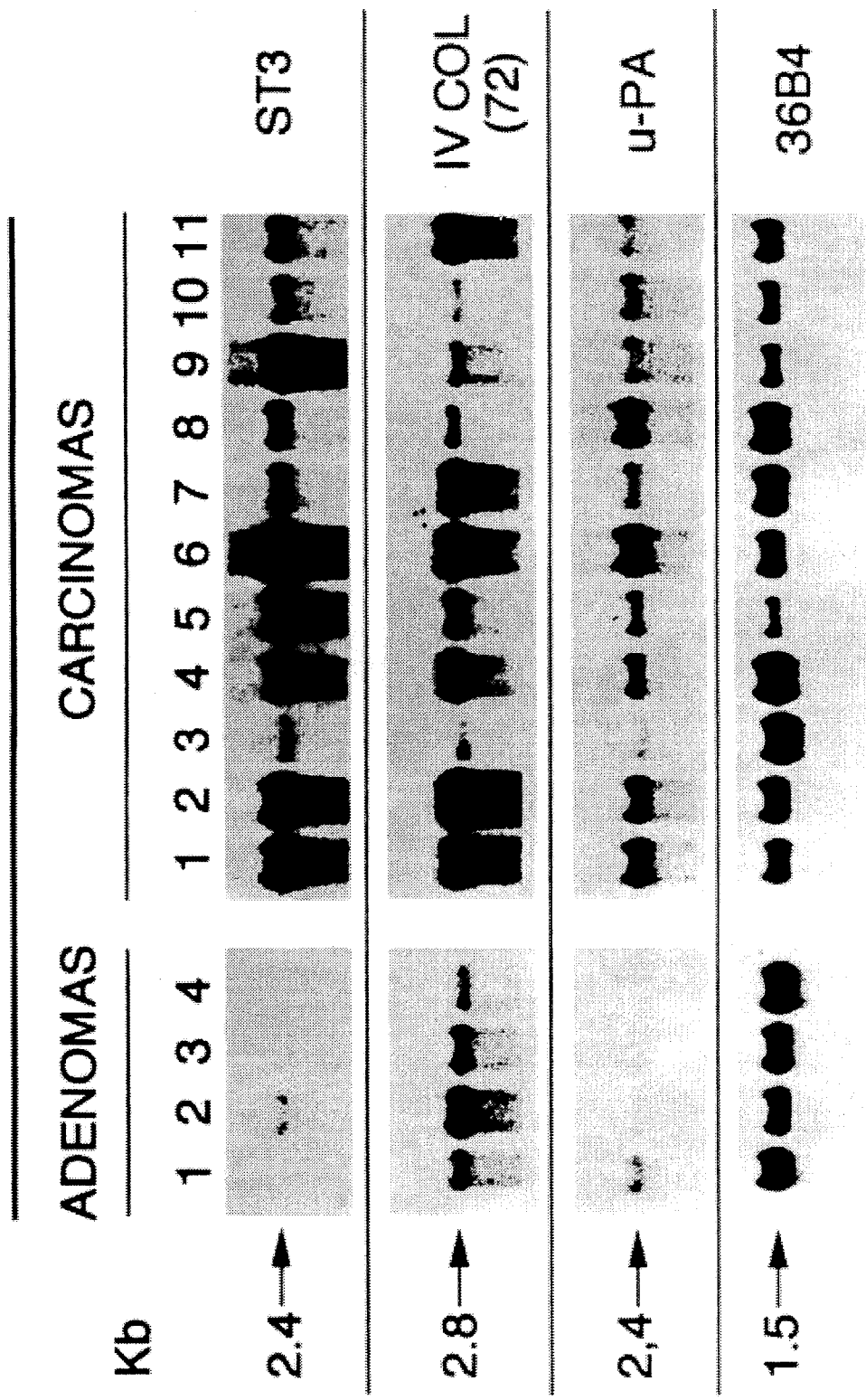

FIG. 17 depicts a comparative nothern blot analysis of stromalysin-3 72-kDa type IV collagenase and urokinase RNAs in breast tumors. 8 μM of total RNA from four fibroid adenomas and 11 invasive carcinomas (1–10, ductal and 11, lobular) were loaded in each lane. Hybridization was successfully performed on the same blot [$^{32}$P]-labeled stromalysin-3 [ST3], 72-kDa type IV collagenase [IV COL (72)] and urokinase (u-PA) cDNAs. Hybridization with [$^{32}$P]-labeled 36B4 cDNA (Masiakowski et al., *Nucleic Acid Res.* 10:7895–7903 (1982)) was made to check for RNA loading and transfer in each lane. Autoradiography was for two days (ST3), one day (IV COL) and four days (u-PA).

DETAILED DESCRIPTION OF THE INVENTION

In a first aspect, the present invention provides a process for the diagnosis of invasive cancer, especially breast, head and neck, and skin carcinomas, comprising the detection of either stromelysin-3, or a nucleotide sequence encoding stromelysin-3.

In an alternative aspect, the present invention provides the use of an agent to interfer with the synthesis or activity of stromelysin-3 in the treatment or prophylaxis of invasive cancer, especially breast, head and neck, and skin carcinomas.

It will be appreciated that metastatic tumors are invasive, but that invasive tumors are not necessarily metastatic (for example basal cell skin carcinomas).

As expression of the stromelysin-3 gene is specific to regions of ECM degradation and apparently encodes a metalloproteinase, it is assumed that its ECM degrading activity is crucial to tumor progression into metastasis. Expression of stromelysin-3 by the stromal cells is likely to break down an important part of the ECM, thereby allowing cancerous cells to migrate away from the parent tumor.

Accordingly, any agent which can affect the activity of stromelysin-3 will have an effect on metastasis. Such agents will suitably be those which either prevent synthesis of the protein, prevent maturation of the protein, or alter the activity of the enzyme, either by blocking or by altering its activity.

Expression of the stromelysin-3 gene was found to be, in the first instance, diagnostic of breast cancer in the metastatic phase. In fact, this result was achieved by the detection of mRNA in a variety of resetted tumors. Breast cancer was chosen, as this is responsible for the highest death rate, by cancer, in the non-smoking female population.

Stromelysin-3 is a novel protein almost certainly belonging to the MMP family, and is associated with invasive breast carcinomas, irrespective of their hormonal status.

The members of the MMP family require an activation step, which may be associated with removal of the pre- and pro- sequences, to become active. The amino acid sequence of pro- and mature stromelysin-3 is notably different from those of the previously characterized MMPs, and may exhibit distinct properties regarding maturation, activation and specificity for ECM components.

The stromelysin-3 gene is expressed by all primary invasive breast carcinomas, by some of their metastases, and in tissues in which extensive ECM remodelling is known to occur (uterus, placenta and limb bud) analyzed for such expression, but not in breast fibroadenomas and normal adult tissues, suggesting that the stromelysin-3 gene product plays an important role in breast cancer progression. Also in agreement with this concept, the stromelysin-3 gene is not expressed in most in situ breast carcinomas, with the exception of in situ carcinomas of the comedo type (Example 11), which are usually considered as preinvasive lesions and are often associated with microinvasion. Thus the presence of stromelysin-3 RNA transcripts in other than the low concentrations found elsewhere in the body, other than uterus or placenta, is diagnostic of a metastatic cancer or of a cancer with a high risk of becoming invasive.

Stromelysin-3 may be involved in the lyric processes which are likely to be associated with invasive tumor growth. Alternatively, it is possible that stromelysin-3 could also play a role in the formation of desmoplasia, which is associated with most invasive breast cancer lesions, and may represent a host reaction to prevent further malignant cell spread (Ahmed, A., *Pathol. Annu.* 25(Pt2):237–286 (1990)). In such an instance, enhancement of stromelysin-3 activity would be advantageous.

Further, the restricted expression of the stromelysin-3 gene in stromal fibroblasts immediately surrounding the neoplastic cell islands is strikingly in contrast to collagenase IV, another metalloproteinase known to be associated with the malignant conversion of some tumorigenic cells, and cathepsin D, a lysosomal aspartyl protease whose expression is increased in breast carcinomas, both of which are expressed, not in the fibroblasts, but in the neoplastic epithelial cells of breast cancers (Monteagudo et al., *Am. J. Pathol.* 136:585–592 (1990); Garcia et al., *Steroid Biochem.* 27:439–445 (1987)).

To identify the novel breast cancer marker, a cDNA library was constructed, and substracted with poly (A+)

RNA from a fibroadenoma source. By this process, the cDNA library was enriched for sequences characteristic of metastatic cancers.

A number of clones was grown up and screened using probes derived from poly($A^+$) RNA from metastatic tumors and from fibroadenomas. Those clones which bound more greatly to the probes derived from metastatic cancer poly($A^+$) RNA were then grown up further.

Of the clones generated in this manner, one was found to be differentially expressed to the extent that high rates of expression were only found in malignant breast and pharyngeal cancers, head, neck, and skin (squamous and basal cell type) carcinomas, as well as in the uterus and placenta, in all of which there is a breaking down of the ECM, which, when associated with cancer, allows cancerous cells to spread around the body (metastasis).

In the case of the uterus and the placenta, breakdown of the ECM occurs naturally, whilst the same event elsewhere is likely to be characteristic of tumor growth.

It is also interesting to note that expression of the stromelysin-3 gene was found in interdigital differentiation during limb budding in the foetus, which is associated with breakdown of the ECM.

Characterization of the cDNA sequence illustrated that there was an open reading frame. Comparison of the encoded protein sequence with a known library established that the protein belonged to a family known to break down the ECM. Although the sequence of stromelysin-3 bears less similarity to the other members of its family than any of the other members bear to each other, it does, nevertheless, present a number of characteristic regions which serve to identify the nature of the enzyme. Accordingly, the protein has been named stromelysin-3, although it may be a collagenase, or may break down a different constituent of the ECM altogether.

Construction of nucleotide probes to establish the occurrence of stromelysin-3 mRNA revealed a tissue distribution as described above, and also enabled photomicrographs to exactly locate the areas of expression of the stromelysin-3 gene by labelling.

An analysis of the photomicrographs generated by this method showed, somewhat surprisingly, that the stromelysin-3 gene was not expressed in the cancerous cells itself, but in the surrounding stroma. In addition, the stroma did not exhibit any evidence of stromelysin-3 mRNA when the basement membrane of the tumor was still intact (see FIG. 6A–FIG. 6I). The stromelysin-3 gene is expressed by all primary invasive breast carcinomas, by some of their metastases nodes, and in tissues in which extensive ECM remodelling is known to occur (uterus, placenta and limb bud) analyzed for such expression, but not in breast fibroadenomas and normal adult tissues, suggesting that the stromelysin-3 gene product plays an important role in breast cancer progression. Also in agreement with this concept, the stromelysin-3 gene is not expressed in most in situ breast carcinomas, with the exception of in situ carcinomas of the comedo type (Example 11), which are usually considered as preinvasive lesions and are often associated with microinvasion. Stromelysin-3 always occurs in the stroma of metastatic cancers, and does not occur in the stroma of in situ primary tumors (tumors still having a basement membrane and which are non-invasive). Thus the presence of stromelysin-3 RNA transcripts in other than the low concentrations found elsewhere in the body, other than uterus or placenta, is diagnostic of a metastatic cancer or of a cancer with a high risk of becoming invasive.

Furthermore, expression of the stromelysin-3 gene was not detected in any ER-positive or negative breast cancer cell lines, even though some of them are known to secrete and possess receptors for EGF/TGF-α and FGF (factors which are implicated in expression of the stromelysin-3 gene).

Accordingly, standard detection techniques applied to stromelysin-3, its precursors or its coding nucleotide sequences may be used to diagnose a metastatic cancer, or to confirm that a primary tumor has not yet reached the fatal metastatic phase.

Such techniques may include detection with nucleotide probes, such as in the manner described above, or may comprise detection of the stromelysin-3 protein by, for example, antibodies or their equivalent.

The nucleotide probes may be any that will hybridize more strongly to the sequence shown in the accompanying FIG. 2A and FIG. 2B than to other naturally occurring sequences. Types of probe include cDNA, riboprobes, synthetic oligonucleotides and genomic probes. The type of probe used will generally be dictated by the particular situation, such as riboprobes for in situ hybridization, and cDNA for Northern blotting, for example. The most preferred probes are those which correspond to the negative strand of the cDNA of FIG. 2A and FIG. 2B. It is also possible to provide probes which recognize introns located within the stromelysin-3 gene, but this is not necessarily as reliable as detecting RNA transcripts.

Detection of the stromelysin-3 encoding gene, per se, will generally serve no purpose in diagnosis, but other forms of assay to detect transcripts and other expression products will generally be useful. The probes may be as short as is required to differentially recognize stromelysin-3 mRNA transcripts, and may be as short as, for example, 15 bases.

The form of labelling of the probes may be any that is appropriate, such as the use of radioisotopes, for example, $^{32}P$ and $^{35}S$. Labelling with radioisotopes may be achieved, whether the probe is synthesized chemically or biologically, by the use of suitably labelled bases. Other forms of labelling may include enzyme or antibody labelling such as is characteristic of ELISA, but detection of mRNA transcripts by labelled probes will generally be by way of X-radiography.

Detection of RNA transcripts may be achieved by Northern blotting, for example, wherein a preparation of RNA is run on a denaturing agarose gel, and transferred to a suitable support, such as activated cellulose, nitrocellulose or glass or nylon membranes. Radiolabelled cDNA or RNA is then hybridized to the preparation, washed and analyzed by autoradiography.

In situ hybridization visualization may also be employed (Example 6), wherein a [$^{35}S$]-labelled antisense cRNA probe is hybridized with a thin section of a biopsy sample, washed, cleaved with RNase and exposed to a sensitive emulsion for autoradiography. The samples may be stained with haematoxylin to demonstrate the histological composition of the sample, and dark field imaging with a suitable light filter shows up the developed emulsion.

Immunohistochemistry may be used to detect expression of stromelysin-3 in a biopsy sample. A suitable antibody is brought into contact with, for example, a thin layer of cells, washed, and then contacted with a second, labelled antibody. Labelling may be by enzyme, such as peroxidase, avidin or by radiolabelling. Chromogenic labels are generally preferable, as they can be detected under a microscope.

More generally preferred is to detect the protein by immunoassay, for example by ELISA or RIA, which can be extremely rapid. Thus, it is generally preferred to use antibodies, or antibody equivalents, to detect stromelysin-3, but use of a suitably labelled stromelysin-3 substrate may also be advantageous.

It may not be necessary to label the substrate, provided that the product of the enzymatic process is detectable and characteristic in its own right (such as hydrogen peroxide for example). However, if it is necessary to label the substrate, then this may also comprise enzyme labelling, labelling with radioisotopes, antibody labelling, fluorescent marker labelling or any other suitable form which will be readily apparent to those skilled in the art.

Most preferred for detecting stromelysin-3 expression is the use of antibodies. Antibodies may be prepared as described below, and used in any suitable manner to detect expression of stromelysin-3.

Antibody-based techniques include ELISA (enzyme linked immunosorbent assay) and RIA (radioimmunoassay). Any conventional procedures may be employed for such immunoassays. The procedures may suitably be conducted such that: a stromelysin-3 standard is labelled with a radioisotope such as $^{125}$I or $^{35}$S, or an assayable enzyme, such as horseradish peroxidase or alkaline phosphatase and, together with the unlabelled sample, is brought into contact with the corresponding antibody, whereon a second antibody is used to bind the first and radioactivity or the immobilized enzyme assayed (competitive assay); alternatively, stromelysin-3 in the sample is allowed to react with the corresponding immobilized antibody, radioisotope- or enzyme-labelled anti-stromelysin-3 antibody is allowed to react with the system and radioactivity or the enzyme assayed (ELISA-sandwich assay). Other conventional methods may also be employed as suitable.

The above techniques may be conducted essentially as a "one-step" or "two-step" assay. The "one-step" assay involves contacting antigen with immobilized antibody and, without washing, contacting the mixture with labeled antibody. The "two-step" assay involves washing before contacting the mixture with labeled antibody. Other conventional methods may also be employed as suitable.

Enzymatic and radio-labelling of stromelysin-3 and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labelling are not particularly limited, but may be selected from the members of the oxidase group, for example. These catalyze the production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labelled antibody with the substrate under controlled conditions well-known in the art.

Other techniques may be used to detect stromelysin-3 according to preference. One such is Western blotting (Towbin et at., *Proc. Nat. Acad. Sci.* 76:4350 (1979)), wherein a suitably treated sample is run on an SDS PAGE gel before being transferred to a solid support, such as a nitrocellulose filter. Anti-stromelysin-3 antibodies (unlabelled) are then brought into contact with the support and assayed by a secondary immunological reagent, such as labelled protein A or anti-immunoglobulin (suitable labels including $^{125}$I, horseradish peroxidase and alkaline phosphatase).

Samples for diagnostic purposes may be obtained from any relevant site. A sample obtained direct from the tumor, such as the stroma or cytosol, may be ideal, but it may also be appropriate to obtain the sample from blood, for example. However, if the sample is derived from blood, highly sensitive assays may be required, as the amount of stromelysin-3 would then be diluted through the bloodstream. Such diagnosis may be of particular importance in monitoring progress of a patient, such as after surgery to remove a tumor. If a reference reading is taken after the operation, then another taken at regular intervals, any rise could be indicative of a relapse, or possibly a metastasis. The taking of such readings may need to take into account activity in the uterus, for example.

Anti-stromelysin-3 antibodies may also be used for imaging purposes. Besides enzymes, other suitable labels include radioisotopes, iodine ($^{125}$I, $^{121}$I), carbon ($^{14}$C), salphee ($^{35}$S), tritium ($^{3}$H), indium ($^{112}$In), and technetium ($^{99m}$Tc), fluorescent labels, such as fluorescein and rhodamine, and biotin.

However, for in vivo imaging purposes, the position becomes more restrictive, as antibodies are not detectable, as such, from outside the body, and so must be labelled, or otherwise modified, to permit detection.

Markers for this purpose may be any that do not substantially interfere with the antibody binding, but which allow external detection. Suitable markers may include those that may be detected by X-radiography, NMR or ESR. For X-radiographic techniques, suitable markers include any radioisotope that emits detectable radiation but that is not overtly harmful to the patient, such as barium or caesium, for example. Suitable markers for NMR and ESR generally include those with a detectable characteristic spin, such as deuterium, which may be incorporated into the antibody by suitable labelling of nutrients for the relevant hybridoma, for example.

In the case of in vivo imaging methods, an antibody or antibody fragment which has been labelled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the subject (such as a human) to be examined.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99m. The labelled antibody or antibody fragment will then preferentially accumulate at the location of cells which contain stromelysin-3. The labelled antibody or antibody fragment can then be detected using known techniques.

For a general discussion of this technological area, see S. W. Burchiel et at., "Immunopharmacokinetics of Radiolabelled Antibodies and Their Fragments" (Chapter 13 in *Tumor Imaging: The Radiochemical Detection of Cancer*, eds., S. W. Burchiel and B. A. Rhodes, Masson Publishing Inc. (1982)).

The antibodies may be raised against either a peptide of stromelysin-3 or the whole molecule. Such a peptide may be presented together with a carrier protein, such as an albumin, to an animal system or, if it is long enough, say 25 amino acid residues, without a carrier. Human antibodies are unlikely to be able to recognize stromelysin-3, as this protein will represent a self protein.

As used herein, the term "peptide" means any molecule comprising 2 or more amino acids linked via a peptide bond. As such, the term includes oligopeptides, polypeptides and proteins.

Polyclonal antibodies generated by the above technique may be used direct, or suitable antibody producing cells may be isolated from the animal and used to form a hybridoma by known means (Kohler and Milstein, *Nature* 256:795 et seq. (1975)). Selection of an appropriate hybridoma will also be apparent to those skilled in the art, and the resulting antibody may be used in a suitable assay to identify stromelysin-3.

Antibodies, or their equivalents, may also be used in accordance with the present invention for the treatment or prophylaxis of metastatic cancers. Administration of a suitable dose of the antibody may serve to block production, or to block the effective activity of stromelysin-3, and this may provide a crucial time window in which to treat the malignant growth.

Prophylaxis may be appropriate even at very early stages of the disease, as it is not known what actually leads to metastasis in any given case. Thus, administration of the antibodies, their equivalents, or factors, such as TIMPs (naturally occurring compounds which regulate the MMPs—tissue inhibitors of metalloproteinases), which interfere with stromelysin-3 activity, may be effected as soon as cancer is diagnosed, and treatment continued for as long as is necessary, preferably until the threat of the disease has been removed.

A preferred form of treatment is to employ the so-called magic bullet technique, where a suitable toxin is attached to the antibodies which then target the area of the tumor. Such toxins are well known in the art, and may comprise toxic radioisotopes, heavy metals, enzymes and complement activators, as well as such natural toxins as ricin which are capable of acting at the level of only one or two molecules per cell. It may also be possible to use such a technique to deliver localized doses of hormone antagonists or any other suitable physiologically active compounds, which may be used, for example, to treat cancers.

It will be appreciated that antibodies for use in accordance with the present invention, whether for diagnostic or therapeutic applications, may be monoclonal or polyclonal as appropriate. Antibody equivalents of these may comprise: the Fab' fragments of the antibodies, such as Fab, Fab', F(ab')$_2$ and Fv; idiotopes; or the results of allotope grafting (where the recognition region of an animal antibody is grafted into the appropriate region of a human antibody to avoid an immune response in the patient), for example. Other suitable modifications and/or agents will be apparent to those skilled in the art.

In addition to using antibodies to inhibit or remove stromelysin-3, it may also be possible to use other forms of inhibitor. Such inhibitors may be general (for ECM degrading enzymes, for example), or specific for stromelysin-3. Tissue inhibitors of metalloproteinases (TIMPs) are known to exist, and it is extremely likely that there is a specific TIMP for stromelysin-3. Such a TIMP is easily identifiable by standard techniques.

Synthetic inhibitors of stromelysin-3 may also be manufactured, and these will generally correspond to the area of the substrate affected by the enzymatic activity. It is generally preferred that such inhibitors correspond to a frozen intermediate between the substrate and the cleavage products, but it is also possible to provide a sterically hindered version of the binding site, or a version of the binding site which will, itself, irreversibly bind to stromelysin-3. Other suitable inhibitors will be apparent to the skilled person.

Other methods for blocking stromelysin-3 activity may also be employed. These may constitute denaturing agents, for example, although these tend to be non-specific and could only be adequately employed if they could be targeted, such as by the use of specific antibodies. Other forms of stromelysin-3 blocking activity could be effected by blocking the progress from pre-proprotein through to protein. This process provides several target stages, and it is only necessary to identify a stage which can be independently blocked so as not to affect other vital enzymes, or which can again be targeted.

It may also be possible to use peptides or other small molecules to selectively recognize a tertiary structure on stromelysin-3, thereby blocking its enzymic activity. Such an activity blocker need not necessarily bind the active site, but may serve to alter or freeze the tertiary structure of stromelysin-3, destroying, suspending or altering its activity. The blocker also need not necessarily act by itself, but may be linked to another molecule for this purpose, or may serve as a recognition site for a suitable inactivating agent.

Our studies have demonstrated that the occurrence of type I collagenase and 92 kD type IV collagenase mRNAs is exclusively associated with malignant tumors, although the reverse does not always hold (i.e. tumors are not always associated with these proteins).

There is apparently a parallel between the expression of the stromelysin-3 gene and that of the tenascin gene, in invasive breast carcinomas. The ECM glycoprotein tenascin (Chiquet-Ehrismann et al., *Cell* 47:131–139 (1986)) appears to play an essential role in epithelial mesenchyme cell interactions and cell migration during normal development, including that of the mammary gland during organogenesis.

Tenascin has consistently been found to be over-expressed in the fibrous stroma of malignant breast tumors, and appears to be induced in a similar manner to stromelysin-3. When compared with fibronectin, tenascin is a poor substrate for attachment of mammary tumor epithelial cells, suggesting that it may allow them to become invasive.

Thus, stromelysin-3 may act in concert with tenascin during the invasive phase of breast cancer. Stromelysin-3 and tenascin may also be co-expressed during embryogenesis in the regions where epithelium-mesenchyme interactions are known to play an important role, and where cell migration is taking place.

Accordingly, the present invention also provides a process for the diagnosis of metasiatic cancer as defined above, further comprising the detection of any of the foregoing proteins, or a nucleotide sequence encoding them.

The invention also provides a use in the treatment or prophylaxis of metastatic cancer, further comprising the use of an agent to bind any of the foregoing proteins.

The present invention further provides a nucleotide sequence encoding all or part of stromelysin-3. The sequence of stromelysin-3 is preferably that shown in FIG. 2A and FIG. 2B of the accompanying drawings, whilst the nucleotide sequence is also preferably that shown in FIG. 2A and 2B. However, it will be appreciated that the nucleotide sequence may be substantially different from that shown in the Figure, due to degeneracy in the genetic code, provided that it still encodes at least a part of stromelysin-3.

The necessary sequence may vary even further, according to the use to which it is to be put. If it is intended for use to detect RNA transcripts in biological samples, then it will usually be preferable that it more nearly corresponds to the sequence given in FIG. 2A and FIG. 2B. However, the sequence may still vary, provided that hybridization is possible under the selected conditions of stringency.

A probe may be reverse-engineered by one skilled in the art from the peptide sequence of FIG. 2A and FIG. 2B. However use of such probes may be limited, as it will be appreciated that any one given reverse-engineered sequence will not necessarily hybridize well, or at all with any given complementary sequence reverse-engineered from the same peptide, owing to the degeneracy of the genetic code. This is a factor common in the calculations of those skilled in the art, and the degeneracy of any given sequence is frequently so broad as to yield a large number of probes for any one sequence.

If the nucleotide sequence is required for expression of a stromelysin-3 peptide or entire enzyme, then there may be a considerably greater leeway, both as described above with respect to the genetic code, and also to the fact that some amino acid sequence of stromelysin-3 may be varied without significant effect on the structure or function of the enzyme.

If such differences in sequence are contemplated, then it should be borne in mind that there will be critical areas on the molecule which determine activity. Such areas will usually comprise residues which make up the binding site, or which form tertiary structures which affect the binding site. In general, it is possible to replace residues which form the tertiary structure, provided that residues performing a similar function are used. In other instances, the type of residue may be completely unimportant.

Accordingly, the present invention also includes any variants and mutants on the sequence which still show substantial stromelysin-3 activity, or which exhibit characteristic regions of stromelysin-3 for use in generating antibodies, for example. Such variants and routants include deletions, additions, insertions, inversions, repeats and typesubstitutions (for example, substituting one hydrophilic residue for another, but not strongly hydrophilic for strongly hydrophobic as a rule). Small changes will generally have little effect on activity, unless they are an essential part of the molecule, and may be a side-product of genetic manipulation, for example, when generating extra restriction sites, should such be desired. Modification may also include replacement of one or more of the residues with any other suitable residue, and such replacement may either be 1:1 or any other suitable ratio, greater or less than unity.

Spot mutations and other changes in the coding sequence may be effected to add or delete restriction sites, for example, to otherwise assist in genetic manipulation/expression, or to enhance or otherwise conveniently to modify the stromelysin-3 molecule.

It will also be appreciated that a stromelysin-3 equivalent will be found in other animals, especially mammals, and sequence information from such sources can be of particular importance to elucidate the conserved regions of the stromelysin-3 molecule. For example, the corresponding sequence in the mouse is ≈80% conserved, including such as the 10 amino acid sequence in the prodomain characteristic of stromelysin-3 (Lefebvre et al., *J. Cell Biol.* 119:997–1002 (1992)). It will also be appreciated that animal sequences corresponding to human stromelysin-3 sequences will be readily detectable by methods known in the art and described above, and such sequences and their peptides, as well as mutants and variants thereof, form a part of the invention.

The sequences of the invention may also be engineered to provide restriction sites, if desired. This can be done so as not to interfere with the peptide sequence of the encoded stromelysin-3, or may interfere to any extent desired or necessary, provided that the final product has the properties desired.

As stated above, although hybridization can be an unreliable indication of sequence homology, preferred sequences will generally be those showing in excess of 50%, preferably 70% and more preferably 80% homology with the sequence of FIG. 2A and FIG. 2B.

As with the other metalloproteinases, stromelysin-3 is originally expressed as a pre-proenzyme. Thus, two stages of cleavage are observed in vivo. Cleavage is not necessarily a requirement for in vitro expression, and it may be possible for *E. coli*, for example, to express the mature protein.

Where it is desired to express stromelysin-3 or a characteristic peptide thereof, any suitable system can be used. The general nature of suitable vectors, expression vectors and constructions therefor will be apparent to those skilled in the art.

By "characteristic" is meant any peptide which has a sequence unique to stromelysin-3. Such a sequence may be important to stromelysin-3 activity, or may just be a sequence not found in other peptides. However, sequences important to stromelysin-3 activity are generally preferred, as these are more likely to be conserved within a population.

Suitable expression vectors may be based on phages or plasmids, both of which are generally host-specific, although these can often be engineered for other hosts. Other suitable vectors include cosmids and retroviruses, and any other vehicles, which may or may not be specific for a given system. Again, control sequences, such as recognition, promoter, operator, inducer, terminator and other sequences essential and/or useful in the regulation of expression, will be readily apparent to those skilled in the art, and may be associated with the natural stromelysin-3 sequence or with the vector used, or may be derived from any other source as suitable. The vectors may be modified or engineered in any suitable manner.

Correct preparation of nucleotide sequences may be confirmed, for example, by the method of Sanger et al. (*Proc. Natl. Acad. Sci. USA* 74:5463–7 (1977)).

A cDNA fragment encoding the stromelysin-3 of the invention may easily be inserted into a suitable vector. Ideally, the receiving vector has suitable restriction sites for ease of insertion, but blunt-end ligation, for example, may also be used, although this may lead to uncertainty over reading frame and direction of insertion. In such an instance, it is a matter of course to test transformants for expression, 1 in 6 of which should have the correct reading frame. Suitable vectors may be selected as a matter of course by those skilled in the art according to the expression system desired.

By transforming a suitable organism or, preferably, eukaryotic cell line, such as HeLa, with the plasmid obtained, selecting the transformant with ampicillin or by other suitable means if required, and adding tryptophan or other suitable promoter-inducer (such as indoleacrylic acid) if necessary, the desired stromelysin-3 may be expressed. The extent of expression may be analyzed by SDS poly-, acrylamide gel electrophoresis—SDS-PAGE (Lemelli, *Nature* 227:680–685 (1970)).

Suitable methods for growing and transforming cultures etc. are usefully illustrated in, for example, Maniatis (*Molecular Cloning, A Laboratory Notebook,* Maniatis et al. (eds.), Cold Spring Harbor Labs, N.Y. (1989)).

Cultures useful for production of stromelysin-3, or a peptide thereof, may suitably be cultures of any living cells, and may vary from prokaryotic expression systems up to eukaryotic expression systems. One preferred prokaryotic system is that of *E. coli,* owing to its ease of manipulation. However, it is also possible to use a higher system, such as a mammalian cell line, for expression of a eukaryotic protein. Currently preferred cell lines for transient expression are the HeLa and Cos cell lines. Other expression systems include the Chinese Hamster Ovary (CHO) cell line.

One valuable system is the baculovirus system, wherein butterfly cells are cotransfected with a DNA vector encoding stromelysin-3, or a suitable peptide, and baculovirus DNA. Recombination occurs within the cell, and suitable baculovirus recombinants may be selected by standard techniques. Thereafter, the recombinant may be used to infect the cell line as desired, stromelysin-3 or peptide being expressed on infection. A particular advantage of this system is the amount of protein produced, which can be in the range of about 1 to about 500 mg/litre.

Although such systems tend not to be as easy to use as the *E. coli* system, the advantage lies in the processing of the protein after primary synthesis. *E. coil,* for example, does not employ the same system for processing pre-proproteins as mammalian cells.

Other expression systems which may be employed include streptomycetes, for example, and yeasts, such as Saccharomyces spp., especially *S. cerevisiae.* Any system may be used as desired, generally depending on what is required by the operator. Suitable systems may also be used to amplify the genetic material, but it is generally convenient to use *E. coli* for this purpose where only proliferation of the DNA is required.

It may be advantageous to produce only the mature enzyme, for the purposes of raising antibodies, as the sequence of the mature enzyme is common to the pro- and prepro sequences also. However, it will be appreciated that cleavage of the pro and prepro portions may alter the tertiary configuration of the molecule, and so it is possible that an antibody raised against the mature enzyme will not detect the proenzyme, for example. Antibodies raised to the enzyme in either of its earlier states and/or to the pre- or pro-peptides which are cleaved may also prove useful.

The peptide or nucleotide sequence may be any that is characteristic of stromelysin-3, having consideration to the purpose to which it is to be put. Ideally, the sequences would be completely characteristic of stromelysin-3, but the length of such sequences may vary according to the region of the stromelysin-3 molecule. The most preferred regions are those which are highly conserved, and which are not shared with other proteins, although it may be advantageous if the sequence is characteristic of the MMPs or, more particularly, those MMPs associated with invasive tumors.

The invention includes and relates to equivalents of the above peptide and nucleotide sequences, the term "equivalent" being used in the sense of the preceding description, that is to say, equivalents in the sense of sequences having substitutions at the C- or N-terminals, or anywhere else.

The invention also includes routants of the sequences, the term "mutants" being used with reference to deletions, additions, insertions, inversions and replacement of amino acid residues or bases in the sequence subject to the restrictions described above.

The present invention further includes variants of the sequences, which term is used in relation to other naturally occurring stromelysin-3 which may be discovered from time to time and which shares essentially the same sequence as shown in FIG. 2A and FIG. 2B, but which vary therefrom in a manner to be expected within a large population. Within this definition lie allelic variation and those peptides from other species showing a similar type of activity and having a related sequence. Also included, although less preferred, are animal sequences.

We have also discovered that stromelysin-3 expression can be stimulated by, for example, growth factors and tumor promoters. Typical examples of such factors include EGF FGF and PDGF and TPA. Thus, in conjunction with the foregoing processes, detection of any of these factors in a tumor sample may also help to diagnose the metasiatic condition of a cancer.

Thus, the invention also provides the treatment of a metastatic cancer by altering the expression of the stromelysin-3 gene. This may be effected by interfering with the factor required to stimulate stromelysin-3 production, such as by directing specific antibodies against the factor, which antibodies may be further modified to achieve the desired result. It may also be possible to block the receptor for the factor, something which may be more easily achieved by localization of the necessary binding agent, which may be an antibody or synthetic peptide, for example.

Affecting stromelysin-3 gene expression may also be achieved more directly, such as by blocking of a site, such as the promoter, on the genomic DNA.

Where the present invention provides for the administration of, for example, antibodies to a patient, then this may be by any suitable route. If the tumor is still thought to be, or diagnosed as, localized, then an appropriate method of administration may be by injection direct to the site. If the target is breast cancer, then an injection to the breast may suffice, or an implant may be used. If TIMPs are to be administered, for example, then it may also be possible to employ a dermal patch for prolonged administration.

If the cancer is pharyngeal, then a further option may be oral administration, for example, by means of gargling.

In either instance, administration may instead, or additionally, be by injection, including subcutaneous, intramuscular, intravenous and intradermal injections.

Formulations may be any that are appropriate to the route of administration, and will be apparent to those skilled in the art. The formulations may contain a suitable carrier, such as saline, and may also comprise bulking agents, other medicinal preparations, adjuvants and any other suitable pharmaceutical ingredients.

Suitable preparations may also include vaccines comprising stromelysin-3 or a characteristic peptide thereof. Such vaccines may be active or passive, but passive is generally preferred as stromelysin-3 expression occurs in the uterus, and indefinite exposure to anti-stromelysin-3 antibodies may have undesirable effects. However, active vaccination may be advantageous, especially where a patient has had a hysterectomy, as no tissues will then normally express stromelysin-3. Other suitable vaccines include recombinant viruses containing a nucleotide sequence encoding a stromelysin-3 or a characteristic peptide thereof. One suitable such virus is the vaccinia virus.

The following Examples serve to illustrate the present invention, and are not intended to limit the invention in any manner.

EXAMPLE 1

Cloning of a breast cancer specific cDNA

A breast cancer cDNA library was constructed in the λgt10 vector using poly($A^+$) RNA from a surgical resection-sample (referred to as tumor C1) of a primary breast cancer. 50,000 plaques were differentially screened using (+) and (−) probes corresponding to cDNAs reverse-transcribed from C1-poly($A^+$) RNA and poly($A^+$) RNA from a breast fibroadenoma (referred to as F1), respectively.

FIG. 1A–FIG. 1D show a Northern blot analysis of total RNA from C1-breast carcinoma and F1-fibroadenoma using cDNA probes of four genes (A–D) exhibiting higher levels of expression in the carcinoma than in the fibroadenoma. Each lane contained 8 µg of total RNA. The filters were reprobed using the 36B4 probe which corresponds to an ubiquitously expressed gene (Rio et al., *Proc. Nat. Acad. Sci. USA* 84:9243–9247 (1987)).

Specifically, total RNA was prepared (Chirgwin et al., *Biochemistry* 18:5294–5299 (1979)) from surgical specimens stored in liquid nitrogen, and poly($A^+$) RNA was selected by oligo(dT)-cellulose chromatography. A breast cancer-enriched cDNA library was constructed using cDNA prepared from an oestrogen receptor-negative, grade II, ductal carcinoma (referred to as C1), in which stromal cells represented approximately 50% of the total cell population.

Prior to cloning, the single-stranded cDNA was substracted with an excess of poly($A^+$) RNA from a breast fibroadenoma (referred to as F1), and the single-stranded enriched material was purified by hydroxyapatite chromatography (Davis et al., *Proc. Nat. Acad. Sci. USA* 81:2194–2198 (1984); Rhyner et al., *Neuroscience Res.* 16:167–181 (1986)).

The breast cancer-enriched cDNA was made double-stranded and cloned into the EcoRI site of the λgt10 vector. Three million recombinant phages were obtained, and ≈50,000 were differentially screened using replica nylon filters (Biodyne A, Pall Corporation) from plates containing ≈5,000 cDNA clones.

(+) and (−) probes were made using C1-breast cancer cDNA and F1-breast fibroadenoma cDNA, respectively. Both probes were substracted (Davis et al., *Proc. Nat. Acad. Sci. USA* 81:2194–2198 (1984); Rhyner et al., *Neuroscience Res.* 16:167–181 (1986)) with an excess of total human liver RNA before [$^{32}$P]-labeling using random priming synthesis.

Hybridizations were for two days under stringent conditions (50% formamide, 42° C.) and washing was in 2×SSC, 0.1% SDS, at 22° C., followed by 0.1×SSC, 0.1% SDS at 55° C. 130 differentially labelled plaques were selected for a second screening.

The cDNA inserts of five differential plaques taken at random were purified by PCR amplification, [$^{32}$P]-labelled, and hybridized to all of the differential plaques to identify related clones. This procedure was repeated several times with differential plaques taken at random, finally yielding four genes referred to as A to D, which exhibited higher levels of expression in C1-carcinoma than in F1-fibroadenoma. The Northern blots for C1-breast cancer and F1-breast fibroadenoma were prepared using total RNA (8 µg) separated by electrophoresis in 1% agarose gels containing formaldehyde and transferred to Hybond-N filters (Amersham).

The blots were stained with methylene blue before prehybridization to check for the integrity and amounts of transferred RNA. Hybridization (18 h) and washing were performed under standard conditions, as described above, using [$^{32}$P]-labeled cDNA inserts corresponding to A–D genes.

The genes A and B, which were also expressed in normal colon (not shown), were not examined further.

Although expressed in colon (not shown), the C gene was partially characterized because of its high level of differential expression (FIG. 1A–FIG. 1D). It was also expressed in a variety of transformed epithelial cell lines and in normal human skin (not shown). Sequencing of the cDNA of one C clone indicated that the corresponding gene belongs to the keratin gene superfamily (data not shown).

Finally, the D gene (also referred to herein as the stromelysin-3 gene) was further studied, because of its marked differential expression between C1-carcinoma and F1-fibroadenoma (FIG. 1A–FIG. 1D), and also because it was not expressed in normal human colon and in a number of other human tissues (infra).

EXAMPLE 2

Sequencing of Stromelysin-3 Gene and Encoded Protein

Several independent clones were isolated from a non-substracted C1-breast cancer λgt10 cDNA library using a D cDNA insert as probe, and sequenced. FIG. 2A and FIG. 2B shows the nucleotide sequence of the full length D cDNA and the corresponding protein sequence.

The cDNA open reading frame, encoding a 488 amino acid-long protein, is followed by a 714 base 3'-untranslated region containing a poly(A) addition signal located 14 bases upstream from the 3'-end of the RNA. A presumptive initiation methionine is located at nucleotide position 10–12. Although the corresponding AUG is not associated with and located in a sequence which conforms to the Kozak consensus motif, translation is probably initiated at this AUG, since the sequence immediately downstream corresponds to that for a hydrophobic leader peptide, an expected feature (infra).

In FIG. 2A and FIG. 2B, which shows the nucleotide sequence of stromelysin-3 cDNA and deduced amino acid sequence, the nucleotide residues are numbered in the 5' to 3' direction and deduced amino acids in the open reading frame are designated by their one-letter codes. Starting from the 5'-end, the underlined nucleotide sequences correspond to: the putative signal peptide (two potential cleavage sites are marked by arrows); the PRCGVPD sequence characteristic of prometalloproteinases; the conserved histidine residues of the zinc-binding domain (Matrisian, L. M., *Trends Genet.* 6:21–125 (1990)); and the poly(A) addition signal sequence.

Specifically, a cDNA insert corresponding to the 3'-part of D cDNA [250 bp including a 19 bp poly(AT) region] was [$^{32}$P]-labeled by random priming synthesis and used to screen a non-substracted λgt10 cDNA library generated from C1-breast tumor poly(A⁺) RNA by the method of Gubler and Hoffmann (*Gene* 25:262–269 (1983)). Several independent clones were identified and subcloned in M13 sequencing vector. DNA sequence was determined by the dideoxy method using sequenase and the deaza-dGTP reagent kit from US Biochemical. The sequence was analyzed using the PC/GENE software package.

EXAMPLE 3

Stromelysin-3, a putative metalloproteinase

FIG. 3A–FIG. 3D shows a comparison of the predicted amino-acid sequences of human stromelysins and human type I collagenase.

FIG. 3A, FIG. 3B and FIG. 3C Amino-acid sequences were aligned using a multialignment program (Higgins et al., *Gene* 73:237–244 (1988)). Amino-acid residues identical in all of the four sequences are marked by stars. The arrows denote putative signal peptide cleavage sites of stromelysin-3. The arrowhead points to the cleavage which occurs on activation of type I procollagenase and prostromelysins. The 10 amino-acid residues specific to stromelysin-3 at the level of this cleavage site are boxed. The PRCGVPD sequence and the conserved residues of the putative zinc-binding domain are underlined.

FIG. 3D Left, regions of similarity (in percent amino-acid identity) between stromelysin-3, stromelysin-1 (ST1, Whitham et al., *Biochem. J.* 240:913–916 (1986)), stromelysin-2 (ST2, Muller et al., *Biochem. J.* 253:187–192 (1988)) and type I collagenase (COI, Whitham et al., *Biochem. J.* 240:913–916 (1986));

Right, regions of similarity between ST1, ST2 and COI; P indicates the signal peptide and the pro-domain; ENZ indicates the domain corresponding to the mature active enzymes.

Thus, comparison of the derived protein sequence with the Swissprot data library (release 14) showed that the new protein belongs to the family of secreted matrix metalloproteinases (MMPs) (FIG. 3A–FIG. 3C). Accordingly, the new protein possesses an hydrophobic N-terminal leader sequence candidate (underlined in FIG. 2A and FIG. 2B), and exhibits the highly conserved sequence PRCGVPD (amino-acid residues 78–84), which is characteristic of the prodomain of the MMPs, as well as having the zinc binding site of MMPs (amino-acid residues 212–225—FIG. 3a) (Matrisian, L. M., *Trends Genet.* 6:121–125 (1990)).

By analogy with the other members of the family, the N-terminal amino acid of the mature protein is likely to correspond to phenylalanine 98 of the pre-proprotein (Whitham et al., *Biochem. J.* 240:913–916 (1986)) (FIG. 3A–FIG. 3C). After optimal alignments, the similarity between the putative mature protein is 40% with stromelysin-1 (Whitham et al., *Biochem. J.* 240:913–916 (1986)), 38% with stromelysin-2 (Muller et al., *Biochem. J.* 253:187–192 (1988)) and 36% with type I collagenase (Goldberg et al., *J. Biol. Chem.* 261:6600–6605 (1986)) (FIG. 3D).

The substrate specificity of the new protein is not known. Herein, it is referred to as stromelysin-3, although its similarity with stromelysin-1 (40%) is clearly much below that existing between stromelysin-1 and stromelysin-2 (79%), and even lower than the similarity existing between type I collagenase and stromelysin-1 (53%) (FIG. 3D). Thus, while the protein is an MMP, the cognomen "stromelysin" is not necessarily strictly accurate, but is convenient.

In addition, upstream of the PRCGVPD sequence, there is no significant similarity between stromelysin-3 and the other MMPs with which it is has been compared (FIG. 3A–FIG. 3D). However, stromelysin-3 has a unique short sequence (amino-acid residues 88–97) at a position corresponding substantially precisely with the proprotein cleavage site of type I collagenase and the stromelysins (Whitham et al., supra). Further, stromelysin-3, as with type I collagenase and the other stromelysins, does not exhibit the fibronectin-like domain characteristic of type IV collagenases (Wilhelm et al., *J. Biol. Chem.* 264:17213–17221 (1989)).

EXAMPLE 4

Over-expression in Breast Carcinomas

The occurrence of stromelysin-3 RNA transcripts was studied in resected samples of 30 breast carcinomas and five breast fibroadenomas.

FIG. 4A–FIG. 4F shows Northern blot analyses of human metalloproteinase RNAs in breast tumors:

FIG. 4A stromelysin-3 RNA;
FIG. 4B type I collagenase RNA (COI);
FIG. 4C 92-kD type IV collagenase RNA (COIV 92K);
FIG. 4D 72-kD type IV collagenase RNA (COIV 72K);
FIG. 4E stromelysin-1 and -2 RNA's (ST1/2); and
FIG. 4F pump-1 RNA (PUI).

Total RNA was prepared from four oestrogen receptor-negative breast carcinomas (C1, grade II; C2, C3 and C4, grade III), six oestrogen receptor-positive breast carcinomas (C5, C8 and C9, grade II; C6 and C7 grade III; C10, grade I) and four breast fibroadenomas (F2–F5). Each lane contained 8 µg of RNA. The 36B4 signal corresponds to the RNA of a control gene (FIG. 1A–FIG. 1D).

Specifically, several Northern blots were prepared in parallel with identical RNA samples, as for FIG. 1A–FIG. 1D, and hybridized with either of the following cDNA probes: (a) 1.6 kb insert covering the 3'-part of stromelysin-3 cDNA, (b) COI cDNA, (e) ST2 cDNA (which cross-hybridizes with ST1 RNA), (f) PU1 cDNA (COI, ST2 and PU1 probes kindly provided by R. Breathnach, Muller et al., *Biochem. J.* 253:187–192 (1988)), or 80 mer antisense oligonucleotide probes corresponding to (c) COIV 92K (nucleotides 2144–2223, Wilhelm et al., *J. Biol. Chem.* 2641:7213–17221 (1989)) and (d) COIV 72K (nucleotides 1937–2016, Collier et al., *J. Biol. Chem.* 263:6579–6587 (1988)).

The cDNA probes were ($^{32}$P)-labeled using random priming synthesis ($\approx 5 \times 10^8$ cpm/µg) and the oligonucleotides were labeled using 5'-end kination $\approx 10_8$ cpm/µg). Hybridizations were carried out under stringent conditions (42° C., 50% formamide) with $\approx 10^6$ cpm/ml. The filters were then washed in 2×SSC, 0.1% SDS, at 22° C., followed by 0.1×SSC, 0.1% SDS at 55° C. Autoradiography was for FIG. 4A, 18h, FIG. 4B, 20h, FIG. 4C, FIG. 4D and FIG. 4E, 4 days, FIG. 4F, 2 days, at −80° C. with an intensifying screen.

Stromelysin-3 mRNA was found in all of the breast carcinomas, regardless of whether they were oestradiol receptor (ER) positive (C5–C10) or negative (C1–C4) (FIG. 4A), but not in the fibroadenoma samples, with one exception (F2) where the level of expression was similar to the lowest level observed in breast carcinomas.

The occurrence of RNA transcripts of the other members of the MMP gene family was also investigated in the same samples (FIG. 4B–FIG. 4F). These other members of the MMP family can clearly be separated into two classes, according to their pattern of expression in human breast tumors. The first class includes the 72 kD type IV collagenase (COIV 72K, FIG. 4D), stromelysin-1 and -2 (ST1/2, FIG. 4E) and pump-1 (PU1, FIG. 4F), all of which genes were expressed in both malignant and benign tumors. By contrast, the second class, which includes stromelysin-3 (FIG. 4A), type I collagenase (COI, FIG. 4B) and the 92 kD type IV collagenase (COIV 92K, FIG. 4) genes, shows over-expression only in breast carcinomas, although only stromelysin-3 was consistently associated therewith.

The patterns of expression were not identical for the three genes of the second class. Type I collagenase RNA transcripts were not detected in the C5, C6, C7 and CIO carcinomas, and the 92 kD type IV collagenase RNA transcripts were not seen in the C7 and CIO samples, but the stromelysin-3 RNA transcripts were clearly detected in all tumors.

Thus, stromelysin-3 appears to be diagnostic of invasive breast carcinomas, while type I collagenase and the 92 kD type IV collagenase may also be specifically involved in breast cancer progression in some cases.

EXAMPLE 5

Expression of ST3 in Cells from Various Sources

FIG. 5A–FIG. 5D show Northern blot analyses of stromelysin-3 RNA in various cell lines and tissues.

FIG. 5A Three normal and five metastatic auxiliary lymph nodes from patients with breast cancers;

FIG. 5B four oestrogen receptor-negative (BT-20, MDA-231, SK-BR-3, HBL-100) and four oestrogen receptor-positive (T-47D, BT-474, ZR-75-1, MCF-7) breast cancer cell lines;

FIG. 5C 10 normal human tissues,

FIG. 5D HFL-1 human foetal diploid fibroblasts (ATCC CCL 153) cultured in serum-free medium (1 and 2), in the absence (1) or presence (2) of TPA (10 ng/ml) or cultured in serum-free medium supplemented with 20 µg/ml insulin (3 to 6), in the absence (3) or presence (4) of PDGF (20 ng/ml, British Biotechnology), (5) of EGF (20 ng/ml, Collaborative Research) or (6) of bFGF (10 ng/ml, kindly provided by Pettmann (*FEBS Lett.* 189:102–108 (1985))).

In FIG. 5A, each lane contained 10 µg of total RNA with the exception of lane 5 (2 µg) and lane 6 (20 µg). In FIG. 5B and FIG. 5C, each lane contained 8 µg of total RNA, and in FIG. 5D, each line contained 5 µg of cytoplasmic RNA.

Specifically, in FIG. 5A, FIG. 5B and FIG. 5C the blots were made and processed as indicated in FIG. 4A–FIG. 4F for stromelysin-3. In FIG. 5D, confluent HFL-1 fibroblasts were kept in serum-free DMEM culture medium. After 24 hrs, fresh medium was added and supplemented or not with TPA or growth factors, as indicated above. After 24 hrs of culture, the cells were harvested and cytoplasmic RNA prepared (Gough, N. M., *Analyt. Biochem.* 173:93–95 (1988).

The blots were then prepared and processed as indicated in FIG. 4A–FIG. 4F for stromelysin-3, but the autoradiography was for three days.

92 kD collagenase IV RNA transcripts were found in 3 normal and 5 breast cancer metastatic lymph nodes, whereas stromelysin-3 RNA transcripts were detected only in the metastatic nodes (FIG. 5A, and data not shown).

In contrast to the results obtained with primary malignant breast tumors and metastatic lymph nodes, no stromelysin-3 RNA transcripts could be detected under similar conditions in eight human breast cancer cell lines, irrespective of their ER status (FIG. 5B). Similarly, stromelysin-3 RNA transcripts could not be detected in a number of normal human adult tissues (FIG. 5C), with two notable exceptions, uterus and placenta.

Stromelysin-3 is not apparently associated with all cancers, and only low levels of stromelysin-3 RNA transcripts were found in RNA samples from colon, ovary, kidney and lung cancers. However, high levels of expression, comparable to those found in breast cancers, were observed in larynx cancer RNA samples (data not shown).

EXAMPLE 6

Specific Expression in Stromal Cells of Invasive Tumors

The expression of the stromelysin-3 gene in primitive breast carcinomas, but not in a number of established breast cancer cell lines, suggested that the gene was expressed in the stromal cells surrounding the tumor, rather than in the neoplastic cells themselves.

In situ hybridization experiments using a [$^{35}$S]-labelled stromelysin-3 antisense riboprobe were performed using sections from six carcinomas (tumors C1, C3, C5, C9, C10, referred to as for FIG. 4A–FIG. 4F, and tumor C11, an ER-positive carcinoma not shown in FIG. 4A–FIG. 4F).

Specifically, in situ hybridization was carried out as described by Cox et al. (*Dev. Biol.* 101:485–502 (1984)). Deparaffinised and acid-treated sections (6 µm thick) were proteinase K-treated and hybridized overnight with [$^{35}$S]-labelled antisense transcripts from a stromelysin-3 cDNA insert (467 bp extending from nucleotides 1128 to 1594) subcloned in Bluescript II (Stratagene). Hybridization was followed by RNase treatment (20 µg/ml, 30 min, 37° C.) and stringent washing (2×SSC, 50% formamide, 60° C., 2h), prior to autoradiography using NTB2 emulsion (Kodak). Autoradiography was for 15 days. No significant labeling above background was observed under similar conditions using a sense riboprobe (not shown).

FIG. 6A–FIG. 6L shows the presence of stromelysin-3 RNA transcripts in sections of breast carcinomas and embryo limb bud. FIG. 6A, FIG. 6C, FIG. 6E, FIG. 6G, FIG. 6I and FIG. 6K: bright fields of tissue sections (×100) stained with haematoxylin; FIG. 6B, FIG. 6D, FIG. 6F, FIG. 6H, FIG. 6J and FIG. 6L: the same sections (still stained with haematoxylin) after in situ hybridization with an antisense stromelysin-3 cRNA probe and dark field imaging.

FIG. 6A and FIG. 6B, grade II ductal breast carcinoma (tumor C1, see FIG. 4A–FIG. 4F): infiltrating cancer cells (C) are surrounded by a stroma rich in fusiform cells (S); stromelysin-3 RNA transcripts are most abundant in the stromal cells immediately surrounding the neoplastic epithelial cells. FIG. 6C and FIG. 6D, grade III ductal breast carcinoma (tumor C3, see FIG. 4A–FIG. 4F): multiple islands of infiltrating breast cancer cells (C) are surrounded by stromal cells; the expression of the stromelysin-3 gene is weaker in the central part of most of the stromal trabeculae (S) i.e. in the region which is the farthest away from the neoplastic cells. FIG. 6E and FIG. 6F: ductal carcinoma, (tumor C3, see FIG. 4A–FIG. 4F) together with two normal lobules (N); stromelysin-3 RNA transcripts were detected exclusively in the stroma apposing the infiltrating cancer cells (C), with the exception of a small area rich in lymphocytes (arrow). FIG. 6G and FIG. 6H, ductal carcinoma (tumor C10, see FIG. 4A–FIG. 4F): stromelysin-3 RNA transcripts can be detected above background in the stromal cells surrounding the infiltrating (upper corner, right) but not the in situ (star) breast cancer cells. FIG. 6I and FIG. 6J, ductal carcinoma (tumor C11, ER-positive, grade II, carcinoma); left: carcinoma in situ (stars), no stromelysin-3 RNA transcripts can be detected in the stromal cells; right: infiltrating neoplastic cells surrounded by stromal cells expressing the stromelysin-3 gene. FIG. 6K and FIG. 6L, interdigital region of an 8-week-old human embryo limb bud: stromelysin-3 RNA transcripts are detected in the mesoderm underlying the primitive epiderm, most notably in the interdigital area (M); note that the primitive epiderm (arrows), the cartilage in formation (PC), and the surrounding mesoderm are not labelled.

In all cases, stromelysin-3 RNA transcripts were detected only in the stromal cells surrounding the islands of malignant epithelial cells which formed the invasive component of the tumors (FIG. 6A and FIG. 6B, for tumor C1; FIG. 6C, FIG. 6D, FIG. 6E and FIG. 6F for tumor C3; FIG. 6G and FIG. 6H for tumor C10; FIG. 6I and FIG. 6J, right hand side, for tumor C11; and data not shown for tumors C5 and C9).

In metastatic lymph nodes (same source as C5) the expression of the stromelysin-3 gene was also restricted to the stromal cells surrounding the metasiatic epithelial cells (data not shown).

It is particularly notable that, in all cases, the malignant epithelial cells themselves were not labelled, and that the highest levels of expression were observed in the stromal cells in apposition to the malignant cells. In marked contrast, no significant expression could be detected in the stromal cells surrounding in situ carcinoma lesions still surrounded by a basement membrane (FIG. 6G and FIG. 6H for tumor C10; FIG. 6I and FIG. 6J, left hand side, for tumor G11), while the labelling of stromal cells could be clearly observed in the invasive component of the same tumors (FIG. 6G and FIG. 6H for tumor C10; FIG. 6I and FIG. 6J, right hand side, for tumor C11).

Also, no significant expression could be detected in stromal cells located at a distance from the cancerous cells nor in the stromal cells surrounding normal ducts and ductules (e.g. FIG. 6E and FIG. 6F). No discrete foci of stromelysin-3 transcripts were detected in sections of the F2 fibroadenoma weakly positive for stromelysin-3 RNA on Northern blots (FIG. 4A and not shown).

Both fibroblasts and myofibroblasts are known to be present in the stroma of invasive breast carcinomas (Ahmed, A., *Pathol. Annu.* 25(Pt2):237–286 (1990)). Using our in situ hybridization technique, it was not possible to determine whether only one or both of these cell types expressed stromelysin-3 gene.

EXAMPLE 7

Stimulation of ST3 Expression by Growth Factors

The above results indicate that expression of the stromelysin-3 gene in stromal cells is likely to be induced by a diffusible factor secreted by the neoplastic cells. Growth factors such as EGF, FGF and PDGF, as well as some cytokines (IL-1α, β, and TNF-α), and tumor promoters (e.g. TPA) are known to activate the transcription of MMP genes (Kerr et al., *Science* 242:1424–1427 (1988)). It has been also reported that tumor cells from several sources produce a factor(s) which stimulates collagenase I production by human fibroblasts (Lippman et al., *Recent Prog. Hormone Res.* 45:383–440 (1990)). PDGF, FGF and TGF-α activities are known to be secreted by breast cancer cells in vitro (Salomon et al., in *Breast cancer: cellular and molecular biology* (eds., Lippman, M. E. and Dickson, R. B.), pp. 363–389 (Kluwer, Boston, (1988)).

To investigate whether stromelysin-3 gene expression could be modulated by exogenous stimuli, human foetal diploid fibroblasts were grown in the absence or presence of either PDGF, bFGF and EGF, and also of the tumor promoter TPA. Addition of either of these growth factors or of TPA resulted in an increase of stromelysin-3 RNA transcripts in the fibroblasts, the strongest stimulation being observed with bFGF (FIG. 5D).

EXAMPLE 8

Stromelysin-3 Expression in the Embryo

As the stromelysin-3 gene was expressed in response to stimulation by growth factors in foetal fibroblasts, we investigated whether the gene might be normally expressed during embryo development.

Stromelysin-3 transcripts were detected in several discrete regions of an 8-week-old human embryo, notably in the interdigital region of the limb buds (FIG. 6K and FIG. 6L, and data not shown), an area known to be associated with programmed cell death at this stage of embryogenesis (Milaire, J., *Organogenesis* (eds., De Haan, R. L. and Ursprung, H.), pp. 283–300 (Holt, Rinehart and Winston, New York, 1965)).

The labelling was observed in the embryonic mesoderm underlying the primitive epiderm which remained unlabelled. Notably, the mesenchymal cells located at a distance from the epiblast were also mRNA-negative.

Thus, the finding that the stromelysin-3 gene is expressed during normal embryonic development in an area where tissue remodelling is well documented suggests that expression of stromelysin-3 in breast tumors plays a role in the ECM remodelling processes associated with cancer progression.

EXAMPLE 9

Cloning of mouse cDNA encoding ST3

A probe containing human cDNA encoding ST3 was used to screen a mouse placental cDNA library using standard procedures (Sambrook et al., *Molecular Cloning: A Laboratory Manual*, Cold Spring Harbor Press (1989)). The screening resulted in obtaining a full length mouse cDNA encoding ST3 (FIG. 7A and FIG. 7B).

An analysis of the two sequences revealed a 89% homology in the amino acid sequence of the mature form of ST3 and approximately a 55% homology at the pre and pro-domains (FIG. 7A and FIG. 7B).

The pattern of expression in various mouse cells was determined using the methods described in Examples 4–8.

The pattern of ST3 expression in mouse was found to be identical with respect to tissue specificity as that found with human tissue. The highest level of expression was found in placental and uteran tissue.

EXAMPLE 10

Expression of ST3 is associated with increased invasiveness in head and neck squamous cell carcinomas Source of tissue samples Fresh tissue samples were obtained from 111 patients undergoing surgery for head and neck tumors, as previously described (Muller, D., et al., *Int. J. Cancer* 48:550–556 (1991)). In brief, in each case, the portion of the tumor used for Northern blot analysis was resected near the advancing edge of the tumor, avoiding its necrotic center. The tumor samples were immediately frozen and stored in liquid nitrogen until RNA extraction. The remaining resected tumor was fixed in formaldehyde and embedded in parrafin for further histologic evaluation and in situ hybridization experiments. Out of the 111 tumors analyzed, 107 were primary squamous cell carcinomas and 4 corresponded to recurrent disease. Fifteen originated from the oral cavity, 29 from the oropharynx, 49 from the hypopharynx and 14 from the larynx. None of the patients had previously received irradiation or chemotherapy. In 21 cases, tissue samples of disrupted lymph nodes, corresponding to metastatic masses, were also available for analysis. Normal mucosa of the upper aerodigestive tract, resected 5 cm distant from the tumor area, was obtained in 60 cases.

Northern blot analysis and evaluation of stromelysin-3 RNA levels

Twenty µg of total RNA from each tissue sample, prepared with the LiCl/urea method (Auffrey and Rougeon, *Eur. J. Biochem.* 107:303–314 (1980)), were analyzed by agarose gel electrophoresis, and Northern blots obtained as previously described (Muller, D., et al., *Int. J. Cancer* 48: 550–556 (1991)). After prehybridization, the blots were hybridized with a ST3 cDNA probe (nucleotides 346 to 2,105, Basset, P., et al., *Nature (Lond.)* 348:699–704 (1990)), $^{32}$P-labeled by random priming synthesis (Boehringer Mannheim), followed by washings with standard conditions and autoradiography at −70° C. For each blot, 3 successive exposures have been carried out for 6, 24 and 72 hours, respectively. The blots were systematically rehybridized with a 36B4 cDNA probe corresponding to an ubiquitous RNA (Masiakowski, P., et al., *Nucleic Acids Res.* 10:7895 (1982)).

The levels of ST3 transcripts were quantified by densitometric analysis of autoradiographs of the Northern blots. To correct for film non-linearity, the amount of radioactivity bound in each lane was estimated from the optical density of the autoradiographic band by reference to a calibration curve obtained from the densitometric data of a serial dilution of a $^{32}$-P-labeled standard sample. All results were corrected for RNA loading by densitometric data obtained for the 36B4 signals. Two of the samples analyzed in the study were included in each blot (one of them was assigned a value of 1 arbitrary unit, and consequently the second corresponded to 8 units) in order to standardize the reading from one blot to another. ST3 RNA levels were classified as not detectable (0) or detectable (I to IV), using in the later case 4 RNA classes defined on the basis of the quartiles of the statistical distribution. Thus, class I corresponded to RNA levels ranging from more than 0 to 2.5 units, class II from more than 2.5 to 6 units, class III from more than 6 to 15 units, and class IV to levels higher than 15 units.

Histopathologic features of the tumors

The histologic evaluation of tumors was performed on 7 to 15 tissue sections of each specimen obtained as described above. The local invasiveness of tumors was evaluated according to histologic characteristics (Muller, D., et al., *Int. J. Cancer* 48:550–556 (1991)), with a grading scheme derived from that of Jakobsson et al. (Jakobsson, P. A., et al., *Acta Radiol.* 12:1–18 (1976)). Briefly, local invasiveness was scored as weak (1+), moderate (2+) or high (3+), according to the extent of cancerous infiltration to contiguous extranodal anatomic structures, and to the type of cancerous invasion. Neoplasms with limited extent of cancerous infiltration, and demonstrating cohesive pushing invasive borders and/or few thick invasive cords of cancer cells, were scored (1+). Those with large extension to contiguous structures, and invading as non cohesive small irregular cords, were scored (2+). Those demonstrating vascular and/or perineural spread and/or cartilage destruction, and invading as irregular cords of cancer cells and/or small aggregates and/or isolated cancer cells, were scored (3+).

in situ hybridization in situ hybridization was performed on formaldehyde-fixed paraffin-embedded tissue sections as previously described (Basset, P., et al., *Nature (Lond.)* 348:699–704 (1990)). In brief, 8 µm-thick rehydrated and acid-treated sections were digested with proteinase K (2 µg/ml, 30 min, 37° C.). Following overnight hybridization (0.3M NaCl, 50% formamide, 50° C.) with $^{35}$S-labeled antisense RNA probes, the sections were RNAse-treated (20 µg/ml, 30 min, 37° C.) and stringently washed (2×SSC, 50% formamide, 60° C., 2×2h). Autoradiography was for 3 to 4 weeks using NTB2 emulsion (Kodak). After exposure, slides were developed and hematoxylin-eosin stained. $^{35}$S-labeled antisense RNA (specific activity: $10^9$ cpm/µg) were obtained by in vitro transcription from the appropriate cDNA fragments subcloned into pBluescript II vector (Stratagene): a 467 bp ST3 cDNA fragment extending from nucleotides 1,127 to 1,594 (Basset, P., et al., *Nature (Lond.)* 348:699–704 (1990)); a 1.5 kb interstitial type I collagenase cDNA fragment extending from nucleotide 261 to 1,735 (Muller, D., et al., *Biochem. J.* 253:187–192 (1988)); the templates for ST1, ST2 and pump-1 were full length cDNAs (Muller, D., et al., *Biochem. J.* 253:187–192 (1988)). Although ST1 and ST2 full length cDNA probes cannot be used to discriminate between ST1 and ST2 gene expression by Northern blot analysis (due to the sequence similarities between the two cDNAs, Muller, D., et al., *Biochem. J.* 253:187–192 (1988)), these probes are specific when used in in situ hybridization experiments, because RNA duplex which are not 100% homologous are degraded during RNase treatment after in situ hybridization.

Immunohistochemical analysis and antibody preparation.

Immunohistochemical analysis was performed on paraffin-embedded tissue sections. ST3 was immunodetected with a rabbit polyclonal antiserum (Ab 349) obtained by immunization with a synthetic peptide corresponding to the 25 C-terminal amino-acid residues of human ST3, which do not exhibit significant similarity with the corresponding amino-acid residues present in the other stromelysins or in interstitial type I collagenase (Basset, P., et al., *Nature (Lond.)* 348:699–704 (1990)). The peptide was synthesized in solid phase using Fmoc chemistry (model 431A peptide synthesizer, Applied Biosystem), verified by amino-acid analysis, and coupled to ovalbumine through the cysteine residue present in the peptide (Basset, P., et al., *Nature (Lond.)* 348:699–704 (1990)). Rabbits were injected sc 3 times at 4-week intervals with 200 µg of coupled peptide mixed with complete Freund adjuvant for the first injection, and booster injections with 20 µg of uncoupled peptide were administered at 4-week intervals. Serum was collected 12 days after the last injection and used at a 1/1000 dilution. Immunostaining was performed as previously described (Rio, M. C., et al., *Proc. Natl. Acad. Sci. USA* 84:9243–9247 (1987)), using the StrAviGen detection system with streptavidin conjugated to horseradish peroxidase (BioGenex).

Statistical methods

The Kruskal-Wallis test (Hollander and Wolfe, *Non Parametric Statistical Methods,* John Wiley & Sons, New York (1973)) was used to evaluate whether ST3 RNA levels in head and neck carcinoma were correlated to the degree of local invasiveness of tumors. The statistical analysis was performed using the STATXACT statistical software package for exact nonparametric inference (Statxact statistical software package for exact nonparametric inference, CYTEL Software Corporation, Cambridge, Mass. (1989)).

Stromelysin-3 RNA levels in head and neck tissues

ST3 gene expression was evaluated by Northern blot analysis in 107 primary head and neck squamous cell carcinomas, in 4 tissue samples of recurrent disease, in 21 metasiatic lymph nodes, and in 60 normal tissue samples. A 2.4 kb ST3 transcript (FIG. 8) was detected in 95% of primary carcinomas, in the 4 recurrent diseases and in 90% of metastatic lymph nodes (Table 1). ST3 RNA levels, determined by densitometric analysis of Northern blots, ranged from 0.7 to 50 units, with a median value of 5.7 units (data not shown). However, only two normal tissue samples (3%) exhibited low ST3 RNA levels (Table 1). ST3 gene expression was similar in the 4 sites of tumor localization (oral cavity, oropharynx, hypopharynx and larynx, data not shown). No significant relation was observed between ST3 RNA levels in primary tumors and in metasiatic lymph nodes in the 21 patients for whom both types of tissue samples were available for Northern blot analysis (FIG. 8 and data not shown).

TABLE 1

STROMELYSIN-3 GENE EXPRESSION IN HEAD AND NECK TISSUES

| Tissue Sample | Number of cases | Stromelysin-3 RNA levels[a] | | | | | % of positive cases |
|---|---|---|---|---|---|---|---|
| | | 0 | I | II | III | IV | |
| Squamous cell carcinoma | 107 | 5 | 26 | 25 | 26 | 25 | 95 |
| Recurrent disease | 4 | 0 | 2 | 1 | 1 | 0 | 100 |
| Metastatic lymph node | 21 | 2 | 4 | 7 | 3 | 5 | 90 |
| Normal tissue | 60 | 58 | 2 | 0 | 0 | 0 | 3 |

[a]The numbers in the table correspond to the number of tumors found in each class of stromelysin-3 RNA level: 0, no expression; I, >0–2.5, II, >2.5–6, III, >6–15, and IV, >15 units; units were derived from Northern blot densitometry, as described in "Material and Methods".

Expression of stromelysin-3 RNA and protein in fibroblastic cells of head and neck carcinomas.

ST3 RNA distribution was studied by in situ hybridization in 10 head and neck carcinomas. ST3 transcripts were observed in most of stromal areas surrounding islands of invasive cancer cells, and the highest levels of expression were found in the fibroblastic cells closest to the malignant cells, which themselves were not labeled (FIG. 9C and 9F). However, no significant expression of the ST3 gene could be detected in the stromal cells surrounding in situ carcinomas also observed in 3 of the tumors tested (FIG. 9B and FIG. 9E, and data not shown), nor in the fibroblasts of normal tissue adjacent to the tumors (FIG. 9A and FIG. 9D).

ST3 protein also was detected in stromal cells of head and neck carcinomas. ST3 was specifically immunodetected in the cytoplasm of elongated fibroblast-like cells surrounding islands of invasive neoplastic cells, which did not themselves express the protein (FIG. 10A and FIG. 10B).

Comparison of stromelysin-3, stromelysin-1, stromelysin-2, pump-1 and type I collagenase RNA distribution in head and neck carcinomas in situ hybridization experiments were carried out on serial sections of 10 carcinomas (FIG. 11A–FIG. 11C, and data not shown), using antisense RNA probes specific to ST3 and other MMPs. In these tumors, the stromal distribution of ST3 transcripts (FIG. 11D–FIG. 11L) contrasted with that of ST2 (FIG. 11J–FIG. 11L) and of pump-1 (data not shown) transcripts which were found exclusively in epithelial cells. ST2-expressing cells were located at the periphery of neoplastic islands, in either all the cells of the peripheral layer (FIG. 11K and FIG. 11L) or in only some of them (FIG. 11J). Both types of distributions could be observed in distinct neoplastic islands of the same tumor. ST2 gene expression was not detected in normal epithelial cells (data not shown). In contrast, pump-1-expressing cells were randomly distributed in cancer cell islands and could also be detected in normal mucosa, often exhibiting glandular-type organization (dam not shown).

The expression pattern of the interstitial type I collagenase gene was distinct from that of all the other MMP genes tested. Type I collagenase RNA was most often observed in fibroblastic cells of tumoral stroma, but was also detected in neoplastic cells (FIG. 11G and FIG. 11I). The same fibroblastic cell population could to express the type I collagenase gene and the ST3 gene (compare FIG. 11D and FIG. 11G), while in other tumoral areas only the ST3 gene was expressed at significant levels (compare FIG. 11E and FIG. 11H). When observed in cancer cells, type I collagenase transcripts exhibited a distribution pattern distinct from that of ST2 transcripts. Type I collagenase gene expression was generally not restricted to the peripheral cell layer of neoplastic islands, but was observed in cells scattered throughout the neoplastic islands (FIG. 11G and FIG. 11I). However, type I collagenase RNA was not detected in either epithelial or stromal cells of normal mucosa (data not shown). Finally, we could not detect ST1 transcripts in any of the 10 carcinomas tested, even after prolonged exposure time (6 weeks).

Correlation between stromelysin-3 RNA levels and local invasiveness in head and neck carcinomas The expression of the ST3 gene in stromal cells located at the periphery of neoplastic islands suggested to us that ST3 gene expression may be specifically implicated in cancer cell invasion. Indeed, ST3 RNA levels and the degree of local invasiveness of tumors were found to be highly correlated in the 107 tumors analyzed. ST3 RNA median level significantly increases with the degree of local invasiveness (Table 2, Kruskal-Wallis test, $p<0.0001$). Furthermore, out of 51 tumors with high ST3 RNA levels (FIG. 12A, RNA classes III and IV), only two were classified as weakly invasive (1+). Reciprocally, the percentage of highly invasive tumors (scored 3+) gradually increases with the level of ST3 RNA in the tumors (FIG. 12B).

TABLE 2

Relationship between Stromelysin-3 (ST3) RNA levels and the degree of local invasiveness in head and neck carcinomas

| | | Number of Cases | ST3 RNA levels[a] | |
|---|---|---|---|---|
| | | | Median[c] | Range[d] |
| INVASIVENESS[b] | 1+ | 15 | 1.8 | 0–14 |
| | 2+ | 40 | 3.9 | 0–40 |
| | 3+ | 52 | 9.3 | 1–50 |

[a]Expressed in densitometric arbitrary units, as described in "Materials and Methods".
[b]Evaluated according to histological parameters, as described in "Materials and Methods".
[c]ST3 RNA levels and invasiveness are significantly correlated ($p < 0.0001$, Kruskal-Wallis test).
[d]Minimal and maximal values.

DISCUSSION

The present study demonstrates that the ST3 gene is expressed in most of primary head and neck squamous cell carcinomas (102 of 107) and in most of metastatic lymph nodes (19 of 21), but not in the corresponding normal mucosa. In this regard, the ST3 gene is similar to the ST2 and the type I collagenase genes which are also overexpressed in most head and neck carcinomas (Muller, D., et al., Int. J. Cancer 48:550–556 (1991)). However, the patterns of expression of the three genes are specific. ST3 gene expression is found only in fibroblastic cells, ST2 gene expression only in neoplastic cells, and type I collagenase gene expression in both cell types. These observations are similar to those of Polette et al. (Polette, M., et al., *Invasion Metastasis* 11:76–83 1991)) for type I collagenase, but they differ for ST2 since we have not detected ST2 gene expression in tumor fibroblasts. Furthermore, for both neoplastic cells expressing the ST2 gene and fibroblastic cells expressing the ST3 gene, the highest levels of expression were found in cells located in the vicinity of the boundary between invasive cancer cell islands and tumor stroma, while type I collagenase-expressing cells were more randomly distributed throughout the tumors.

These observations suggest that each of the three MMP genes known to be overexpressed in head and neck carcinomas, may have a distinct role in cancer progression. The coexpression of several members of the MMP gene family appears to be a general characteristic of human carcinomas, since it has been also observed in skin (Barsky, S. H., et al., *J. Invest. Dermatol.* 88:324–329 (1987); Pyke, C., et al., *Cancer Res.* 52:1336–1341 (1992); Wolf, C., et al., *J. Invest. Dermat.*, in press (1992)), in breast (Basset, P., et at., *Nature (Lond.)* 348:699–704 (1990); Monteagudo, C., et al., *Am. J. Pathol.* 136:585–592 (1990)), in lung (Muller, D., et al., *Int. J. Cancer* 48:550–556 (1991)), in prostate (Pajouh, M. S., et al., *J. Cancer Res. Can. Oncol.* 117:144–150 (1991)) and in colon (Levy, A. T., et al., *Cancer Res.* 51:439–444 (1991); McDonnell, S., et al., *Mol. Carcinogenesis* 4:527–533 (1991)) cancers. The simultaneous expression of several MMP genes is consistent with the concept that ECM remodeling during tumor progression requires the synergistic action of several proteinases, produced by cancer cells or by stromal cells (Gottesman, M. M., *Semin. Cancer Biol.* 1:97–98 (1990); Nakajima and Chop, *Semin. Cancer Biol.* 2:115–127 (1991); Liotta and Stetler-Stevenson, *Cancer Res.* 51:5054s–5059s (1991); Nicolson, G. L., *Semin. Cancer Biol.* 2:143–154 (1991); Liotta, L. A., et al., *Cell* 64:327–336 (1991)).

Interestingly, increased expression of MMP genes in malignant tumors appears to be tissue specific. For instance, pump-1 gene expression, which is observed both in normal and malignant tissues of breast (Basset, P., et al., *Nature (Lond.)* 348:699–704 (1990)) and of head and neck (Muller, D., et al., *Int. J. Cancer* 48:550–556 (1991) and the present study), is mainly restricted to malignant tissues in the case of prostate (Pajouh, M. S., et al., *J. Cancer Res. Clin. Oncol.* 117:144–150 (1991)), stomach (McDonnell, S., et al., *Mol. Carcinogenesis* 4:527–533 (1991)) and colon (McDonnell, S., et al., *Mol. Carcinogenesis* 4:527–533 (1991)). In contrast, the similarity between the patterns of ST3 gene expression in breast carcinomas and in head and neck carcinomas is remarkable. In both cases, the gene is expressed in fibroblast-like cells surrounding clusters of invasive cancer cells and, when several layers of stromal cells are present, the levels of ST3 gene expression are higher in the cells which are immediately surrounding the cancer cells. These observations are consistent with the concept that increased ST3 gene expression in stromal cells of carcinomas may be under the control of diffusible factor(s) directly, or indirectly, produced by the cancer cells (Basset, P., et al., *Nature (Lond.)* 348:699–704 (1990); Wolf, C., et al., *J. Invest. Dermat.*, in press (1992)). In most cell types that have been examined, the MMP genes are not constitutively expressed, but their expression is induced by treatment with a variety of agents, including growth factors and oncogene products (Matrisian, L. M., *Trends Genet.* 6:121–125 (1990)). Several growth factors can induce ST3 gene expression in cultured fibroblasts (Basset, P., et al., *Nature (Lond.)* 348:699–704 (1990)), but the tumor factor(s) responsible of ST3 induction in vivo is unknown.

The possible influence of stromal cells on the progression of epithelial malignancies has long been postulated (see Van Den Hooff, A., *Adv. Cancer Res.* 50:159–169 (1988); and Zipori, D., *Cancer J.* 3:164–169 (1990) for reviews), and it has been shown that the tumorigenicity of epithelial cancer cells in athymic mice can be increased when cancer cells are coinoculated with fibroblasts (Camps, J. L., et al., *Proc. Natl. Acad. Sci. USA* 87:75–79 (1990)). A concept now emerging is that proteinases, including ST3 in all carcinoma types so far tested (Basset, P., et al., *Nature (Lond.)* 348:699–704 (1990); Wolf, C., et al., *J. Invest. Dermat.*, in press (1992); and the present study), interstitial type I (Wolf, C., et al., *J. Invest. Dermat.*, in press (1992); Bauer, E. A., et al., *J. Invest. Dermatol.* 69:363–367 (1977)) and 72-kDa type IV (Pyke, C., et al., *Cancer Res.* 52:1336–1341 (1992)) collagenases in skin carcinomas, and urokinase in colon carcinomas (Grondahl-Hansen, J., et al., *Am. J. Pathol.* 138:111–117 (1991)), are expressed in stromal fibroblasts of human carcinomas and may be regarded as paracrine, stroma-derived factors necessary for the progression of epithelial malignancies. The present observation that ST3 gene expression in head and neck carcinoma is positively correlated with the intensity of local invasiveness further supports this hypothesis. Finally, our data indicate that increased ST3 gene expression may be a useful marker to define subpopulations of aggressive head and neck tumors.

EXAMPLE 11

MATERIALS AND METHODS
Breast tumors and other tissues

The surgical specimens were cut in sections and immediately frozen in liquid nitrogen for RNA analysis by Northern blot. Adjacent sections, fixed in 10% buffered formalin, were taken for histological examination and RNA in situ hybridization. Sections for immunohistochemical detection of ST3 protein were frozen in 2-methylbutane at −180° C.

RNA in situ hybridization in situ hybridization was performed on formalin-fixed paraffin-embedded tissue sections, as previously described (Basset, P., et al., *Nature* 348:699–704 (1990)) or using the modified procedure described by Shi et al. (*J. Histochem. Cytochem.* 39:741–748 (1991)). In brief, 6 μm-thick rehydrated and acid-treated sections were digested with proteinase K (2 μg/ml, 30 min, 37° C.) and, following overnight hybridization with [$^{35}$S]-labeled antisense RNA probes, the section were RNAse-treated (20 μg/ml, 30 min, 37° C.). In some cases, the sections were microwave-treated (3–5 min) prior to proteinase treatment. After autoradiography with NTB2 emulsion (Kodak), slides were developed and stained with hematoxylin. [$^{35}$S]-labeled antisense RNAs ($10^9$ cpm/μg) were obtained by in vitro transcription from the appropriate cDNA fragments subcloned into pBluescript II vector (stratagene) :stromelysin-1 (ST1), stromelysin-2 (ST2), ST3, interstitial type I collagenase (I COL/F) and pump-1 cDNAs, as previously described (Muller, D., et al., *Cancer Res.*, in press (1992)); a 92 k-Da type IV collagenase cDNA fragment (nucleotides 1678–2262; Wilhelm, S. M., et al., *J. Biol. Chem.* 264:17213–17221 (1989)) generated by PCR from breast cancer poly(A)$^+$ RNA (tumor C1, Basset, P., et al., *Nature* 348:699–704 (1990)); a 72 k-Da type IV collagenase cDNA fragment (nucleotides 261–2157; Collier, I. E., et al., *J. Biol. Chem.* 263:6579–6587 (1988)) obtained by screening of a breast cancer cDNA library with a 80 mer oligonucleotides specific for this cDNA (Basset, P., et al., Nature 348:699–704 (1990)); a 1.2 kb urokinase cDNA fragment (ATCC 57 329).

Antibody preparation and stromelysin-3 immunohistochemical analysis

Antiserum-containing polyclonal antibody 349 (Ab349) was obtained by rabbit immunization with a synthetic peptide corresponding to the 25C-terminal amino-acid residues of human ST3 (Basset, P., et al., Nature 348:699–704 (1990)), as previously described (Muller, D., et al., Cancer Res., in press (1993)). Antiserum was used at 1/1000 dilution for immunohistochemical analysis. Monoclonal antibody (Mab) 5ST-4A9-3 was obtained by mouse immunization with recombinant human ST3 produced in E. coli. Human ST3 cDNA (Basset, P., et al., Nature 348:699–704 (1990)) was mutagenized in vitro to engineer a Nde I ATG start-codon containing site, 5' to nucleotide 301. A 1367 bp long Nde I-Bst EII (filled) cDNA fragment, corresponding to the entire coding sequence for the putative mature form of human ST3 (Basset, P., et al., Nature 348:699–704 (1990)), was then subcloned into the expression vector pET-3b digested with Nde I-BamH I (filled). The construct was transformed into E. coli BL21 cells, grown using standard conditions, and ST3 recombinant protein extracted from inclusion bodies of BL21 cells. Inclusion bodies were solubilized in the presence of 100 mM KCl, 1 mM EDTA, 20 mM HEPES pH. 7.9., 100 mM DTT, 0.1% NP-40 and 8M urea, and ST3 renatured by dialysis against buffers with urea at progressively decreasing concentrations. After final dialysis against PBS and 100 000 g centrifugation for 1h, 8-week-old female Balb/c mice were injected intraperitoneally 3 times at 2-week intervals, with 40 μg of solubilized ST3 (about 50% pure). 4 days before the fusion, positive mice received a booster intraperitoneal injection of antigen (8 μg), and then 1 μg (intravenous and intraperitoneal routes) every day until spleen removal. The spleen cells were fused with Sp2/0-Ag14 myeloma cells essentially as described by St. Groth and Scheidegger, J. Immunol. Methods 35:1–21 (1980), except that interleukin-6 (200 U/ml) was added to the macrophage feeder cell layer. All culture supernatants were screened by immunocytochemical analysis on Cos-1 cells transfected with human ST3 cDNA, and by a differential ELISA test. Positive cultures were then tested by Western blot analysis on recombinant human ST3 produced in E. coli BL21 cells, and immunohistochemical analysis on human tissue sections. Specific hybridomas were cloned twice on soft agar. MAb 5ST-4A9-3 (IgG1) was selected, among 11 MAbs, for immunohistochemical analysis in routine, and used as ascites fluid diluted 1/500. Immunostaining was with a peroxidase-antiperoxidase (PAP) system (Dako), and a grading scheme (1 to 3+) was used to evaluate the level of ST3 protein in breast tumors, according to the following parameters: intensity of cytoplasmic staining, surface of ST3-expressing tumor areas, and percentage of ST3-expressing cells in the positive tumor areas.

Northern blot analysis

Total RNA from surgical specimens was extracted by guanidinium isothiocyanate solubilization, and prepared by cesium chloride gradient centrifugation. 8 μg of total RNA were separated by electrophoresis in 1% agarose gels containing formaldehyde, and blotted onto Hybond-N filters (Amersham). Hybridization and washing were performed under standard conditions, as described earlier (Basset, P., et al., Nature 348:699–704 (1990)). The probes (ST3, 72-kDa-type IV collagenase and urokinase cDNAs, described above) were [32P]-labeled, and, after dehybridization, the blots were reprobed with [32P]-labeled 36B4 cDNA in order to check for RNA loading and transfer.

RESULTS

Stromelysin-3 RNA expression in in situ breast carcinomas

ST3 gene expression was studied by RNA in situ hybridization in 35 ductal and 23 typical lobular in situ carcinomas (Table 3), corresponding to pure in situ carcinomas with no associated areas of invasive carcinoma. Interestingly, the number of tumors expressing detectable levels of ST3 transcripts in each subgroup of in situ carcinomas is correlated to the known risk that these tumors have to become invasive (Page and Dupont, Cancer 66:1326–1335 (1990); Harris, J. R., et al., N. Engl. J. Med. 327:319–328; 390–398; 473–480 (1992)). Thus, ST3 transcripts were detected in 61% of ductal in situ carcinomas of the comedo type, but in only 9% of lobular in situ carcinomas, and an intermediate value of 31% was obtained for ductal in situ carcinomas of the noncomedo types (Table 3). Furthermore, both the number of ducts associated with ST3 gene expression and the levels of ST3 transcripts were higher in in situ carcinomas of the comedo type, than in those of the other types (data not shown).

TABLE 3

Detection of stromelysin-3 RNA by in situ hybridization in breast tumors[1]

| | | Number of cases | |
|---|---|---|---|
| Diagnosis | | Total | Stromelysin-3 positive |
| Fibroadenomas | | 21 | 1 (5%) |
| In situ carcinomas | lobular | 25 | 2 (8%) |
| | ductal noncomedo | 22 | 7 (31%) |
| | ductal comedo | 13 | 8 (61%) |
| Invasive carcinomas | lobular | 12 | 10 (83%) |
| | ductal | 92 | 89 (97%) |
| Metastases | lymph nodes | 13 | 11 (85%) |
| | bone | 6 | 4 (67%) |
| | other organs | 9 | 4 (44%) |

[1]Each tumor was analysed with a single tissue section, and exposure time after hybridzation was 4 weeks, as described in "Materials and Methods")

As previously observed in invasive breast carcinomas (Basset, P., et al., Nature 348:699–704 (1990)), ST3 transcripts were not detected in the cancer cells themselves, but in fibroblastic cells of tumoral stroma (FIG. 13A–FIG. 13L), situated directly under the basement membrane (FIG. 13C and FIG. 13F) whose integrity can be questioned in some cases (FIG. 13F). However, in contrast to what is commonly observed in invasive carcinomas where ST3 transcripts are generally observed in the totality of the active epithelial-stromal interface, ST3 gene expression in in situ carcinomas was often focal (FIG. 13G and FIG. 13H) or segmental (FIG. 13A and FIG. 13B and FIG. 13D and FIG. 13E). Furthermore, in situ carcinomas expressing, or not, ST3 RNA could be observed in the same tumor (FIG. 13I–FIG. 13L), possibly associated with areas of invasive carcinoma (FIG. 13K and FIG. 13L).

Stromelysin-3 RNA expression in primary invasive carcinomas.

ST3 RNA has been detected in all the invasive ductal and lobular breast carcinomas so far tested in our laboratory by Northern blot analysis (FIG. 14 A and B; Basset, P., et al., Nature 348:699–704 (1990); and data not shown), but not in the normal breast samples tested in parallel (FIG. 14A). By RNA in situ hybridization, 10 (83%) of 12 invasive lobular and 89 (97%) of 92 invasive ductal carcinomas were found to express the ST3 gene, while only one of 21 breast fibroadenomas, which had been surgically removed from a pregnant patient, did express significant levels of ST3 RNA (Table 3).

Stromelysin-3 immunodetection in fibroblastic cells of breast carcinomas.

As expected from the above data, the ST3 protein could also be detected in primary breast carcinomas. Using frozen sections, it was present in 80 (78%) of 103 invasive ductal carcinomas, but only in one of 6 invasive lobular carcinomas and 3 of 12 in situ ductal carcinomas (Table 4), suggesting that protein detection may be less sensitive than RNA to evaluate ST3 gene expression. However, the frequence of ST3 positive tumors was similar to that found by RNA in situ hybridization when the immunohistological analysis was performed on microwave-treated paraffin-embedded tissue sections. The ST3 protein was present in the cytoplasm of elongated, fibroblast-like cells immediately surrounding islands of neoplastic cells, using either the polyclonal antibody 349 (FIG. 13M and data not shown) or the monoclonal antibody 5ST-4A9-3 (FIG. 13N and O, and data not shown). However, ST3 was neither detected in neoplastic cells nor in normal breast tissue located at distance from the cancer cells (data not shown). Taken together, these observations indicate that ST3 RNA and protein expression patterns are superimposable.

TABLE 4

Immunodetection[1] of stromelysin-3 in breast carcinomas

| Diagnosis | | Total | Stromelysin-3 positive | | | |
|---|---|---|---|---|---|---|
| | | | 1+ | 2+ | 3+ | Total |
| In situ carcinomas | lobular | 2 | 0 | 0 | 0 | 0 |
| | ductal | 12 | 1 | 1 | 1 | 3 |
| Invasive carcinomas | lobular | 6 | 0 | 1 | 0 | 1 |
| | ductal | 103 | 20 | 30 | 30 | 80 |

[1]Using monoclonal antibody 5ST-4A9-3 to human ST3 on frozen tissue sections
ST3 immunoscoring is defined in "Materials and Methods"

Stromelysin-3 RNA expression in metastatic breast carcinomas.

ST3 transcripts were detected by in situ hybridization in 19 (68%) of 28 breast cancer metastases (Table 3). ST3 transcripts were specifically detected in fibroblastic cells of metastatic tumors (FIG. 15A–FIG. 15H), as in the case of primary tumors. The tissular localization of the secondary tumors does not appear to be critical for the induction of ST3 gene expression, since ST3 transcripts were observed in fibroblastic cells of all types of breast cancer metastases tested, including those in lymph nodes, bone, skin, pleura and liver (Table 3; FIG. 15A–FIG. 15H; and data not shown). There was no strict correlation between ST3 RNA levels in primary tumors and metastatic lymph nodes from the same patient (FIG. 14B), and the low levels of ST3 transcripts in some metastatic nodes were not necessarily associated with a weak stromal reaction in the nodes (data not shown).

ST3 gene expression in breast carcinoma differs from that of other MMP genes but is similar to urokinase gene expression.

Thirteen breast tumors, including 2 fibroadenomas and 11 invasive ductal carcinomas, were evaluated by RNA in situ hybridization for expression of 7 MMP genes and of urokinase gene (Table 5). ST1 gene expression was not detected in any of the tumors analyzed, and ST2 and interstitial type I collagenase [I COL(F)] genes were expressed in some tumors only (Table 5). ST2 RNA was detected in one unique carcinoma, exhibiting malpighian differentiation, and in which ST2 transcripts were specifically detected in cancer cells distributed at the periphery of neoplastic islands (data not shown), as previously observed in squamous cell carcinomas of the head and neck (Muller, D., et al., Cancer Res., in press (1993)). In contrast, type I collagenase transcripts were exclusively detected in stromal fibroblasts surrounding islands of cancer cells, but, in one given tumor, the percentage of tumoral areas expressing the type I collagenase gene was generally lower than in the case of the ST3 gene (data not shown). Finally, ST2 and type I collagenase transcripts were not detected in the 2 fibroadenomas tested, nor in the normal breast structures also present in the tissue sections (Table 5, and data not shown).

TABLE 5

Comparative expression of Matrix metalloproteinase RNAs and of urokinase RNA in breast tumors[1]

| | Number of Positive Tumors | | |
|---|---|---|---|
| RNA | Adenomas[2] | Carcinomas[2] | Expressing Cell type |
| ST1 | 0 | 0 | — |
| ST2 | 0 | 1 | Neoplastic cells |
| 1 COL(F) | 0 | 3 | Fibroblastic cells |
| Pump-1 | 2 | 10 | Normal and neoplastic epithelial cells |
| IV COL(92) | 0 | 11 | Inflammatory and few neoplastic cells |
| IV COL(72) | 2 | 11 | Fibroblastic cells |
| ST3 | 0 | 11 | Fibroblastic cells |
| Urokinase | 0 | 11 | Fibroblastic and few neoplastic cells |

[1]Analyses performed by in situ hybridization, as described in "Materials and Methods"
[2]2 Fibroadenomas and 22 invasive carcinomas were analysed The other genes were expressed in most of the tumors analyzed (Table 5), and could be divided into two classes by their pattern of expression. In one class, which comprises pump-1 and 92-kDa type IV collagenase [IV COL(92)] genes, expression was exclusively observed in non-fibroblastic cells. Pump-1 transcripts were detected both in non-neoplastic and neoplastic epithelial cells, while 92-kDa type IV collagenase transcripts were found in inflammatory cells infiltrating the malignant tumors, and in few neoplastic cells (Table 5, and data not shown). In the second class, which comprises 72-kDa type IV collagenase [IV COL(72)], ST3 and urokinase (u-PA) genes, expression was exclusively, or mainly, observed in fibroblastic cells (Table 5, and FIG. 16A–FIG. 16I). In this second class, however, the 72-kDa type IV collagenase gene exhibited expression levels almost comparable in benign and malignant tumors, while ST3 and urokinase genes were expressed at significant levels in the malignant tumors only (FIG. 17). Furthermore, 72-kDa type IV collagenase (FIG. 16C), but not ST3 (FIG. 16D) nor urokinase (data not shown) transcripts, could be detected in fibroblastic cells at a distance from neoplastic cells (FIG. 16A). Thus, although the levels of ST3 RNA in breast carcinomas are generally higher than those of urokinase RNA (FIG. 17), the expression patterns of both genes appear very similar in breast carcinomas (FIG. 16D–FIG. 16I), suggesting that both proteinases may cooperate during breast cancer progression.

DISCUSSION

We have shown in the present study that the ST3 gene, which codes for a putative MMP (Basset, P., et al., Nature 348:699–704 (1990)), is expressed in most invasive breast carcinomas, but in only some in situ carcinomas. There is a positive correlation between ST3 gene expression and the known risk of in situ carcinomas to become invasive, suggesting that ST3 may be implicated in cancer cell invasion. In this respect, it is noteworthy that angiogenesis and HER-2 overexpression, which are believed to represent critical steps in the triggering of tumor invasion (Folkman, J., *Sem. Cancer Biol.* 3:65–71 (1992); Slamon, D. J., et al., *Science* 235:177–182 (1987)), are also observed in a number of in situ breast carcinomas (Weidner, N., et al., *N. Engl. J. Med.* 324:1–8 (1991); Van de Vijver, M. J., et al., *N. Engl. J. Med.* 319:1239–1245 (1988); Bartkova, J., et al., *Human Pathol.* 21:1164–1167 (1990)). However, the observation that some breast cancer metastases do not express significant levels of ST3 RNA suggests that some metastases may have acquired the capability of invading surrounding tissue independly of ST3 expression, an hypothesis consistent with the autonomous growth commonly attributed to metastatic cells.

The ST3 gene belongs to a subgroup of genes encoding proteinases possibly implicated in tumor progression, and which are not expressed in the cancer cells themselves, but in the fibroblastic cells of tumor stroma. In breast carcinomas this subgroup includes the genes encoding interstitial type I collagenase, the 72 kDa type IV collagenase and urokinase. ST3 transcripts are specifically detected in fibroblastic cells immediately surrounding the cancer cells in contrast to 72-kDa type IV collagenase transcripts, which are expressed in fibroblastic cells distributed throughout the tumoral stroma, as previously observed in skin (Pyke, C., et al., *Cancer Res.* 52, 1336–1341 (1992)) and colon carcinomas (Poulsom, R., et al., *Am. J. Path.* 141:388–398 (1992)). ST3 and urokinase transcripts, however, are expressed in the same fibroblastic compartment of breast carcinomas. This suggests that both genes could be similarly regulated and cooperate during breast cancer progression, an hypothesis also consistent with the observation that high levels of urokinase are associated with increased risk of relapse and death in breast cancer patients (Janicke, F., et al., *Fibrinolysis* 4:1–10 (1990); Duffy, M. J., et al., *Cancer Res.* 50:6827–6829 (1990); Sumiyoshi, K., et al., *Int. J. Cancer* 50:345–348 (1992)). However, the fibroblastic expression of the urokinase gene appears to be characteristic of adenocarcinomas (the present study and Grondhal-Hansen, J., et al., *Am. J. Pathol.* 138:111–117 (1991) and Pyke, C., et al., *Am. J. Pathol.* 138, 1059–1067 (1991)), since the gene is specifically expressed in the neoplastic cells of squamous cell carcinomas (Sappino, A. P., et al., *J. Clin. Invest.* 88:1073–1079 (1991); C. W. unpublished results). These observations contrast with that made for the ST3 gene, which was exclusively found to be expressed in fibroblastic cells in all the human carcinomas so far tested (Basset, P., et al., *Nature* 348:699–704 (1990); Wolf, C., et al., *J. Invest. Dermat.*, in press (1992); Muller, D., et al., *Cancer Res.*, in press (1993)).

The restricted expression of ST3 gene in fibroblastic cells immediately surrounding the neoplastic islands suggests that the cancer cells produce some inducive stimulus to trigger ST3 gene expression in the tumor stroma. However, the ST3 gene is also expressed in physiological situations, and in particular during embryonic development (Basset, P., et al., *Nature* 348:699–704 (1990); Wolf, C., et al., *J. Invest. Dermat.*, in press (1992)), mammary gland apoptosis (Lefebvre, O., et al., *J. Cell. Biol.*, 119:997–1002 (1992)), and in fibroblasts during the inflammatory phase of cutaneous wound healing (Wolf, C., et al., *J. Invest. Dermat.*, in press (1992)). The later observation suggests that inflammatory cells present in early stages of scar formation may produce cytokines(s) to trigger ST3 gene expression, and that these cells would play, toward the induction of ST3 gene expression, the role plaid by the neoplastic cells during tumor progression. In this respect, ST3 expression would represent a normal wound-healing response subverted in carcinomas, further illustrating the concept that "tumors are wounds that do not heal" (Dvorak, H. F., *N. Engl. J. Med.* 315:1650–1659 (1986); Whalen, G. F., *Lancet* 336:1489–1492 (1990)). Although its substrate is presently unknown, ST3 is likely to be a proteinase, since substitution of the zinc binding site of ST2 by the corresponding site of ST3, resulted in a chimera which exhibited strong proteolytic activity (M. Santavicca and PB, unpublished results). The identification of ST3 substrate is a prerequisite to better define the role of ST3 in cancer progression, and in particular to understand whether ST3 is a stroma-derived factor necessary for the progression of epithelial malignancies (Van den Hooff, *Cancer Cells* 3:186–187 (1991); Clarke, R., et al., in *Nuclear Hormone Receptors*, M. G. Parker, ed., Academic Press, 297–319 (1991)), or an autocrine factor necessary for the growth and/or migration of fibroblastic cells of tumoral stroma (Matrisian, L. M., *BioEssays* 14:455–463 (1992)). Independently of this issue, our observations indicate that ST3 gene expression is highly correlated with tumor invasion, and suggest that the presence of ST3 could be used as a new prognostic marker to define subpopulations of aggressive breast carcinomas.

EXAMPLE 12

Production of Antibodies to Stromelysin-3 (ST3)

8 week-old female Balb/c mice were used for immunization, except in the case of the 1ST MAbs and of the 3ST MAb (see Table 6) for which immunization was carried out with high responder Biozzi mice.

Mice were injected intraperitoneally 3 times at 2-week intervals with 100 µg of recombinant human ST3 (HE form, see below), in 250 µl PBS/250 µl complete Freund's adjuvant for the first injection, 250 µl PBS/250 of incomplete Freund's adjuvant for the second one; PBS alone for the third injection, supplemented with 100 µg double-stranded RNA (poly I/C). 4 days before the fusion, the mice were boostered intraperitoneally with 100 µg of coupled peptide or 8 µg of HE recombinant ST3 in presence of 100 µg poly I/C, followed every day until spleen removal by intravenous (150 µl) and intraperitoneal (500 µl) injections of 10 µg of coupled peptide or 1 µg of HE ST3, in PBS.

Mouse spleen cells were fused to the non-secreting myeloma cells Sp2/0-Ag14 essentially as described by St. Groth and Scheidegger except that interleukin-6 (200 U/ml) was added to the macrophage feeder cell layer. When immunization was performed with synthetic peptides, the initial screening of hybridoma culture supernatants was performed by an ELISA test using free (non coupled to ovalbumin) peptides as antigens. Positive cultures were then tested by immunofluorescence analysis (procedure described in Y. Lutz et al., *Exp. Cell. Res.* 175:109–124 (1988)) on Cos-1 cells, expressing various ST3 cDNAs. A third round of selection was performed by Western blot analysis using extracts of *E. coli* BL21 cells and of Cos-1 cells, expressing ST3 cDNAs. Finally, the hybridoma supernatants were tested immunohistochemistry on human tissue sections.

When immunization was performed with HE recombinant ST3, the hybridoma supernatants were tested by an immunocytochemical procedure which is described below, and by a differential ELISA test in which the antigens were HE recombinant ST3 produced in *E. coli*, and *E. coli* extracts containing no ST3 protein.

Immunocytochemical analysis was performed in 96-well culture plates after fixation of Cos-1 cells (transfected with various ST3 cDNAs in pSG5 expressing vector) with paraformaldehyde (2%, 4 min., and permeabilization with Triton X-100 (0.1%, 2×10 min). The secondary antibody was coupled to alkaline phosphatase, and staining was carried out with 0.1M Tris-HCI buffer pH 8.2, containing 1 mg/ml Fast Red (Pierce) and 0.2 mg NAMP/ml (Naphtol AS-MX phosphate, Fluka). The outstanding advantage of this technique over the ELISA test is to only reveal the cultures containing antibodies to ST3, but not those with antibodies to contaminant antigens, which are always present to a certain extent. The other rounds of selection were performed as in the case of immunization with antigenic peptides (see above). Finally, specific hybridomas were cloned twice on soft agar.

Subclass determination was performed using an isotyping kit (Amersham) and an ELISA test. MAbs obtained by immunization with HE recombinant ST3 have been classified in 2 distinct subgroups (Table 1, document B), by immunocytofluorescence and Western blot analyses of Cos-1 cells transfected with cDNA expressing the human ST3 with, or without, its hemopexin domain (see Document C, and Table 1 of document B).

None of the 3ST/5ST MAbs are directed to the 25 C-terminal amino-acid residues of human ST3, as seen by ELISA test. Although the 6ST and 7ST MAbs were generated by immunization with overlapping peptides, none of the MAbs obtained cross-reacted with the non-relevant peptide, as seen by ELISA test.

Hybridomas are normally cultured in RPMI medium containing 10% FCS. They can also be adapted to grow in defined culture media (SFRI.4 medium, SFRI laboratories, France, or Optimem medium, GIBCO, UK, supplemented with 2 g/l Albumex).

For ascites fluid production, $2.10^6$ cells were injected in pristane-primed Balb/c mice.

Utilizing the above procedures several antibody sera and lines have been developed. Utilizing a synthetic peptide corresponding to the 25 C-terminal amino acids of human ST3, an antibody designated AB 349 has been isolated. Utilizing recombinant human ST3 produced in *E. coli*, termed HE, and corresponding to the putative mature form of secreted ST3 as an immunogen Abs designated 216 & 217 have been isolated. Abs 216 and 217 are very similar with regard to their capability of immunodetecting ST3 (they correspond to two distinct rabbits).

Twenty-five different monoclonal antibodies (MAbs) to ST3 have been obtained and are described in Table 6, together with some of their characteristics. One of these MAbs, designated 5ST-4A9.3.6 has been deposited at the ECACC as ECACC 93010608 on Jan. 6, 1993, to the ECACC under the Budapest Treaty, PHLS Centre for Applied Microbiology and Research, Porton Down, Salisbury, Wilts, SP4 OJG, U.K. This antibody has shown the highest binding affinity and specificity of the antibodies thus far secreted and has been used in various histological and immunological studies.

TABLE 6

| | Monoclonal Antibodies to Stromelysin-3 | | | |
|---|---|---|---|---|
| name | antigene[1]/ immunization | epitope | immuno-histochemistry | subclass |
| 1 ST - 2H10 - 4 | 25 AT C-Term. | 25 AA C-Term. | +/++ | IgG1, κ |
| 1 ST - 4F6 - 5 | 25 AT C-Term. | 25 AA C-T | 0 | IgG2b, κ |
| 1 ST - 1H3 - 7 | 25 AT C-Term. | 25 AA C-T | 0 | IgG2b, κ |
| 1 ST - 4D8 - 12 | 25 AT C-Term. | 25 AA C-T | 0 | IgG1, κ |
| 1 ST - 4D12 - 2 | 25 AT C-Term. | 25 AA C-T | 0 | IgG1, κ |
| 3 ST - 4F3 - 11 | HE | hemopexin dom. | 0 | IgG3, κ |
| 5 ST - 1D12-38 | HE | catalytic dom. | 0 | IgG1, κ |
| 5 ST - 2G2 - 4 | HE | catalytic dom. | 0 | IgG1, κ |
| 5 ST 2H11-20 | HE | hemopexin dom. | ++ | IgG1, λ |
| 5 ST - 4A9 - 3[3] | HE | hemopexin dom. | +++ | IgG1, λ |
| 5 ST - 4C10-19 | HE | catalytic dom. | 0 | IgG1, κ |
| 5 ST- 1E4-2 | HE | hemopexin dom. | 0 | IgG1, κ |
| 5 ST - 1F1 - 21 | HE | hemopexin dom. | 0 | IgG1, λ |
| 5 ST - 1F7 - 4 | HE | hemopexin dom. | 0 | IgG1, κ |
| 5 ST - 4F11 - 3 | HE | hemopexin dom. | ++/+++ | IgG1, λ |
| 5 ST - 3F4 - 4 | HE | hemopexin dom. | 0 | IgG1, λ |
| 4 ST - 8D5 - 16 | AA 88 - 97[2] | AA 88 - 97 | 0 | IgG1, κ |
| 6 ST - 4A12 - 37 | AA 41 - 60[3] | AA 41 - 60 | 0 | IgG1, κ |
| 6 ST - 1E11 - 44 | AA 41 - 60 | AA 41 - 60 | + | IgG1, κ |
| 6 ST - 2E1 - 24 | AA 41 - 60 | AA 41 - 60 | 0 | IgG1, κ |
| 6 ST - 4E3 - 7 | AA 41 - 60 | AA 41 - 60 | 0 | IgG1, κ |
| 6 ST - 4E5 - 12 | AA 41 - 60 | AA 41 - 60 | 0 | IgG1, κ |
| 6 ST - 1F11 - 9 | AA 41 - 60 | AA 41 - 60 | + | IgG1, κ |
| 7 ST - 1C3 - 1 | AA 57 - 76[3] | AA 57 - 76 | 0 | IgG1, κ |
| 7 ST - 1C4 - 18 | AA 57 - 76 | AA 57 - 76 | 0 | IgG1, κ |

[1]10 AA specific for ST3
[2]located in human ST3 prodomain
[3]deposited at the ECACC as ECACC 93010608

None of the MAbs were found to cross-react with stromelysin-1 and 2 or with pump-1 enzymes, which belong to the same proteinase family as ST3 (tests performed by immunocytofluorescence analysis on Cos-1 cells transfected with the appropriate cDNAs in pSG5 vector).

We claim:

1. A method for detecting human stromelysin-3 which comprises the steps of
    a. contacting a sample or preparation thereof with an antibody or antibody fragment which selectively binds stromelysin-3, and
    b. detecting whether said antibody or said antibody fragment is bound by said sample and thereby detecting stromelysin-3.

2. The method according to claim 1, wherein said antibody, or said antibody fragment, is detectably labelled.

3. The method of claim 1 wherein said antibody is the 5ST-4A9-3 antibody produced by the hybridoma ECACC 93010608.

4. An isolated antibody or antibody fragment which selectively binds human stromelysin-3.

5. The antibody of claim 4 wherein said antibody is the 5ST-4A9-3 antibody produced by the hybridoma ECACC 93010608.

6. The antibody or antibody fragment of claim 4, wherein said antibody or antibody fragment is detectably labelled.

* * * * *